US008895717B2

(12) United States Patent
Sood et al.

(10) Patent No.: US 8,895,717 B2
(45) Date of Patent: Nov. 25, 2014

(54) DELIVERY OF SIRNA BY NEUTRAL LIPID COMPOSITIONS

(75) Inventors: Anil K. Sood, Pearland, TX (US); Gabriel Lopez-Berestein, Bellaire, TX (US); Charles N. Landen, Pearland, TX (US); Arturo Chavez-Reyes, Monterrey (MX)

(73) Assignee: The Board of Regents of the University of Texas System, Austin, TX (US)

( * ) Notice: Subject to any disclaimer, the term of this patent is extended or adjusted under 35 U.S.C. 154(b) by 1895 days.

(21) Appl. No.: 11/911,639

(22) PCT Filed: Apr. 17, 2006

(86) PCT No.: PCT/US2006/014501
§ 371 (c)(1),
(2), (4) Date: Aug. 12, 2008

(87) PCT Pub. No.: WO2006/113679
PCT Pub. Date: Oct. 26, 2006

(65) Prior Publication Data
US 2009/0012021 A1 Jan. 8, 2009

Related U.S. Application Data

(60) Provisional application No. 60/671,641, filed on Apr. 15, 2005.

(51) Int. Cl.
C07H 21/04 (2006.01)
C12N 15/113 (2010.01)
A61K 48/00 (2006.01)
C12N 15/11 (2006.01)

(52) U.S. Cl.
CPC .......... *C12N 15/111* (2013.01); *C12N 2310/14* (2013.01); *C12N 15/1138* (2013.01); *C12Y 207/10001* (2013.01); *A61K 48/0025* (2013.01); *C12N 15/1137* (2013.01); *C12N 2320/32* (2013.01)
USPC ...................................................... 536/24.5

(58) Field of Classification Search
USPC ........................................................ 536/24.5
See application file for complete search history.

(56) References Cited

U.S. PATENT DOCUMENTS

| 4,663,167 | A | 5/1987 | Lopez-Berestein et al. ..... 514/37 |
| 4,812,312 | A | 3/1989 | Lopez-Berestein et al. .... 424/417 |
| 4,863,739 | A | 9/1989 | Perez-Soler et al. .......... 424/450 |
| 4,950,432 | A | 8/1990 | Mehta et al. .................... 264/4.6 |
| 4,978,654 | A | 12/1990 | Lopez-Berestein et al. .... 424/450 |
| 4,981,690 | A | 1/1991 | Lopez-Berestein et al. .... 424/422 |
| 5,030,453 | A | 7/1991 | Lenk et al. ..................... 424/450 |
| 5,032,404 | A | 7/1991 | Lopez-Berestein et al. .... 424/450 |
| 5,041,581 | A | 8/1991 | Khokhar et al. ................ 556/137 |
| 5,117,022 | A | 5/1992 | Khokhar et al. ................ 556/137 |
| 5,178,875 | A | 1/1993 | Lenk et al. ..................... 424/450 |
| 5,178,876 | A | 1/1993 | Khokhar et al. ............... 424/450 |
| 5,186,940 | A | 2/1993 | Khokhar et al. ............... 424/450 |
| 5,198,428 | A | 3/1993 | Sivaramakrishnan et al. ... 514/54 |
| 5,213,970 | A | 5/1993 | Lopez-Berestein et al. . 435/70.4 |
| 5,417,978 | A | 5/1995 | Tari et al. ....................... 424/450 |
| 5,811,119 | A | 9/1998 | Mehta et al. ................... 424/450 |
| 5,830,498 | A | 11/1998 | Lenk et al. ..................... 424/450 |
| 5,855,911 | A | 1/1999 | Lopez-Berestein et al. .. 424/450 |
| 5,962,016 | A | 10/1999 | Willis ............................. 424/450 |
| 5,965,158 | A | 10/1999 | Link et al. ...................... 424/450 |
| 5,968,737 | A | 10/1999 | Ali-Osman et al. ............... 435/6 |
| 6,042,846 | A | 3/2000 | Lopez-Berestein et al. .. 424/450 |
| 6,107,457 | A | 8/2000 | Arlinghaus et al. ........... 530/300 |
| 6,133,031 | A * | 10/2000 | Monia et al. ................... 435/375 |
| 6,200,597 | B1 | 3/2001 | Mehta et al. ................... 424/450 |
| 6,458,382 | B1 | 10/2002 | Herweijer et al. ............. 424/450 |
| 6,506,559 | B1 | 1/2003 | Fire et al. ........................... 435/6 |
| 6,534,484 | B1 | 3/2003 | Wheeler et al. ............. 514/44 R |
| 6,537,804 | B1 | 3/2003 | Arlinghaus et al. ........ 435/320.1 |
| 6,573,099 | B2 | 6/2003 | Graham ......................... 435/455 |
| 6,593,294 | B1 | 7/2003 | Baru et al. .......................... 514/2 |
| 6,673,611 | B2 | 1/2004 | Thompson et al. ............ 435/455 |
| 6,680,068 | B2 | 1/2004 | Campbell et al. ............. 424/450 |
| 6,977,244 | B2 | 12/2005 | Tormo et al. ..................... 514/44 |
| 7,176,302 | B2 | 2/2007 | Lopez-Berestein et al. . 536/24.5 |
| 7,220,853 | B2 | 5/2007 | Lopez-Berestein et al. . 536/24.5 |
| 7,285,288 | B1 * | 10/2007 | Tormo et al. ................... 424/450 |
| 7,309,692 | B1 | 12/2007 | Lopez-Berestein et al. .... 514/44 |
| 7,378,249 | B2 | 5/2008 | Andre et al. ................... 435/7.1 |
| 7,754,872 | B2 * | 7/2010 | Lopez-Berestein et al. . 536/24.5 |
| 7,807,815 | B2 * | 10/2010 | MacLachlan et al. ....... 536/24.5 |
| 8,101,343 | B2 * | 1/2012 | Whyard et al. ................ 435/6.1 |

(Continued)

FOREIGN PATENT DOCUMENTS

WO   WO 97/14685    4/1997
WO   WO 02/062316   8/2002

(Continued)

OTHER PUBLICATIONS

Semple et al. BBA 1510: 152-166, 2001.*
Leonetti et al. (Cancer Gene Therapy (2001, 8, 459-468).*
Stuart et al. (BBA, 1463 (2000), 219-229.*
Ambros, "The function of animal microRNAs," *Nature*, 431:350-5, 2004.
Bailey and Sullivan, "Efficient encapsulation of DNA plasmids in small neutral liposomes induced by ethanol and calcium," *Biochimica. Biophys. Acts.*, 239-252, 2000.
Beale et al., "Gene silencing nucleic acids designed by scanning arrays: anti-EGFR activity of siRNA, ribozyme and DNA enzymes targeting a single hybridization-accessible region using the same delivery system," *J. Drug Target*, 11:449-56, 2003.

(Continued)

*Primary Examiner* — Brian Whiteman
(74) *Attorney, Agent, or Firm* — Parker Highlander PLLC

(57) ABSTRACT

The present invention relates to the fields of molecular biology and drug delivery. In certain embodiments, the present invention provides methods for the delivery of a siNA (e.g., a siRNA) to a cell via a neutral (non-charged) liposome. These methods may be used to treat a disease, such as cancer.

12 Claims, 20 Drawing Sheets

(56) References Cited

U.S. PATENT DOCUMENTS

| | | | |
|---|---|---|---|
| 8,263,573 B2* | 9/2012 | Whyard et al. | 514/44 R |
| 8,415,320 B2* | 4/2013 | Whyard et al. | 514/44 R |
| 2002/0090392 A1 | 7/2002 | Campbell et al. | 424/450 |
| 2002/0143062 A1 | 10/2002 | Lopez-Berestein et al. | 514/613 |
| 2002/0168707 A1 | 11/2002 | Graham | 435/69.1 |
| 2003/0012812 A1 | 1/2003 | Tormo et al. | 424/450 |
| 2003/0051263 A1 | 3/2003 | Fire et al. | 800/13 |
| 2003/0055020 A1 | 3/2003 | Fire et al. | 514/44 |
| 2003/0064948 A1 | 4/2003 | Fahr et al. | 514/44 |
| 2003/0100480 A1 | 5/2003 | Smith et al. | 514/1 |
| 2003/0129222 A1 | 7/2003 | Lopez-Berestein et al. | 424/450 |
| 2003/0153526 A1 | 8/2003 | Lopez-Berestein et al. | 514/44 |
| 2003/0154504 A1 | 8/2003 | Farese et al. | 800/18 |
| 2003/0157514 A1 | 8/2003 | Finger et al. | 435/6 |
| 2003/0159161 A1 | 8/2003 | Graham et al. | 800/8 |
| 2003/0165934 A1 | 9/2003 | Elledge et al. | 435/6 |
| 2003/0170642 A1 | 9/2003 | Caldwell et al. | 435/6 |
| 2003/0203865 A1* | 10/2003 | Harvie et al. | 514/44 |
| 2003/0219474 A1 | 11/2003 | Tormo et al. | 424/450 |
| 2004/0002153 A1* | 1/2004 | Monia et al. | 435/375 |
| 2004/0005353 A1 | 1/2004 | Lopez-Berestein et al. | 424/450 |
| 2004/0019001 A1 | 1/2004 | McSwiggen | 514/44 |
| 2004/0022772 A1 | 2/2004 | Arlinghaus et al. | 424/93.21 |
| 2004/0028685 A1 | 2/2004 | Kinch et al. | 424/155.1 |
| 2004/0043950 A1 | 3/2004 | Lopez-Berestein et al. | 514/44 |
| 2004/0043952 A1 | 3/2004 | Niedzinski et al. | 514/44 |
| 2004/0064842 A1 | 4/2004 | Graham et al. | 800/8 |
| 2004/0106132 A1 | 6/2004 | Huang et al. | 435/6 |
| 2004/0115254 A1 | 6/2004 | Niedzinski et al. | 424/450 |
| 2004/0115671 A1 | 6/2004 | Zlokovic et al. | 435/6 |
| 2004/0126784 A1* | 7/2004 | Hitoshi et al. | 435/6 |
| 2004/0142025 A1 | 7/2004 | MacLachlan et al. | 424/450 |
| 2004/0142892 A1 | 7/2004 | Finn et al. | 514/44 |
| 2004/0176282 A1 | 9/2004 | Dalby et al. | 514/8 |
| 2004/0198655 A1 | 10/2004 | Mantovani | 514/12 |
| 2004/0203145 A1 | 10/2004 | Zamore et al. | 435/6 |
| 2004/0204377 A1 | 10/2004 | Rana | 514/44 |
| 2004/0208921 A1 | 10/2004 | Ho et al. | 424/450 |
| 2004/0214771 A1 | 10/2004 | Schwartz et al. | 514/12 |
| 2004/0242518 A1 | 12/2004 | Chen et al. | 514/44 |
| 2004/0265839 A1 | 12/2004 | Mello et al. | 435/6 |
| 2005/0008664 A1 | 1/2005 | Claxton et al. | 424/401 |
| 2005/0107325 A1* | 5/2005 | Manoharan et al. | 514/44 |
| 2005/0191344 A1* | 9/2005 | Zalipsky et al. | 424/450 |
| 2006/0134221 A1* | 6/2006 | Geall | 424/489 |
| 2006/0240093 A1* | 10/2006 | MacLachlan et al. | 424/450 |
| 2006/0251726 A1 | 11/2006 | Lin et al. | 424/489 |
| 2007/0003607 A1 | 1/2007 | Awasthi et al. | 424/450 |
| 2007/0116767 A1* | 5/2007 | Mohapatra | 424/489 |
| 2007/0202157 A1 | 8/2007 | Lopez-Berestein et al. | 424/450 |
| 2007/0238686 A1 | 10/2007 | Lopez-Berestein et al. | 514/44 |
| 2008/0312096 A1* | 12/2008 | Gray et al. | 506/9 |
| 2008/0317811 A1 | 12/2008 | Andre et al. | 424/423 |

FOREIGN PATENT DOCUMENTS

| | | |
|---|---|---|
| WO | WO 02/072783 | 9/2002 |
| WO | WO 02/100435 | 12/2002 |
| WO | WO 03/004644 * | 1/2003 |
| WO | WO 03/015757 | 2/2003 |
| WO | WO 03/044214 | 5/2003 |
| WO | WO 03/055914 | 7/2003 |
| WO | WO 03/057164 | 7/2003 |
| WO | WO 2004/002453 | 1/2004 |
| WO | WO 2004/026453 | 4/2004 |
| WO | WO 2004/029213 | 4/2004 |
| WO | WO 2004/035523 | 4/2004 |
| WO | WO 2004/064731 | 8/2004 |
| WO | WO 2004/094595 | 11/2004 |
| WO | WO 2004/108938 | 12/2004 |
| WO | WO 2005/026372 | 3/2005 |
| WO | WO 2006/054177 | 5/2006 |
| WO | WO 2006/081158 | 8/2006 |
| WO | WO 2006/113679 | 10/2006 |

OTHER PUBLICATIONS

Devroe and Silver, "Therapeutic potential of retroviral RNAi vectors," *Expert Opin. Biol. Ther.*, 4:319-27, 2004.

Dobrzanski et al., "Antiangiogenic and antitumor efficacy of EphA2 receptor antagonist," *Cancer Res.*, 64:910-9, 2004.

Donzé and Picard, "RNA interference in mammalian cells using siRNAs syntehsized with T7 RNA polymerase," *Nucleic Acids Res.*, 30:e46, 2002.

Dorn et al., "siRNA relieves chronic neuropathic pain," *Nucleic Acids Res.*, 32:e49, 2004.

Dubey et al., "Liposomes modified with cyclic RGD peptide for tumor targeting," *J. Drug Target.*, 12:257-64, 2004.

Duxbury et al., "EphA2: a determinanat of malignant cellular behavior and a potential therapeutic target in pancreatic adenocarcinoma," *Oncogene*, 23:1448-56, 2004.

Duxbury et al., "RNA interference targeting focal adhesion kinase enhances pancreatic adenocarcinoma gemcitabine chemosensitivity," *Biochem. Biophys. Res. Commun.*, 311:786-92, 2003.

Duxbury et al., "Systemic siRNA-mediated gene silencing: a new approach to targeted therapy of cancer," *Ann. Surg.*, 240:667-76, 2004.

Elmen et al., "Locked nucleic acid (LNA) mediated improvements in siRNA stability and functionality," *Nucleic Acids Res.*, 33:439-47, 2005.

Fire et al., "Potent and specific genetic interference by double-stranded RNA in *Caenorhabditis elegans*," *Nature*, 391:806-11, 1998.

Gutierrez-Puente et al., "Safety, pharmacokinetics, and tissue distribution of liposomal P-ethoxy antisense oligonucleotides targeted to Bcl-2," *J. Pharmacol. Exp. Ther.*, 291:865-9, 1999.

Hannon and Rossi, "Unlocking the ptential of the human genome with RNA interference," *Nature*, 431:371-8, 2004.

Hassani et al., "Lipid-mediated siRNA delivery down-regulates exogenous gene expression in the mouse brain at picomolar levels," *J. Gene Med.*, 7:198-207, 2005.

Jemal et al., "Cancer statistics, 2004," *CA Cancer J. Clin.*, 54:8-29, 2004.

Kinch and Carles-Kinch, "Overexpression and functional alterations of the EphA2 tyosine kinase in cancer," *Clin. Exp. Metastasis*, 20:59-68, 2003.

Landen, "Therapeutic EphA2 gene targeting in vivo using neutral liposomal small interfering RNA delivery," *Cancer Res.*, 65:6910-18, 2005.

Leung and Whittaker, "RNA interference: from gene silencing to gene-specific therapeutics," *Pharmacol. Ther.*, 107:222-39, 2005.

Lewis et al., "Prediction of mammalian microRNA targets," *Cell*, 115:787-98, 2003.

Li and Deng, "A novel for the preparation of liposomes: freeze drying of monophase solutions," *J. Pharm. Sci.*, 93:1403-14, 2004.

Lorenz et al., "Steroid and lipid conjugates of siRNAs to enhance cellular uptake and gene silencing in liver cells," *Bioorg. Med. Chem. Lett.*, 14:4975-7, 2004.

McCaffrey et al., "RNA interference in adult mice," *Nature*, 418:38-9, 2002.

Miller et al., "Liposome-cell interactions in vitro: effect of liposome surface charge on the binding and endocytosis of conventional and sterically stabilized liposomes," *Biochemistry*, 37:12875-83, 1998.

Muratovska and Eccles, Conjugate for efficient delivery of short interfering RNA (siRNA) into mammalian cells, *FEBS Lett.*, 558:63-8, 2004.

Noblitt et al., "Decreased tumorigenic potential of EphA2-overexpressing breast cancer cells following treatment with adenoviral vectors that express EphrinAl," *Cancer Gene Ther.*, 11:757-66, 2004.

Ogawa et al., "The ephrin-A1 ligand and its receptor, EphA2, are expressed during tumor neovascularization," *Oncogene*, 19:6043-52, 2000.

PCT International Search Report and Written Opinion, issued in International Application PCT/US06/14501, dated May 23, 2007.

Reich et al., "Small interfering RNA (siRNA) targeting VRGF effectively inhibits ocular neovascularization in a mouse model," *Mol. Vis.*, 9:210-6, 2003.

(56) References Cited

OTHER PUBLICATIONS

Rui and Su, "Co-transfection of p16(INK4a) and p53 genes into the K562 cell line inhibits cell proliferation," *Haematologica*, 87:136-42, 2002.

Ryther et al., "siRNA therapeutics: big potential from small RNAs," *Gene Therapy*, 12:5-11, 2005.

Sioud and Sorensen, "Cationic liposome-mediated delivery of siRNAs in adult mice," *Biochem. Biophys. Res. Comm.*, 312:1220-1225, 2003.

Soutschek et al., "Therapeutic silencing of an endogenous gene by systemic administration of modified siRNAs," *Nature*, 432:173-8, 2004.

Spagnou et al., "Lipidic carriers of siRNA: differences in the formulation, cellular uptake, and delivery with plasmid DNA," *Biochemistry*, 43:13348-56, 2004.

Surowiak, "Evaluation of trasfection effectiveness using fluorescein-labelled oligonucleotides and various liposomes," *Folia, Morphol. (Warsz.)*, 62:397-9, 2003.

Thaker et al., "EphA2 expression is associated with aggressive features in ovarian carcinoma," *Clin. Cancer Res.*, 10:5145-50, 2004.

Thurston et al., "Cationic liposomes target angiogenic endothelial cells in tumors and chronic inflammation in mice," *J. Clin. Invest.*, 101:1401-13, 1998.

Voskoglou-Nomikos et al., "Clinical predictive value of the in vitro cell line, human xenograft, and mouse allograft preclinical cancer models," *Clin. Cancer Res.*, 9:4227-39, 2003.

Walker-Daniels et al., "Overexpression of the EphA2 tyrosine kinase in prostate cancer," *Prostate*, 41:275-80, 1999.

Wianny and Zernicka-Goetz, "Specific interference with gene function by double-stranded RNA in early mouse development," *Nat. Cell. Biol.*, 2:70-5, 2000.

Xia et al., "siRNA-mediated gene silencing in vitro and in vivo," *Nat. Biotechnol.*, 20:1006-10, 2002.

Yang et al., "Silencing of H-ras gene expression by retrovirus-mediated siRNA decreases transformation efficiency and tumor growth in a model of human ovarian cancer," *Oncogene*, 22:5694-701, 2003.

Zelinski et al., "EphA overexpression causes tumorigenesis of mammary epithelial cells," *Cancer Res.*, 61:2301-6, 2001.

European Search Report, issued in European Application No. 06758388.0, dated Nov. 26, 2008.

GenBank Accession No. NM_005607, 1994.

GenBank Accession No. NM_153831, 1994.

GenBank Accession No. BC037166 (GI:33879863), 2002.

GenBank Accession No. AF022953 (GI:2570526), 1994.

Office Communication, issued in Australian Patent Application No. 2006236453, dated Feb. 7, 2011.

Office Action issued in U.S. Appl. No. 12/527,684, mailed Dec. 14, 2010.

* cited by examiner

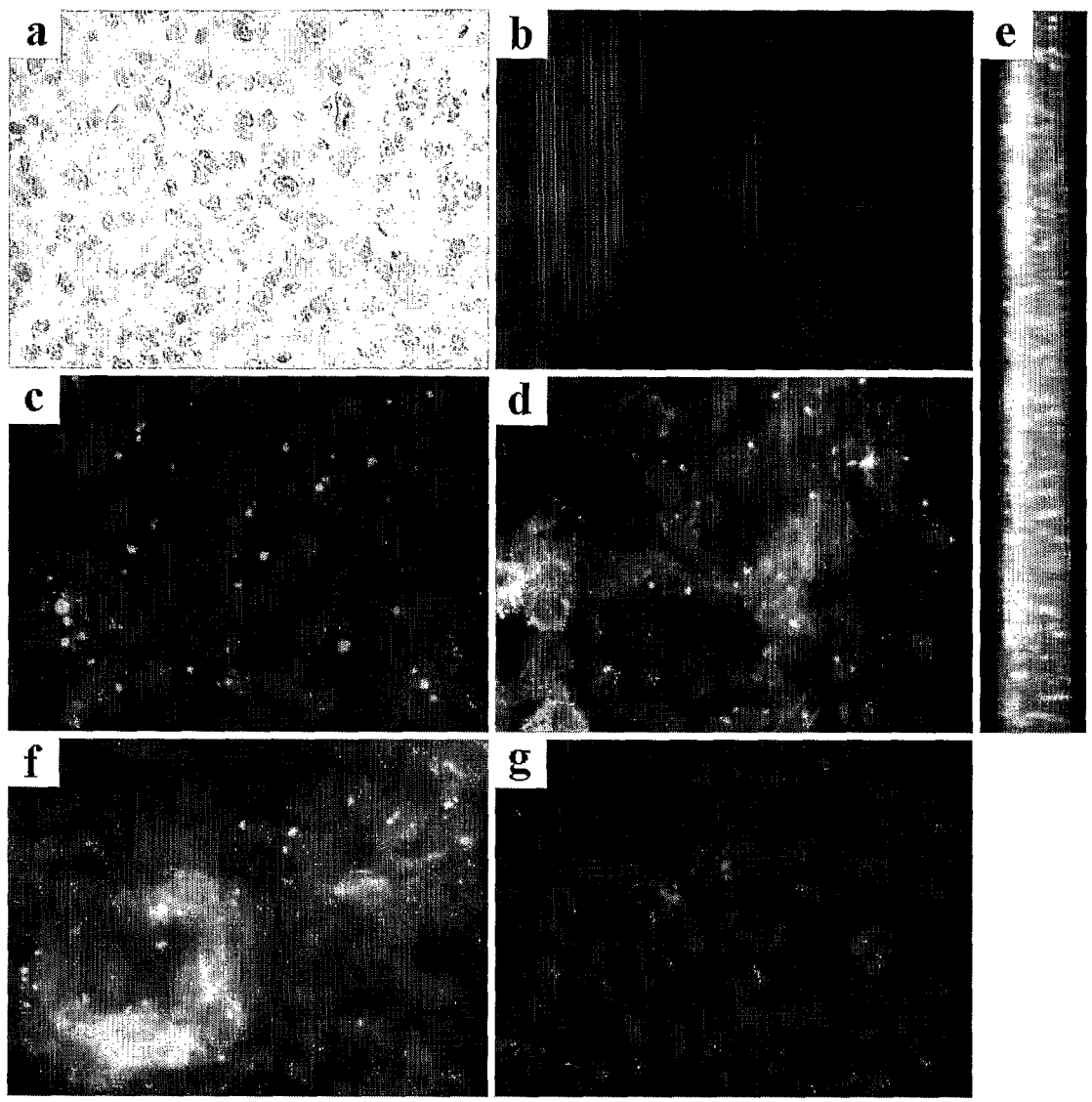
FIGS. 1A-G

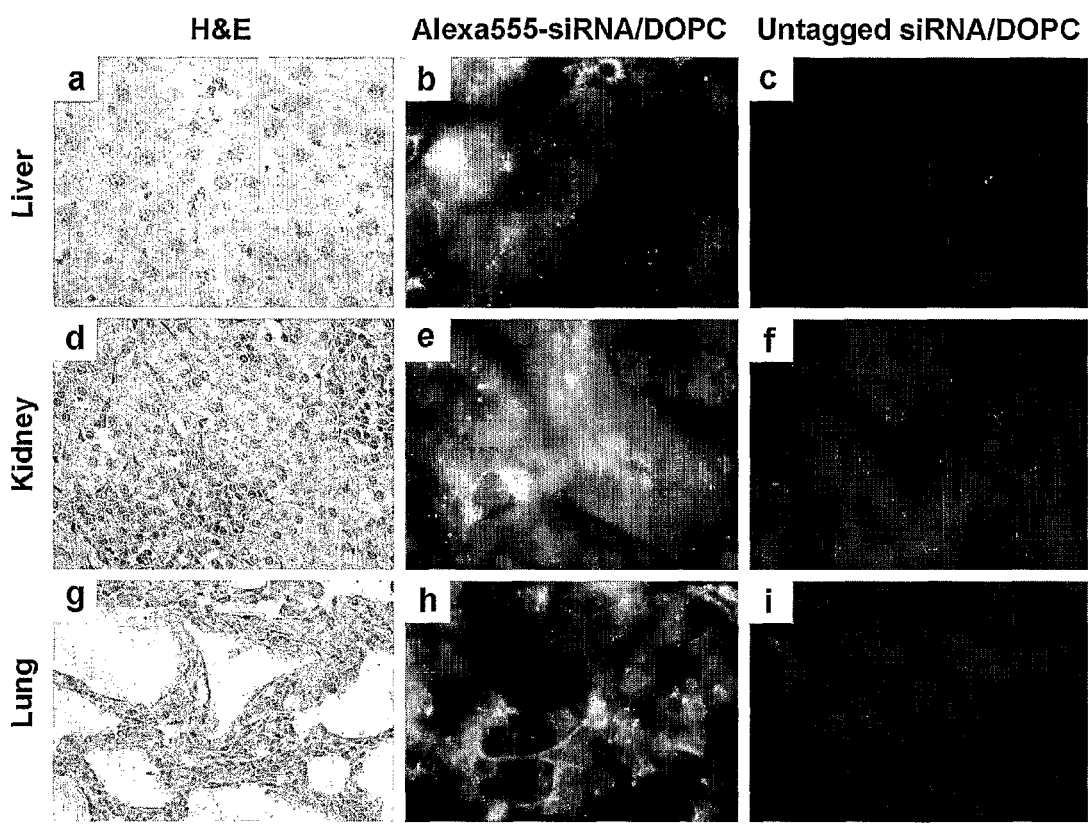
FIGS. 2A-I

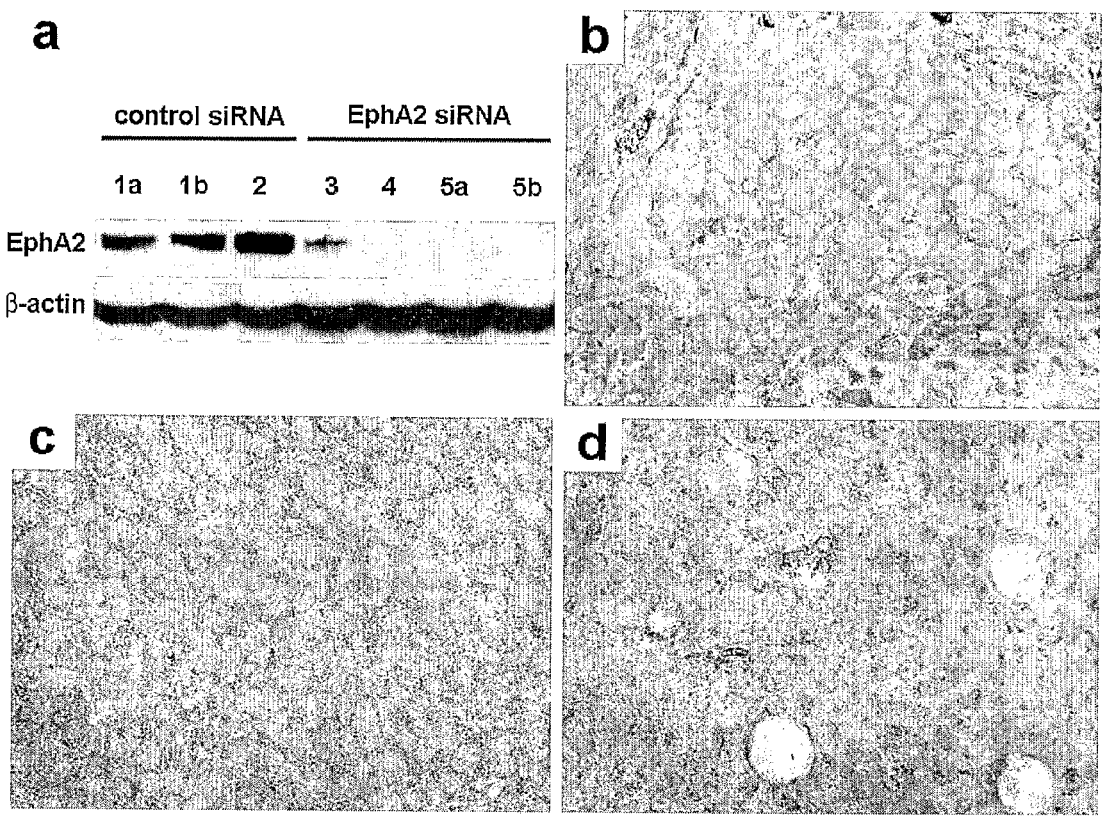
FIGS. 3A-D

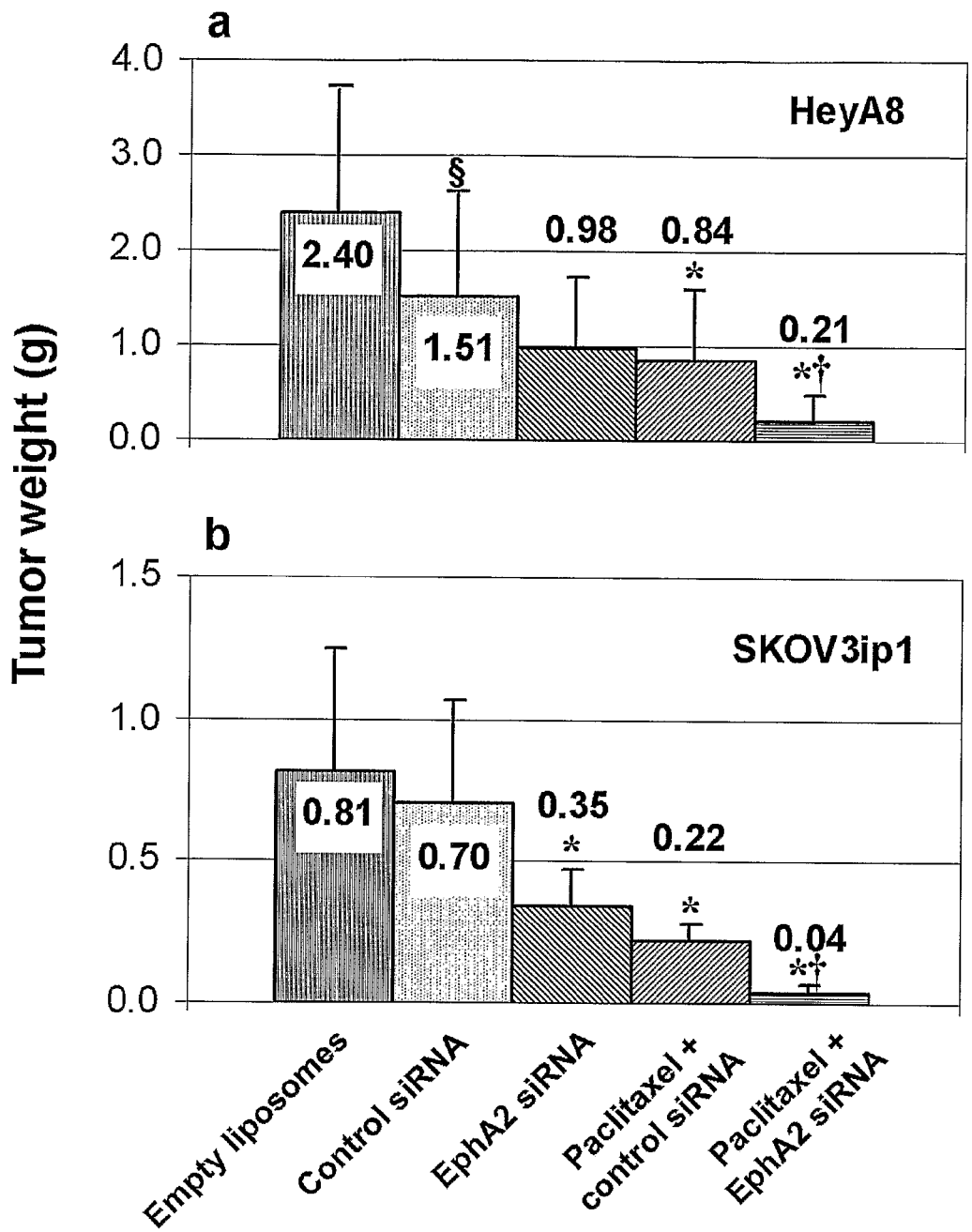
FIGS. 4A-B

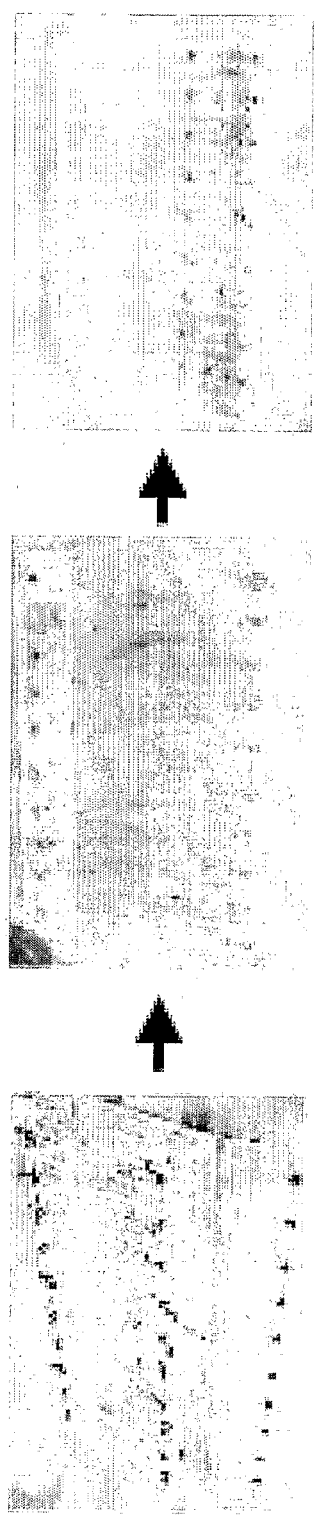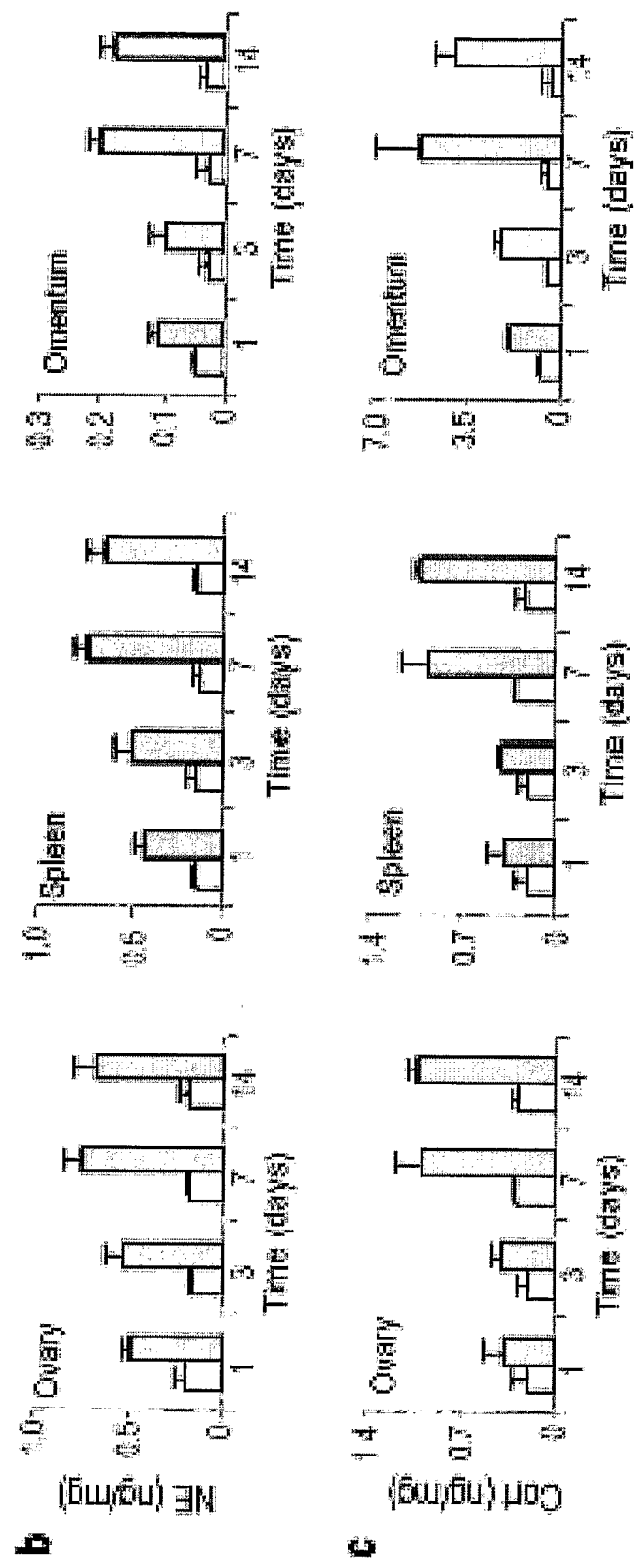
FIG. 15A-15C

SEQUENCE LISTING

<160> NUMBER OF SEQ ID NOS: 19

<210> SEQ ID NO 1
<211> LENGTH: 21
<212> TYPE: DNA
<213> ORGANISM: Artificial Sequence
<220> FEATURE:
<223> OTHER INFORMATION: Synthetic primer

<400> SEQUENCE: 1
aattctccga acgtgtcacg t                                            21

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2
aatgacatgc cgatctacat g                                            21

```
<210> SEQ ID NO 3
<211> LENGTH: 21
<212> TYPE: RNA
<213> ORGANISM: Artificial Sequence
<220> FEATURE:
<223> OTHER INFORMATION: Synthetic primer

<400> SEQUENCE: 3
aauucuccga acgugucacg u                                              21

<210> SEQ ID NO 4
<211> LENGTH: 21
<212> TYPE: RNA
<213> ORGANISM: Artificial Sequence
<220> FEATURE:
<223> OTHER INFORMATION: Synthetic primer

<400> SEQUENCE: 4
aaugacaugc cgaucuacau g                                              21

<210> SEQ ID NO 5
<211> LENGTH: 4442
<212> TYPE: DNA
<213> ORGANISM: Homo sapiens

<400> SEQUENCE: 5
gaccactgtg agcccgcggc gtgaggcgtg ggaggaagcg cggctgctgt cgcccagcgc      60
cgccccgtcg tcgtctgcct tcgcttcacg gcgccgagcc gcggtccgaa gtcttgctgt     120
gtcacccagg ctgccaggct ggagtggagt ggcatgatct cggctgactg caacctctgc     180
ctcccagaat atgacagata cctagcatct agcaaaataa tggcagctgc ttaccttgac     240
cccaacttga atcacacacc aaattcgagt actaagactc acctgggtac tggtatggaa     300
cgttctcctg gtgcaatgga gcgagtatta aaggtctttc attattttga aagcaatagt     360
gagccaacca cctgggccag tattatcagg catggagatg ctactgatgt caggggcatc     420
attcagaaga tagtggacag tcacaaagta aagcatgtgg cctgctatgg attccgcctc     480
agtcacctgc ggtcagagga ggttcactgg cttcacgtgg atatgggcgt ctccagtgtg     540
agggagaagt atgagcttgc tcacccacca gaggagtgga aatatgaatt gagaattcgt     600
tatttgccaa aaggatttct aaaccagttt actgaagata agccaacttt gaatttcttc     660
tatcaacagg tgaagagcga ttatatgtta gagatagctg atcaagtgga ccaggaaatt     720
gctttgaagt tgggttgtct agaaatacgg cgatcatact gggagatgcg gggcaatgca     780
ctagaaaaga agtctaacta tgaagtatta gaaaagatg ttggtttaaa gcgatttttt     840
cctaagagtt tactggattc tgtcaaggcc aaaacactaa gaaaactgat ccaacaaaca     900
tttagacaat ttgccaacct aatagagaaa gaaagtattc tgaaattctt tgagatcctg     960
tctccagtct acagatttga taaggaatgc ttcaagtgtg ctcttggttc aagctggatt    1020
atttcagtgg aactggcaat cggcccagaa gaaggaatca gttacctaac ggacaagggc    1080
tgcaatccca cacatcttgc tgacttcact caagtgcaaa ccattcagta ttcaaacagt    1140
gaagacaagg acagaaaagg aatgctacaa ctaaaaatag caggtgcacc cgagcctctg    1200
acagtgacgg caccatccct aaccattgcg gagaatatgg ctgacctaat agatgggtac    1260
tgccggctgg tgaatggaac ctcgcagtca tttatcatca gacctcagaa agaaggtgaa    1320
cgggctttgc catcaatacc aaagttggcc aacagcgaaa gcaaggcat gcggacacac    1380 gccgtctctg tgtcagaaac agatgattat gctgagatta tagatgaaga agatacttac    1440
```

```
accatgccct caaccaggga ttatgagatt caaagagaaa gaatagaact tggacgatgt    1500
attggagaag gccaatttgg agatgtacat caaggcattt atatgagtcc agagaatcca    1560
gctttggcgg ttgcaattaa aacatgtaaa aactgtactt cggacagcgt gagagagaaa    1620
tttcttcaag aagccttaac aatgcgtcag tttgaccatc ctcatattgt gaagctgatt    1680
ggagtcatca cagagaatcc tgtctggata atcatggagc tgtgcacact tggagagctg    1740
aggtcatttt tgcaagtaag gaaatacagt ttggatctag catctttgat cctgtatgcc    1800
tatcagctta gtacagctct tgcatatcta gagagcaaaa gatttgtaca cagggacatt    1860
gctgctcgga atgttctggt gtcctcaaat gattgtgtaa aattaggaga ctttggatta    1920
tcccgatata tggaagatag tacttactac aaagcttcca aaggaaaatt gcctattaaa    1980
tggatggctc cagagtcaat caattttcga cgtttttacct cagctagtga cgtatggatg    2040
tttggtgtgt gtatgtggga gatactgatg catggtgtga agccttttca aggagtgaag    2100
aacaatgatg taatcggtcg aattgaaaat ggggaaagat taccaatgcc tcaaaattgt    2160
cctcctaccc tctacagcct tatgacgaaa tgctgggcct atgacccaag caggcggccc    2220
aggtttactg aacttaaagc tcagctcagc acaatcctgg aggaagagaa ggctcagcaa    2280
gaagagcgca tgaggatgga gtccagaaga caggccacag tgtcctggga ctccggaggg    2340
tctgatgaag caccgcccaa gcccagcaga ccggggttatc ccagtccgag gtccagcgaa    2400 ggatttatc ccagcccaca gcacatggta caaaccaatc attaccaggt ttctggctac    2460
cctggttcac atggaatcac agccatggct ggcagcatct atccaggtca ggcatctctt    2520
ttggaccaaa cagattcatg gaatcataga cctcaggaga tagcaatgtg gcagcccaat    2580
gtggaggact ctacagtatt ggacctgcga gggattgggc aagtgttgcc aacccatctg    2640
atggaagagc gtcaatccg acagcaacag gaaatggaag aagatcagcg ctggctggaa    2700
aaagaggaaa gatttctgaa acctgatgtg agactctctc gaggcagtat tgacagggag    2760
gatggaagtc ttcagggtcc gattggaaac caacatatat atcagcctgt gggtaaacca    2820
gatcctgcag ctcccaccaa agaaaccgcct cgccctggag ctcccggtca tctgggaagc    2880
cttgccagcc tcagcagccc tgctgacagc tacaacgagg gtgtcaagct tcagcccag    2940 gaaatcagcc cccctcctac tgccaacctg gaccggtcga atgataaggt gtacgagaat    3000
gtgacgggcc tggtgaaagc tgtcatcgag atgtccagta aaatccagcc agccccacca    3060
gaggagtatg tccctatggt gaaggaagtc ggcttggccc tgaggacatt attggccact    3120
gtggatgaga ccattcccct cctaccagcc agcacccacc gagagattga gatggcacag    3180
aagctattga actctgacct gggtgagctc atcaacaaga tgaaactggc ccagcagtat    3240
gtcatgacca gcctccagca agagtacaaa agcaaatgc tgactgctgc tcacgccctg    3300
gctgtggatg ccaaaaactt actcgatgtc attgaccaag caagactgaa atgcttggg    3360 cagacgagac cacactgagc ctcccctagg agcacgtctt gctaccctct tttgaagatg    3420
ttctctagcc ttccaccagc agcgaggaat taaccctgtg tcctcagtcg ccagcactta    3480
cagctccaac ttttttgaat gaccatctgg ttgaaaaatc tttctcatat aagtttaacc    3540
acactttgat ttgggttcat ttttttgtttt gtttttttca atcatgatat tcagaaaaat    3600
ccaggatcca aaatgtggcg tttttctaag aatgaaaatt atatgtaagc ttttaagcat    3660
catgaagaac aatttatgtt cacattaaga tacgttctaa agggggatgg ccaagggtg    3720 acatcttaat tcctaaacta ccttagctgc atagtggaag aggagagcat gaagcaaaga    3780
```

-continued

| | |
|---|---|
| attccaggaa acccaagagg ctgagaattc ttttgtctac catagaatta ttatccagac | 3840 |
| tggaattttt gtttgttaga acacccttca gttgcaatat gctaatccca ctttacaaag | 3900 |
| aatataaaag ctatattttg aagacttgag ttatttcaga aaaaactaca gcccttttg | 3960 |
| tcttacctgc cttttacttt cgtgtggata tgtgaagcat tgggtcggga actagctgta | 4020 |
| gaacacaact aaaaactcat gtcttttttc acagaataat gtgccagttt tttgtagcaa | 4080 |
| tgttatttct cttggaagca gaaatgcttt gtaccagagc acctccaaac tgcattgagg | 4140 |
| agaagttcca gaaccatccc cttttttccat ttttatataa tttataaaga aagattaaag | 4200 |
| ccatgttgac tattttacag ccactggagt taactaaccc ttccttgtat ctgtcttccc | 4260 |
| aggagagaat gaagcaaaac aggaatttgg ttttcttttg atgtccagtt acaccatcca | 4320 |
| ttctgttaat tttgaaaaaa tatacccctcc ctttagtttg ttgggggata taaattattc | 4380 |
| tcaggaagaa tataatgaac tgtacagtta ctttgaccta ttaaaaaggt gttaccagta | 4440 |
| aa | 4442 |

<210> SEQ ID NO 6
<211> LENGTH: 4453
<212> TYPE: DNA
<213> ORGANISM: Homo sapiens

<400> SEQUENCE: 6

| | |
|---|---|
| gaccactgtg agcccgcggc gtgaggcgtg ggaggaagcg cggctgctgt cgcccagcgc | 60 |
| cgccccgtcg tcgtctgcct tcgcttcacg gcgccgagcc gcggtccgag cagaactggg | 120 |
| gctcccttgc atcttccagt tacaaattca gtgccttctg cagttttcccc agagctcctc | 180 |
| aagaataacg gaagggagaa tatgacagat acctagcatc tagcaaaata atggcagctg | 240 |
| cttaccttga ccccaacttg aatcacacac caaattcgag tactaagact cacctgggta | 300 |
| ctggtatgga acgttctcct ggtgcaatgg agcgagtatt aaaggtcttt cattatttg | 360 |
| aaagcaatag tgagccaacc acctgggcca gtattatcag gcatggagat gctactgatg | 420 |
| tcagggcat cattcagaag atagtggaca gtcacaaagt aaagcatgtg gcctgctatg | 480 |
| gattccgcct cagtcacctg cggtcagagg aggttcactg gcttcacgtg gatatgggcg | 540 |
| tctccagtgt gagggagaag tatgagcttg ctcacccacc agaggagtgg aaatatgaat | 600 |
| tgagaattcg ttatttgcca aaaggatttc taaaccagtt tactgaagat aagccaactt | 660 |
| tgaatttctt ctatcaacag gtgaagagcg attatatgtt agagatagct gatcaagtgg | 720 |
| accaggaaat tgcttttgaag ttgggttgtc tagaaatacg gcgatcatac tgggagatgc | 780 |
| ggggcaatgc actagaaaag aagtctaact atgaagtatt agaaaaagat gttggtttaa | 840 |
| agcgattttt tcctaagagt ttactggatt ctgtcaaggc caaaacacta agaaaactga | 900 |
| tccaacaaac atttagacaa tttgccaacc ttaatagaga agaaagtatt ctgaaattct | 960 |
| ttgagatcct gtctccagtc tacagatttg ataaggaatg cttcaagtgt gctcttggtt | 1020 |
| caagctggat tatttcagtg gaactggcaa tcggcccaga agaaggaatc agttacctaa | 1080 |
| cggacaaggg ctgcaatccc acacatcttg ctgacttcac tcaagtgcaa accattcagt | 1140 |
| attcaaacag tgaagacaag gacagaaaag gaatgctaca actaaaaata gcaggtgcac | 1200 |
| ccgagcctct gacagtgacg gcaccatccc taaccattgc ggagaatatg gctgacctaa | 1260 |
| tagatgggta ctgccggctg gtgaatggaa cctcgcagtc attatcatc agacctcaga | 1320 |
| aagaaggtga acgggctttg ccatcaatac caaagttggc caacagcgaa aagcaaggca | 1380 |
| tgcggacaca cgccgtctct gtgtcagaaa cagatgatta tgctgagatt atagatgaag | 1440 |

```
aagatactta caccatgccc tcaaccaggg attatgagat tcaaagagaa agaatagaac    1500
ttggacgatg tattggagaa ggccaatttg gagatgtaca tcaaggcatt tatatgagtc    1560
cagagaatcc agctttggcg gttgcaatta aaacatgtaa aaactgtact tcggacagcg    1620
tgagagagaa atttcttcaa gaagccttaa caatgcgtca gtttgaccat cctcatattg    1680
tgaagctgat tggagtcatc acagagaatc ctgtctggat aatcatggag ctgtgcacac    1740
ttggagagct gaggtcattt ttgcaagtaa ggaaatacag tttggatcta gcatctttga    1800
tcctgtatgc ctatcagctt agtacagctc ttgcatatct agagagcaaa agatttgtac    1860
acagggacat tgctgctcgg aatgttctgg tgtcctcaaa tgattgtgta aaattaggag    1920
actttggatt atcccgatat atggaagata gtacttacta caaagcttcc aaaggaaaat    1980
tgcctattaa atggatggct ccagagtcaa tcaattttcg acgttttacc tcagctagtg    2040
acgtatggat gtttggtgtg tgtatgtggg agatactgat gcatggtgtg aagccttttc    2100
aaggagtgaa gaacaatgat gtaatcggtc gaattgaaaa tggggaaaga ttaccaatgc    2160
ctccaaattg tcctcctacc ctctacagcc ttatgacgaa atgctgggcc tatgacccca    2220
gcaggcggcc caggtttact gaacttaaag ctcagctcag cacaatcctg gaggaagaga    2280
aggctcagca agaagagcgc atgaggatgg agtccagaag acaggccaca gtgtcctggg    2340
actccggagg gtctgatgaa gcaccgccca agcccagcag accgggttat cccagtccga    2400
ggtccagcga aggattttat cccagcccac agcacatggt acaaaccaat cattaccagg    2460
tttctggcta ccctgggtca catggaatca cagccatggc tggcagcatc tatccaggtc    2520
aggcatctct tttggaccaa acagattcat ggaatcatag acctcaggag atagcaatgt    2580
ggcagcccaa tgtggaggac tctacagtat tggacctgcg agggattggg caagtgttgc    2640
caacccatct gatggaagag cgtctaatcc gacagcaaca ggaaatggaa gaagatcagc    2700
gctggctgga aaaagaggaa agatttctga acctgatgt gagactctct cgaggcagta    2760
ttgacaggga ggatggaagt cttcagggtc cgattggaaa ccaacatata tatcagcctg    2820
tgggtaaacc agatcctgca gctccaccaa agaaaccgcc tcgccctgga gctcccggtc    2880
atctgggaag ccttgccagc ctcagcagcc ctgctgacag ctacaacgag ggtgtcaagc    2940
ttcagcccca ggaaatcagc cccctccta ctgccaacct ggaccggtcg aatgataagg    3000
tgtacgagaa tgtgacgggc ctggtgaaag ctgtcatcga gatgtccagt aaaatccagc    3060
cagccccacc agaggagtat gtccctatgg tgaaggaagt cggcttggcc ctgaggacat    3120
tattggccac tgtggatgag accattcccc tcctaccagc cagcacccac cgagagattg    3180
agatggcaca gaagctattg aactctgacc tgggtgagct catcaacaag atgaaactgg    3240
cccagcagta tgtcatgacc agcctccagc aagagtacaa aaagcaaatg ctgactgctg    3300
ctcacgccct ggctgtggat gccaaaaact tactcgatgt cattgaccaa gcaagactga    3360
aaatgcttgg gcagacgaga ccacactgag cctcccctag gagcacgtct tgctaccctc    3420
ttttgaagat gttctctagc cttccaccag cagcgaggaa ttaaccctgt gtcctcagtc    3480
gccagcactt acagctccaa cttttttgaa tgaccatctg gttgaaaaat ctttctcata    3540
taagtttaac cacactttga tttgggttca ttttttgttt tgtttttttc aatcatgata    3600
ttcagaaaaa tccaggatcc aaaatgtggc gttttttcta agaatgaaaat tatatgtaag    3660 cttttaagca tcatgaagaa caatttatgt tcacattaag atacgttcta aaggggggatg    3720 gccaagggt gacatcttaa ttcctaaact accttagctg catagtggaa gaggagagca    3780
```

```
tgaagcaaag aattccagga aacccaagag gctgagaatt cttttgtcta ccatagaatt    3840
attatccaga ctggaatttt tgtttgttag aacacccttc agttgcaata tgctaatccc    3900
actttacaaa gaatataaaa gctatatttt gaagacttga gttatttcag aaaaaactac    3960
agcccttttt gtcttacctg cctttttactt tcgtgtggat atgtgaagca ttgggtcggg    4020
aactagctgt agaacacaac taaaaactca tgtctttttt cacagaataa tgtgccagtt    4080
ttttgtagca atgttatttc tcttggaagc agaaatgctt tgtaccagag cacctccaaa    4140
ctgcattgag gagaagttcc agaaccatcc cctttttcca tttttatata atttataaag    4200
aaagattaaa gccatgttga ctattttaca gccactggag ttaactaacc cttccttgta    4260
tctgtcttcc caggagagaa tgaagcaaaa caggaatttg gttttctttt gatgtccagt    4320
tacaccatcc attctgttaa ttttgaaaaa atatacccte cctttagttt gttgggggat    4380
ataaattatt ctcaggaaga atataatgaa ctgtacagtt actttgacct attaaaaagg    4440
tgttaccagt aaa                                                       4453

<210> SEQ ID NO 7
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence

<400> SEQUENCE: 7
ccaccugggc caguauuaut t                                               21

<210> SEQ ID NO 8
<211> LENGTH: 21
<212> TYPE: DNA
<213> ORGANISM: Artificial Sequence
<220> FEATURE:
<223> OTHER INFORMATION: Artificial primer
<220> FEATURE:
<221> NAME/KEY: misc_feature
<222> LOCATION: (1)..(21)
<223> OTHER INFORMATION: This is combined DNA/RNA sequence.

<400> SEQUENCE: 8
auaauacugg cccagguggt t                                               21

<210> SEQ ID NO 9
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 9
uuuuccgaac gugucacgut t                                               21

<210> SEQ ID NO 10
<211> LENGTH: 21
<212> TYPE: DNA
<213> ORGANISM: Artificial Sequence
<220> FEATURE:
<223> OTHER INFORMATION: Synthetic primer
```

```
<220> FEATURE:
<221> NAME/KEY: misc_feature
<222> LOCATION: (1)..(21)
<223> OTHER INFORMATION: This is combined DNA/RNA sequence.

<400> SEQUENCE: 10
acgugacacg uucggagaat t                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetic primer

<400> SEQUENCE: 11
ccgatagcag gtgaactcga a                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetic primer

<400> SEQUENCE: 12
cagagtggat atcacgtgga a                                              21

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
tcggaatcca aggtgtaggg                                                20

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
tggcttttct ctttgcctcg                                                20

<210> SEQ ID NO 15
<211> LENGTH: 23
<212> TYPE: DNA
<213> ORGANISM: Artificial Sequence
<220> FEATURE:
<223> OTHER INFORMATION: Synthetic primer

<400> SEQUENCE: 15
catgtctctc atcgtcctgg cca                                            23

<210> SEQ ID NO 16
<211> LENGTH: 22
<212> TYPE: DNA
<213> ORGANISM: Artificial Sequence
<220> FEATURE:
<223> OTHER INFORMATION: Synthetic primer

<400> SEQUENCE: 16
```
cacgatggaa gaggcaatgg ca                                                    22

<210> SEQ ID NO 17
<211> LENGTH: 22
<212> TYPE: DNA
<213> ORGANISM: Artificial Sequence
<220> FEATURE:
<223> OTHER INFORMATION: Synthetic primer

<400> SEQUENCE: 17
cacgatggaa gaggcaatgg ca                                                    22

<210> SEQ ID NO 18
<211> LENGTH: 3920
<212> TYPE: DNA
<213> ORGANISM: Homo sapiens

<400> SEQUENCE: 18 agggcagaa gttgcgcgca ggccggcggg cgggagcgga caccgaggcc ggcgtgcagg        60
cgtgcgggtg tgcgggagcc gggctcgggg ggatcggacc gagagcgaga agcgcggcat       120
ggagctccag gcagcccgcg cctgcttcgc cctgctgtgg ggctgtgcgc tggccgcggc       180
cgcggcggcg cagggcaagg aagtggtact gctggacttt gctgcagctg gaggggagct       240
cggctggctc acacacccgt atggcaaagg gtgggacctg atgcagaaca tcatgaatga       300
catgccgatc tacatgtact ccgtgtgcaa cgtgatgtct ggcgaccagg acaactggct       360
ccgcaccaac tgggtgtacc gaggagaggc tgagcgtatc ttcattgagc tcaagtttac       420
tgtacgtgac tgcaacagct ccctggtgg cgccagctcc tgcaaggaga ctttcaacct       480
ctactatgcc gagtcggacc tggactacgg caccaacttc cagaagcgcc tgttcaccaa       540
gattgacacc attgcgcccg atgagatcac cgtcagcagc gacttcgagg cacgccacgt       600
gaagctgaac gtggaggagc gctccgtggg gccgctcacc cgcaaaggct tctacctggc       660
cttccaggat atcggtgcct gtgtggcgct gctctccgtc cgtgtctact acaagaagtg       720
ccccgagctg ctgcagggcc tgcccacttc cctgagacc atcgccggct ctgatgcacc       780
ttccctggcc actgtggccg gcacctgtgt ggaccatgcc gtggtgccac cgggggggtga       840 agagccccgt atgcactgtg cagtggatgg cgagtggctg gtgcccattg gcagtgcct        900 gtgccaggca ggctacgaga aggtggagga tgcctgccag gcctgctcgc ctggattttt      960
taagtttgag gcatctgaga gcccctgctt ggagtgccct gagcacacgc tgccatcccc      1020
tgagggtgcc acctcctgcg agtgtgagga aggcttcttc cggcacctc aggacccagc      1080 gtcgatgcct tgcacacgac ccccctccgc cccacactac ctcacagccg tgggcatggg      1140
tgccaaggtg gagctgcgct ggacgccccc tcaggacagc gggggccgcg aggacattgt      1200
ctacagcgtc acctgcgaac agtgctggcc cgagtctggg gaatgcgggc cgtgtgaggc      1260
cagtgtgcgc tactcggagc ctcctcacgg actgacccgc accagtgtga cagtgagcga      1320
cctggagccc cacatgaact acaccttcac cgtggaggcc cgcaatggcg tctcaggcct      1380
ggtaaccagc cgcagcttcc gtactgccag tgtcagcatc aaccagacag agcccccaa       1440 ggtgaggctg gagggccgca gcaccacctc gcttagcgtc cctgagca tcccccgcc        1500 gcagcagagc cgagtgtgga agtacgaggt cacttaccgc aagaagggag actccaacag      1560
ctacaatgtg cgccgcaccg agggttctc cgtgaccctg gacgacctgg ccccagacac      1620
cacctacctg gtccaggtgc aggcactgac gcaggagggc caggggccg gcagcaaggt      1680 gcacgaattc cagacgctgt ccccggaggg atctggcaac ttggcggtga ttggcggcgt     1740

```
ggctgtcggt gtggtcctgc ttctggtgct ggcaggagtt ggcttcttta tccaccgcag   1800
gaggaagaac cagcgtgccc gccagtcccc ggaggacgtt tacttctcca agtcagaaca   1860
actgaagccc ctgaagacat acgtggaccc ccacacatat gaggacccca accaggctgt   1920
gttgaagttc actaccgaga tccatccatc ctgtgtcact cggcagaagg tgatcggagc   1980
aggagagttt ggggaggtgt acaagggcat gctgaagaca tcctcgggga agaaggaggt   2040
gccggtggcc atcaagacgc tgaaagccgg ctacacagag aagcagcgag tggacttcct   2100
cggcgaggcc ggcatcatgg gccagttcag ccaccacaac atcatccgcc tagagggcgt   2160
catctccaaa tacaagccca tgatgatcat cactgagtac atggagaatg ggccctgga   2220 caagttcctt cgggagaagg atggcgagtt cagcgtgctg cagctggtgg catgctgcg   2280 gggcatcgca gctggcatga agtacctggc caacatgaac tatgtgcacc gtgacctggc   2340
tgcccgcaac atcctcgtca cagcaacct ggtctgcaag gtgtctgact ttggcctgtc   2400
ccgcgtgctg gaggacgacc ccgaggccac ctacaccacc agtggcggca agatccccat   2460
ccgctggacc gccccggagg ccatttccta ccggaagttc acctctgcca gcgacgtgtg   2520
gagctttggc attgtcatgt gggaggtgat gacctatggc gagcggccct actgggagtt   2580
gtccaaccac gaggtgatga agccatcaa tgatggcttc cggctcccca cacccatgga   2640
ctgcccctcc gccatctacc agctcatgat gcagtgctgg cagcaggagc gtgcccgccg   2700
ccccaagttc gctgacatcg tcagcatcct ggacaagctc attcgtgccc ctgactccct   2760
caagaccctg gctgactttg accccgcgt gtctatccgg ctccccagca cgagcggctc   2820 ggaggggtg cccttccgca cggtgtccga gtggctggag tccatcaaga tgcagcagta   2880
tacggagcac ttcatggcgg ccggctacac tgccatcgag aaggtggtgc agatgaccaa   2940
cgacgacatc aagaggattg gggtgcggct gcccggccac cagaagcgca tcgcctacag   3000
cctgctggga ctcaaggacc aggtgaacac tgtgggatc cccatctgag cctcgacagg   3060
gcctggagcc ccatcggcca agaatacttg aagaaacaga gtggcctccc tgctgtgcca   3120
tgctgggcca ctggggactt tatttatttc tagttctttc ctcccctgc aacttccgct   3180 gaggggtctc ggatgacacc ctggcctgaa ctgaggagat gaccagggat gctgggctgg   3240
gccctctttc cctgcgagac gcacacagct gagcacttag caggcaccgc cacgtcccag   3300
catccctgga gcaggagccc cgccacagcc ttcggacaga catataggat attcccaagc   3360
cgaccttccc tccgccttct cccacatgag gccatctcag gagatggagg gcttggccca   3420
gcgccaagta aacagggtac ctcaagcccc atttcctcac actaagaggg cagactgtga   3480
acttgactgg gtgagaccca aagcggtccc tgtccctcta gtgccttctt tagaccctcg   3540
ggccccatcc tcatccctga ctggccaaac ccttgctttc ctgggccttt gcaagatgct   3600
tggttgtgtt gaggtttta aatatatatt ttgtactttg tggagaaaat gtgtgtgtgt   3660 ggcaggggc cccgccaggg ctgggacag agggtgtcaa acattcgtga gctgggact   3720 cagggaccgg tgctgcagga gtgtcctgcc catgcccag tcggccccat ctctcatcct   3780
tttggataag tttctattct gtcagtgtta aagattttgt tttgttggac atttttttcg   3840
aatcttaatt tattatttt tttatattta ttgttagaaa atgacttatt tctgctctgg   3900
aataaagttg cagatgattc                                              3920
```

<210> SEQ ID NO 19
<211> LENGTH: 1242
<212> TYPE: DNA

```
<213> ORGANISM: Homo sapiens

<400> SEQUENCE: 19
atggggcaac ccgggaacgg cagcgccttc ttgctggcac ccaatggaag ccatgcgccg      60
gaccacgacg tcacgcagca aagggacgag gtgtgggtgg tgggcatggg catcgtcatg     120
tctctcatcg tcctggccat cgtgtttggc aatgtgctgg tcatcacagc cattgccaag     180
ttcgagcgtc tgcagacggt caccaactac ttcatcactt cactggcctg tgctgatctg     240
gtcatgggcc tggcagtggt gcccttcggg gccgcccata ttcttatgaa aatgtggact     300
tttggcaact tctggtgcga gttttggact tccattgatg tgctgtgcgt cacggccagc     360
attgagaccc tgtgcgtgat cgcagtggat cgctactttg ccattacttc acctttcaag     420
taccagagcc tgctgaccaa gaataaggcc cgggtgatca ttctgatggt gtggattgtg     480
tcaggcctta cctccttctt gcccattcag atgcactggt accgggccac ccaccaggaa     540
gccatcaact gctatgccaa tgagacctgc tgtgacttct tcacgaacca agcctatgcc     600
attgcctctt ccatcgtgtc cttctacgtt ccccctggtga tcatggtctt cgtctactcc     660
agggtctttc aggaggccaa aaggcagctc cagaagattg acaaatctga gggccgcttc     720
catgtccaga accttagcca ggtggagcag gatgggcgga cggggcatgg actccgcaga     780
tcttccaagt tctgcttgaa ggagcacaaa gccctcaaga cgttaggcat catcatgggc     840
actttcaccc tctgctggct gcccttcttc atcgttaaca ttgtgcatgt gatccaggat     900
aacctcatcc gtaaggaagt ttacatcctc ctaaattgga taggctatgt caattctggt     960
ttcaatcccc ttatctactg ccggagccca gatttcagga ttgccttcca ggagcttctg    1020
tgcctgcgca ggtcttcttt gaaggcctat gggaatggct actccagcaa cggcaacaca    1080
ggggagcaga gtggatatca cgtggaacag gagaaagaaa ataaactgct gtgtgaagac    1140
ctcccaggca cggaagactt tgtgggccat caaggtactg tgcctagcga taacattgat    1200
tcacaaggga ggaattgtag tacaaatgac tcactgctgt aa                       1242
```

DELIVERY OF SIRNA BY NEUTRAL LIPID COMPOSITIONS

This application is a national phase application under 35 U.S.C. §371 of International Application No. PCT/US2006/014501 filed 17 Apr. 2006, which claims priority to U.S. Provisional Patent Application Ser. No. 60/671,641 filed Apr. 15, 2005, both of which are hereby incorporated by reference in their entirety.

The government owns rights in the present invention pursuant to grant number #W81XWH-04-1-0227 from the Department of Defense and grant CA10929801 from the National Cancer Institute.

SEQUENCE LISTING

Background of the Invention

I. Field of the Invention

The present invention relates generally to the fields of molecular biology, medicine, oncology, and delivery of therapeutic compounds. More particularly, it concerns the delivery of inhibitory nucleic acids, including siNA (e.g., a siRNA) via neutral lipid compositions or liposomes.

II. Description of Related Art

Short interfering RNA (siRNA) is well known in the art, but delivery of siRNA in vivo has proven to be very difficult, thus limiting the therapeutic potential of siRNA. Since its description in *C. elegans* (Fire, 1998) and mammalian cells (Elbashir et al., 2001), use of siRNA as a method of gene silencing has rapidly become a powerful tool in protein function delineation, gene discovery, and drug development (Hannon, 2004). The promise of specific RNA degradation has also generated much excitement for possible use as a therapeutic modality, but in vivo siRNA delivery has proven difficult (Ryther, 2005).

Delivery methods that are effective for other nucleic acids are not necessarily effective for siRNA (Hassani, 2005). Therefore, most studies using siRNA in vivo involve manipulation of gene expression in a cell line prior to introduction into an animal model (Brummelkamp, 2002; Yang, 2003), or incorporation of siRNA into a viral vector (Xia, 2002; Devroe, 2004). Delivery of "naked" siRNA in vivo has been restricted to site-specific injections or through high-pressure means that are not clinically practical. One study that showed in vivo uptake and targeted downregulation of an endogenous protein by an siRNA after normal systemic dosing required chemical modification of the siRNA (Soutschek, 2004); however, this chemical modification has an unknown toxicity and may result in significant toxicity to a subject in vivo. Further this chemical modification may affect siRNA activity and/or longevity.

Liposomes have been used previously for drug delivery (e.g., delivery of a chemotherapeutic). Liposomes (e.g., cationic liposomes) are described in PCT publications WO02/100435A1, WO03/015757A1, and WO04029213A2; U.S. Pat. Nos. 5,962,016, 5,030,453, and 6,680,068; and U.S. Patent Application 2004/0208921, all of which are hereby incorporated by reference in their entirety without disclaimer. A process of making liposomes is also described in WO04/002453A1. Furthermore, neutral lipids have been incorporated into cationic liposomes (e.g., Farhood et al., 1995).

Cationic liposomes have been used to deliver siRNA to various cell types (Sioud and Sorensen, 2003; U.S. Patent Application 2004/0204377; Duxbury et al., 2004; Donze and Picard, 2002). However, it is not clear if or to what degree neutral liposomes may be used deliver siRNA to a cell.

Neutral liposomes have been tested to a limited degree. Miller et al. (1998) evaluated the uptake of neutral unilamellar liposomes; however, this work observed that cationic liposomes are taken up by cells more efficiently than neutral liposomes, thus teaching away from the idea that neutral liposomes may be more effective than cationic liposomes. Neutral liposomes were used to deliver therapeutic antisense oligonucleotides in U.S. Patent Application 2003/0012812. However, it is not clear if or to what degree neutral liposomes may be used to deliver siRNA.

SUMMARY OF THE INVENTION

The present invention provides compositions and methods for delivery of an inhibitory nucleic acid, including short interfering ribonucleic acids (siRNA) or nucleic acids that encode siRNAs. In certain embodiments the inhibitory nucleic acid can be delivered to a cell via a non-charged (neutral) liposome. The inventors have discovered that non-charged liposomes may be used to efficiently deliver an inhibitory nucleic acid such as a siNA or a siRNA to cells in vivo. In particular aspects, siNA delivery using neutral liposomes results in significant (~10 fold) improvement in delivery as compared with cationic liposomes in vivo. It has also been identified that the methods of the present invention may be particularly suited for the treatment of cancer or other hyperplastic conditions.

Embodiments of the present invention relate to compositions comprising a siNA component and a lipid component comprising one or more phospholipids, wherein the lipid component has an essentially neutral charge. In certain aspects the lipid component may be in the form of a liposome. The siNA (e.g., a siRNA) may be encapsulated in the liposome or lipid component, but need not be. Encapsulate refers to the lipid or liposome forming an impediment to free diffusion into solution by an association with or around an agent of interest, e.g., a liposome may encapsulate an agent within a lipid layer or within an aqueous compartment inside or between lipid layers. In certain embodiments, the composition is comprised in a pharmaceutically acceptable carrier. The pharmaceutically acceptable carrier may be formulated for administration to a human subject or patient.

In certain embodiments, the lipid component has an essentially neutral charge because it comprises a neutral phospholipid or a net neutral charge. In certain aspects a neutral phospholipid may be a phosphatidylcholine, such as DOPC, egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), palmitoyloeoyl phosphatidylcholine ("POPC"), lysophosphatidylcholine, or dilinoleoylphosphatidylcholine. In other aspects the neutral phospholipid can be a phosphatidylethanolamine, such as dioleoylphosphatidylethanolamine ("DOPE"), distearoylphophatidylethanolamine ("DSPE"), dimyristoyl phosphatidylethanolamine ("DMPE"), dipalmitoyl phosphatidylethanolamine ("DPPE"), palmitoyloeoyl phosphatidylethanolamine ("POPE"), or lysophosphatidylethanolamine. In certain embodiments, the phospholipid component can comprise 1, 2, 3, 4, 5, 6, 7, 8, or more kinds or types of neutral phospholipid. In other embodiments, a phospholipid component can comprise 2, 3, 4, 5, 6 or more kinds or type of neutral phospholipids.

In certain embodiments, a lipid component can have an essentially neutral charge because it comprises a positively charged lipid and a negatively charged lipid. The lipid component may further comprise a neutrally charged lipid(s) or phospholipid(s). The positively charged lipid may be a positively charged phospholipid. The negatively charged lipid may be a negatively charged phospholipid. The negatively charged phospholipid may be a phosphatidylserine, such as dimyristoyl phosphatidylserine ("DMPS"), dipalmitoyl phosphatidylserine ("DPPS"), or brain phosphatidylserine ("BPS"). The negatively charged phospholipid may be a phosphatidylglycerol, such as dilauryloylphosphatidylglycerol ("DLPG"), dimyristoylphosphatidylglycerol ("DMPG"), dipalmitoylphosphatidylglycerol ("DPPG"), distearoylphosphatidylglycerol ("DSPG"), or dioleoylphosphatidylglycerol ("DOPG"). In certain embodiments, the composition further comprises cholesterol or polyethyleneglycol (PEG). In certain embodiments, a phospholipid is a naturally-occurring phospholipid. In other embodiments, a phospholipid is a synthetic phospholipid.

An inhibitory nucleic acid (siNA) includes a siRNA or shRNA (short hairpin RNA), a ribozyme, or an antisense nucleic acid molecule that specifically hybridize to a nucleic acid molecule encoding a target protein or regulating the expression of the target protein. "Specific hybridization" means that the siRNA, shRNA, ribozyme or antisense nucleic acid molecule hybridizes to the targeted nucleic acid molecule and regulates its expression. Preferably, "specific hybridization" also means that no other genes or transcripts are affected. A siNA can be a double-stranded nucleic acid and may comprise 18, 19, 20, 21, 22, 23, 24, 25, 26, 27, 28, 29, 30, 35, 40, 50, 100 to 18, 20, 21, 22, 23, 24, 25, 26, 27, 28, 29, 30, 40, 50, 100, 200, 300, 500 or more nucleobases or nucleobase pairs. In particular aspects the double stranded nucleic acid can comprise 18 to 30, 19 to 25, 20 to 23, or 21 contiguous nucleobases or nucleobase pairs. In certain embodiments, the siNA inhibits the translation of a gene that promotes growth of a cancerous or pre-cancerous or hyperplastic mammalian cell (e.g., a human cell). An siNA may induce apoptosis in the cell, and/or inhibit the translation of an oncogene or other target gene. The gene may be EphA2, focal adhesion kinase (FAK), or $\beta2$ adrenergic receptor ($\beta_2AR$). In certain embodiments, the siNA component comprises a single species of siRNA. In other embodiments, the siNA component comprises a 2, 3, 4 or more species of siRNA that target 1, 2, 3, 4, or more genes. The composition may further comprise a chemotherapeutic or other anti-cancer agent, which may or may not be encapsulated in a lipid component or liposome of the invention. In further embodiments, the nucleic acid component is encapsulated within the liposome or lipid component.

Another aspect of the present invention involves methods for delivering siNA to a cell comprising contacting the cell with a neutral lipid composition of the invention. The methods will provide an inventive composition in an effective amount. An effective amount is an amount of therapeutic component that attenuates, slows, reduces or eliminates a cell, condition or disease state in a subject. The cell may be comprised in a subject or patient, such as a human. The method may further comprise a method of treating cancer or other hyperplastic condition. The cancer may have originated in the bladder, blood, bone, bone marrow, brain, breast, colon, esophagus, gastrointestine, gum, head, kidney, liver, lung, nasopharynx, neck, prostate, skin, stomach, testis, tongue, or uterus. In certain embodiments, the cancer is ovarian cancer. In certain embodiments, the method further comprises a method of treating a non-cancerous disease or hyperplastic condition. The cell may be a pre-cancerous or a cancerous cell. In certain embodiments, the compositions and methods inhibit the growth of the cell, induce apoptosis in the cell, and/or inhibit the translation of an oncogene. The siNA may inhibit the translation of a gene that is overexpressed in the cancerous cell. The gene may be EphA2, focal adhesion kinase (FAIL), and/or $\beta2$ adrenergic receptor ($\beta2AR$).

In certain embodiments, the methods of the invention further comprise administering an additional therapy to the subject. The additional therapy may comprise administering a chemotherapeutic (e.g., paclitaxel or docetaxel), a surgery, a radiation therapy, and/or a gene therapy. In certain aspects the chemotherapy is docetaxel, paclitaxel, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristin, vinblastin, methotrexate, or combinations thereof. In certain embodiments the chemotherapy is a taxane such as docetaxal or paclitaxel. The chemotherapy can be delivered before, during, after, or combinations thereof relative to a neutral lipid composition of the invention. A chemotherapy can be delivered within 0, 1, 5, 10, 12, 20, 24, 30, 48, or 72 hours or more of the neutral lipid composition. The neutral lipid composition, the second anti-cancer therapy, or both the neutral lipid composition and the anti-cancer therapy can be administered intratumorally, intravenously, intraperitoneally, orally or by various combinations thereof.

The use of the word "a" or "an" when used in conjunction with the term "comprising" in the claims and/or the specification may mean "one," but it is also consistent with the meaning of "one or more," "at least one," and "one or more than one." As used herein "another" may mean at least a second or more.

It is contemplated that any embodiment discussed in this specification can be implemented with respect to any method or composition of the invention, and vice versa. Furthermore, compositions of the invention can be used to achieve the methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-1G. In vivo siRNA distribution to HeyA8 intraperitoneal tumor tissue after a single siRNA dose. (A) H&E stain (original magnification ×200) of HeyA8 intraperitoneal tumor. (B) Autofluorescence in tumor 48 hrs after IV administration of 5 µg non-fluorescent control siRNA. Tumors were harvested and frozen in OCT media, slides were fixed in acetone, and exposed to Hoescht to stain nuclei blue before viewing. (C) Fluorescent emission of Alexa-555-siRNA encapsulated in DOPC within the same tumor shown in (A) is seen as red punctuations within the cytoplasm. Samples were processed identically to those in (B). Samples were processed as above and additionally exposed to anti-f4/80 antibody to detect scavenging macrophages, and Alexa-488-tagged secondary antibody. Alexa-555-siRNA is seen in both tumor cells and surrounding macrophages. (E) 30 µm sections were examined with confocal microscopy. Photographs taken every 1 µm were stacked and examined from the lateral aspect. Fluorescent siRNA is noted throughout the section, and high magnification 3-dimensional construction shows all siRNA is perinuclear (not shown). Fluorescent Alexa488-tagged secondary antibody (green) is trapped on the surface, too large to penetrate tissue. Nuclei are labeled with Hoescht (blue). (F) Tumors collected from mice given Alexa-555-siRNA complexed in DOTAP were stained with CD31-Alexa488 (green) to identify endothelial cells. siRNA is seen to complex near the vasculature with poor parenchymal tumor uptake. (G) Tumors collected after administration of a single high-dose (10 µg) siRNA without transfection reagent are seen to rarely take up siRNA, but uptake is distributed throughout the cytoplasm. (B-D) and (F-G) shown at original magnification ×400.

FIGS. 2A-2I: In vivo siRNA distribution to major organs. SiRNA uptake by the liver (A, B, & C), kidney (D, E, & F), and lung (G, H, & I) are shown. Histological sections from these organs were collected after intravenous injection of 5 µg DOPC-siRNA. (A, D, and G) H&E staining of these organs. (B, E, and H) Alexa-555-siRNA (red) within the organ parenchymal cells. Co-staining to identify nuclei (blue) and f4/80 (green) distinguishes macrophages from organ cells. In the kidney, siRNA is noted in both tubules and the glomerulus (lower aspect of (E)). (C, F, and I) Show the natural autofluorescence of each tissue, after a single IV injection of nonfluorescent siRNA. All pictures taken at original magnification ×400.

FIGS. 3A-3D: In vivo downregulation of EphA2 by siRNA. (A) Western blot of lysate from orthotopic tumors collected 48 hrs after a single administration of control siRNA (lanes 1-2) or EphA2-targeting (lanes 3-5) siRNA, each complexed within DOPC. To control for sampling error of the tumor, lanes 1a and 1b are separate preparations from the same tumor treated with control siRNA. Similarly, lanes 5a and 5b are separate preparations from the same tumor treated with EphA2-targeting siRNA. Lanes 2, 3, and 4 are from additional tumor-bearing mice treated with control or EphA2-targeting siRNA/DOPC. Adjacent sections were stained by H&E to confirm presence of tumor. (B) Immunohistochemical staining for EphA2 of tissue treated with control siRNA/DOPC. The typical cobblestoning appearance of this overexpressed (Thaker et al., 2004) membrane-bound protein is noted. (C) IHC 48 hrs after a single treatment of EphA2-targeting siRNA without a transfection agent ("naked") is shown, and had no detectable affect on EphA2 expression. (D) Treatment of EphA2-targeting siRNA encapsulated within DOPC effectively downregulated EphA2 expression 48 hrs after a single dose. EphA2 expression is restored 1 week after a single treatment (not pictured). FIGS. 3B-3D taken at original magnification ×400.

FIGS. 4A-4B: Therapeutic efficacy of siRNA-mediated EphA2 downregulation. Nude mice were injected intraperitoneally with $2.5 \times 10^5$ HeyA8 cells (A) or $1.0 \times 10^6$ SKOV3ip1 cells (B) and randomly allocated to one of 5 groups, with therapy beginning one week after cell injection: 1) empty DOPC liposomes, 2) control siRNA in DOPC, 3) EphA2-targeting siRNA in DOPC, 4) paclitaxel plus control siRNA in DOPC, or 5) paclitaxel plus EphA2 siRNA in DOPC. SiRNA/liposomes were injected twice per week at a dose of 150 µg/kg siRNA. 100 µg paclitaxel (or vehicle in groups 1-3) was injected intraperitoneally once per week. When control animals began to appear moribund from tumor volume (4-5 weeks after cell injection), all animals in an experiment were sacrificed, and mouse weight, tumor weight, and tumor location were recorded. EphA2-targeting siRNA alone diminished tumor growth compared to control siRNA (HeyA8 p=0.155, SKOV3ip1 p=0.020), and the addition of EphA2-targeting siRNA to paclitaxel reduced growth by 67-82% compared to control siRNA plus paclitaxel (p<0.003 for both lines). Data for HeyA8 represent the average of two identically performed experiments, which individually gave the same statistical conclusions as the combination.

FIGS. 15A-15C. (A) Mouse restraint system utilized for physical immobilization to cause chronic stress. Empty mouse restraint system is shown on left. Mice are placed in individual slots (middle) and the levers are adjusted for immobilization stress (right). Quantification of tissue norepinephrine (B) and corticosterone (C) levels from ovaries, spleen, and omentum in nude mice using HPLC tandem mass spectrometry on day 1, 3, 7, and 14 after stress. Results represent the mean±s.e.m.; n=3 for each time point. Solid bars, restrained mice; open bars control mice.

DESCRIPTION OF ILLUSTRATIVE EMBODIMENTS

Figures 5A, 5B:
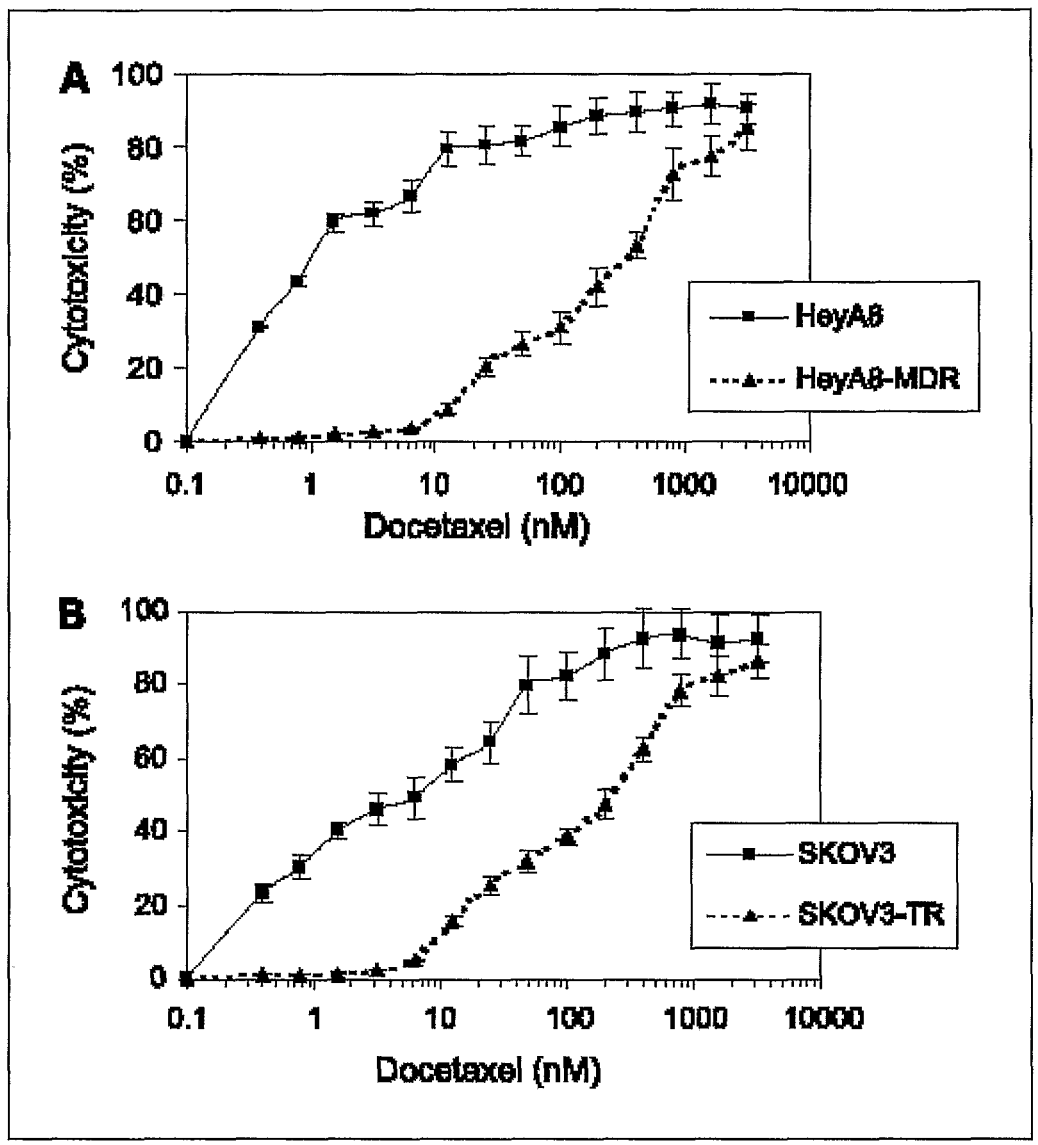
FIGS. 5A-5B. Effect of docetaxel on ovarian cancer cell growth: (A) HeyA8 and HeyA8-MDR or (B) SKOV3 or SKOV3-TR cells were plated in 96-well plates and subsequently incubated with increasing concentrations of docetaxel for 96 hours, and cell viability was determined. Points, mean of three independent experiments; bars, SE.

The inventors have developed additional gene silencing compositions and methods for use as an in vivo therapeutic, particularly with respect to using inhibitory nucleic acids such as short interfering RNA (siRNA). Aspects of the invention utilize a neutral lipid composition for delivery of inhibitors of gene expression. In particular aspects the lipid composition comprises 1,2-Dioleoyl-sn-Glycero-3-phosphatidylcholine (DOPC). Embodiments include silencing or reducing expression/translation of genes that play a role in cancer cell survival, cancer cell growth and/or cancer cell metastasis, for example ovarian cancer cells. In certain aspects the genes to be targeted include, but are not limited to focal adhesion kinase (FAK) gene, EphA2 gene, and/or β2AR gene. Still further aspects of the invention include combining the inhibitor of gene expression therapy with one or more anti-cancer agent(s). Anti-cancer agents include chemotherapy, radiotherapy, immunotherapy, gene therapy and the like. In particular embodiments, inhibitors of gene expression are combined with docetaxel or paclitaxel therapy.

The present invention provides compositions and methods for delivery of an inhibitor of gene expression (an agent that effects RNA interference, e.g., siRNA) to a cell via a lipid composition, in certain aspects a lipid composition with a net charge of about zero, i.e., a neutral lipid composition. In certain embodiments the lipid composition is a non-charged liposome. The inventors have discovered that non-charged liposomes can be used to efficiently deliver a siNA (e.g., an siRNA) to cells in vivo; further, delivery of siNA via neutral liposomes resulted in a significant (~10 fold) improvement in delivery as compared with cationic liposomes in vivo. These methods may be effectively used to treat a cancer.

I. Therapeutic Gene Silencing

Since the discovery of RNAi by Fire and colleagues in 19981, the biochemical mechanisms have been rapidly characterized. Long double stranded RNA (dsRNA) is cleaved by Dicer, which is an RNAaseIII family ribonuclease. This process yields siRNAs of ~21 nucleotides in length. These siRNAs are incorporated into a multiprotein RNA-induced silencing complex (RISC) that is guided to target mRNA. RISC cleaves the target mRNA in the middle of the complementary region. In mammalian cells, the related microRNAs (miRNAs) are found that are short RNA fragments (~22 nucleotides). mRNAs are generated after Dicer-mediated cleavage of longer (~70 nucleotide) precursors with imperfect hairpin RNA structures. The miRNA is incorporated into a miRNA-protein complex (miRNP), which leads to translational repression of target mRNA.

A. Delivery of siRNA or a Nucleic Acid Encoding Same

To improve the effectiveness of siRNA-mediated gene silencing, guidelines for selection of target sites on mRNA have been developed for optimal design of siRNA (Soutschek et al., 2004; Wadhwa et al., 2004). These strategies may allow for rational approaches for selecting siRNA sequences to achieve maximal gene knockdown. To facilitate the entry of siRNA into cells and tissues, a variety of vectors including plasmids and viral vectors such as adenovirus, lentivirus, and retrovirus have been used (Wadhwa et al., 2004). While many of these approaches are successful for in vitro studies, in vivo delivery poses additional challenges based on the complexity of the tumor microenvironment.

Liposomes are a form of nanoparticles that are attractive carriers for delivering a variety of drugs into the diseased tissue. Optimal liposome size depends on the tumor target. In tumor tissue, the vasculature is discontinuous, and pore sizes vary from 100 to 780 nm (Siwak et al., 2002). By comparison, pore size in normal vascular endothelium is <2 nm in most tissues, and 6 nm in post-capillary venules. Most liposomes are 65-125 nm in diameter. Negatively charged liposomes were believed to be more rapidly removed from circulation than neutral or positively charged liposomes; however, recent studies have indicated that the type of negatively charged lipid affects the rate of liposome uptake by the reticuloendothelial system (RES). For example, liposomes containing negatively charged lipids that are not sterically shielded (phosphatidylserine, phosphatidic acid, and phosphatidylglycerol) are cleared more rapidly than neutral liposomes. Interestingly, cationic liposomes (1,2-dioleoyl-3-trimethylammonium-propane [DOTAP]) and cationic-liposome-DNA complexes are more avidly bound and internalized by endothelial cells of angiogenic blood vessels via endocytosis than anionic, neutral, or sterically stabilized neutral liposomes (Thurston et al., 1998; Krasnici et al., 2003). Cationic liposomes may not be ideal delivery vehicles for tumor cells because surface interactions with the tumor cells create an electrostatically derived binding-site barrier effect, inhibiting further association of the delivery systems with tumor spheroids (Kostarelos et al., 2004). However, neutral liposomes appear to have better intratumoral penetration. Toxicity with specific liposomal preparations has also been a concern. Cationic liposomes elicit dose-dependent toxicity and pulmonary inflammation by promoting release of reactive oxygen intermediates, and this effect is more pronounced with multivalent cationic liposomes than monovalent cationic liposomes such as DOTAP (Dokka et al., 2000). Neutral and negative liposomes do not appear to exhibit lung toxicity (Guitierrez-Puente et al., 1999). Cationic liposomes, while efficiently taking up nucleic acids, have had limited success for in vivo gene downregulation, perhaps because of their stable intracellular nature and resultant failure to release siRNA contents.

The inventors have selected lipids with neutral or lipid compositions with a neutalized charge, e.g., 1,2-dioleoyl-sn-glycero-3-phosphatidylcholine (DOPC), because of the neutral properties and success in delivering antisense oligonucleotides in vivo. The inventors have recently demonstrated highly-efficient and efficacious in vivo siRNA delivery using neutral liposomes in an orthotopic model of advanced ovarian cancer (Landen et al., 2005, which is incorporated herein by reference in its entirety). For example, intravenous injection of the DOPC-siRNA complex allowed a significantly greater degree of siRNA deposition into the tumor parenchyma than either delivery with cationic (positively charged) liposomes (DOTAP) or unpackaged "naked" siRNA. While the DOPC formulation delivered siRNA to over 30% of cells in the tumor parenchyma, naked siRNA was delivered only to about 3% of cells, and DOTAP delivered siRNA only to tumor cells immediately adjacent to the vasculature. In subsequent studies, the inventors have demonstrated that use of DOPC-siRNA specific to the EphA2 receptor tyrosine kinase mRNA downregulated protein expression in the tumor, and reduced tumor growth of both the HeyA8 and SKOV3ip1 ovarian cancer cell lines. When used alone, EphA2 downregulation led to a reduction in tumor growth of 30-50%, compared to a non-specific siRNA. In combination with paclitaxel, there was even greater reduction in growth, by up to 95% compared to control tumors. Combination therapy was 60-70% more effective than paclitaxel alone. Treatment was also effective in reducing ascites formation and the total number of nodules formed, but did not have an effect on the incidence of tumor formation (Landen et al., 2005). No obvious toxicities were observed in the DOPC-siRNA treated animals. Moreover, examination of multiple organs including the liver, kidney, breast, lung, and brain revealed no histologic toxicities. A slight increase in the splenic white pulp was noted in all siRNA treated animals, which may be indicative of a general inflammatory response.

While "targeted" cancer therapies are now being incorporated into cancer therapeutics for upfront and salvage therapies, problems related to toxicity have remained a significant clinical issue (Ellis et al., 2005). Use of siRNA for targeting genes that have differential overexpression tumors and little to no expression in normal healthy adult tissues (for example, EphA2) may allow selective targeting of tumor cells without toxicity.

While traditional antisense oligonucleotides and siRNAs are very selective with regard to gene-targeting, growing data suggest that either off-target (Jackson et al., 2003) or immune-activating effects (Kim et al., 2004; Samuel, 2004) can occur. The interferon system is highly sensitive to the presence of double-stranded RNA (dsRNA). Recent studies suggest that siRNAs synthesized using phage RNA polymerases, but not chemically synthesized siRNAs can trigger a potent induction of interferon in a variety of cell lines (Schiffelers et al., 2004; Jackson et al., 2003; Kim et al., 2004).

Although siRNA appears to be more stable than antisense molecules, serum nucleases can degrade siRNAs (Leung and Whittaker, 2005). Thus, several research groups have developed modifications such as chemically stabilized siRNAs with partial phosphorothioate backbone and 2'-0-methyl sugar modifications or boranophosphate siRNAs (Leung and Whittaker, 2005). Elmen and colleagues modified siRNAs with the synthetic RNA-like high affinity nucleotide analogue, Locked Nucleic Acid (LNA), which significantly enhanced the serum half-life of siRNA and stabilized the structure without affecting the gene-silencing capability (Elmen et al., 2005). Alternative approaches including chemical modification (conjugation of cholesterol to the 3' end of the sense strand of siRNA by means of a pyrrolidine linker) may also allow systemic delivery without affecting function (Soutschek et al., 2004). Aspects of the present invention can use each of these modification strategies in combination with the compositions and methods described.

B. Beta Adrenergic Receptors and Stress Related Exacerbation of Cancer Cell Growth The inventors have recently demonstrated that chronic stress accelerates tumor growth by promoting angiogenesis using an ovarian tumor model. The inventor screened nineteen ovarian cancer cell lines by RT-PCR for the presence or absence of the $\beta1$ and $\beta2$ adrenergic receptors ($\beta AR$). The $\beta AR$ null (A2780 and RMG2) and positive (HeyA8 and SKOV3ip1) ovarian cancer cells were injected i.p. into mice 10 days after stress initiation. Blocking experiments using liposomal (DOPC) siRNA to $\beta1$, $\beta2$, or both receptors were performed. Remarkably, the $\beta2$ siRNA completely blocked the stress induced increase in tumor weight, number of nodules, and the invasive pattern of metastasis. Mice treated with combined $\beta1$ and $\beta2$ siRNA had results similar to the $\beta2$ siRNA only group. These studies indicate that the effects of chronic stress are primarily mediated through the $\beta2AR$ on ovarian cancer cells. Therefore, targeting the $\beta AR$ may have therapeutic implications for the management of ovarian cancer.

II. Lipid Preparations

The present invention provides methods and compositions for associating an inhibitory nucleic acid, such as a siNA (e.g., a siRNA) with a lipid and/or liposome. The siNA may be encapsulated in the aqueous interior of a liposome, interspersed within the lipid bilayer of a liposome, attached to a liposome via a linking molecule that is associated with both the liposome and the polynucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The liposome or liposome/siNA associated compositions of the present invention are not limited to any particular structure in solution. For example, they may be present in a bilayer structure, as micelles, or with a "collapsed" structure. They may also simply be interspersed in a solution, possibly forming aggregates which are not uniform in either size or shape.

Lipids are fatty substances which may be naturally occurring or synthetic lipids. For example, lipids include the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes. An example is the lipid dioleoylphosphatidylcholine (DOPC).

"Liposome" is a generic term encompassing a variety of unilamellar, multilamellar, and multivesicular lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). However, the present invention also encompasses compositions that have different structures in solution than the normal vesicular structure. For example, the lipids may assume a micellar structure or merely exist as non-uniform aggregates of lipid molecules. Also contemplated are lipofectamine-nucleic acid complexes.

Liposome-mediated polynucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the lipid may be associated with a hemaglutinating virus (HVJ). This has been shown to facilitate fusion with the cell membrane and promote cell entry of liposome-encapsulated DNA (Kaneda et al., 1989). In other embodiments, the lipid may be complexed or employed in conjunction with nuclear non-histone chromosomal proteins (HMG-1) (Kato et al., 1991). In yet further embodiments, the lipid may be complexed or employed in conjunction with both HVJ and HMG-1. In that such expression vectors have been successfully employed in transfer of a polynucleotide in vitro and in vivo, then they are applicable for the present invention.

A. Neutral Liposomes

"Neutral liposomes or lipid composition" or "non-charged liposomes or lipid composition," as used herein, are defined as liposomes or lipid compositions having one or more lipids that yield an essentially-neutral, net charge (substantially non-charged). By "essentially neutral" or "essentially non-charged", it is meant that few, if any, lipids within a given population (e.g., a population of liposomes) include a charge that is not canceled by an opposite charge of another component (e.g., fewer than 10% of components include a non-canceled charge, more preferably fewer than 5%, and most preferably fewer than 1%). In certain embodiments of the present invention, a composition may be prepared wherein the lipid component of the composition is essentially neutral but is not in the form of liposomes.

In certain embodiments, neutral liposomes or lipid compositions may include mostly lipids and/or phospholipids that are themselves neutral. In certain embodiments, amphipathic lipids may be incorporated into or used to generate neutral liposomes or lipid compositions. For example, a neutral liposome may be generated by combining positively and negatively charged lipids so that those charges substantially cancel one another. For such a liposome, few, if any, charged lipids are present whose charge is not canceled by an oppositely-charged lipid (e.g., fewer than 10% of charged lipids have a charge that is not canceled, more preferably fewer than 5%, and most preferably fewer than 1%). It is also recognized that the above approach may be used to generate a neutral lipid composition wherein the lipid component of the composition is not in the form of liposomes.

In certain embodiments, a neutral liposome may be used to deliver a siRNA. The neutral liposome may contain a siRNA directed to the suppression of translation of a single gene, or the neutral liposome may contain multiple siRNA that are directed to the suppression of translation of multiple genes. Further, the neutral liposome may also contain a chemotherapeutic in addition to the siRNA; thus, in certain embodiments, chemotherapeutic and a siRNA may be delivered to a cell (e.g., a cancerous cell in a human subject) in the same or separate compositions. An advantage to using neutral liposomes is that, in contrast to the toxicity that has been observed in response to cationic liposomes, little to no toxicity has yet been observed as a result of neutral liposomes.

B. Phospholipids

Lipid compositions of the present invention may comprise phospholipids. In certain embodiments, a single kind or type of phospholipid may be used in the creation of lipid compositions such as liposomes (e.g., DOPC used to generate neutral liposomes). In other embodiments, more than one kind or type of phospholipid may be used.

Phospholipids include glycerophospholipids and certain sphingolipids. Phospholipids include, but are not limited to, dioleoylphosphatidylycholine ("DOPC"), egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dilauryloylphosphatidylglycerol ("DLPG"), dimyristoylphosphatidylglycerol ("DMPG"), dipalmitoylphosphatidylglycerol ("DPPG"), distearoylphosphatidylglycerol ("DSPG"), distearoyl sphingomyelin ("DSSP"), distearoylphophatidylethanolamine ("DSPE"), dioleoylphosphatidylglycerol ("DOPG"), dimyristoyl phosphatidic acid ("DMPA"), dipalmitoyl phosphatidic acid ("DPPA"), dimyristoyl phosphatidylethanolamine ("DMPE"), dipalmitoyl phosphatidylethanolamine ("DPPE"), dimyristoyl phosphatidylserine ("DMPS"), dipalmitoyl phosphatidylserine ("DPPS"), brain phosphatidylserine ("BPS"), brain sphingomyelin ("BSP"), dipalmitoyl sphingomyelin ("DPSP"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), dioleoylphosphatidylethanolamine ("DOPE"), palmitoyloeoyl phosphatidylcholine ("POPC"), palmitoyloeoyl phosphatidyletlianolamine ("POPE"), lysophosphatidylcholine, lysophosphatidylethanolamine, and dilinoleoylphosphatidylcholine.

Phospholipids include, for example, phosphatidylcholines, phosphatidylglycerols, and phosphatidylethanolamines; because phosphatidylethanolamines and phosphatidyl cholines are non-charged under physiological conditions (i.e., at about pH 7), these compounds may be particularly useful for generating neutral liposomes. In certain embodiments, the phospholipid DOPC is used to produce non-charged liposomes or lipid compositions. In certain embodiments, a lipid that is not a phospholipid (e.g., a cholesterol) can also be used Phospholipids may be from natural or synthetic sources. However, phospholipids from natural sources, such as egg or soybean phosphatidylcholine, brain phosphatidic acid, brain or plant phosphatidylinositol, heart cardiolipin and plant or bacterial phosphatidylethanolamine are not used in certain embodiments as the primary phosphatide (i.e., constituting 50% or more of the total phosphatide composition) because this may result in instability and leakiness of the resulting liposomes.

C. Production of Liposomes

Liposomes and lipid compositions of the present invention can be made by different methods. For example, a nucleotide (e.g., siRNA) may be encapsulated in a neutral liposome using a method involving ethanol and calcium (Bailey and Sullivan, 2000). The size of the liposomes varies depending on the method of synthesis. A liposome suspended in an aqueous solution is generally in the shape of a spherical vesicle, and may have one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

Lipids suitable for use according to the present invention can be obtained from commercial sources. For example, dimyristyl phosphatidylcholine ("DMPC") can be obtained from Sigma Chemical Co., dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform may be used as the only solvent since it is more readily evaporated than methanol.

Liposomes within the scope of the present invention can be prepared in accordance with known laboratory techniques. In certain embodiments, liposomes are prepared by mixing liposomal lipids, in a solvent in a container (e.g., a glass, pear-shaped flask). The container will typically have a volume ten-times greater than the volume of the expected suspension of liposomes. Using a rotary evaporator, the solvent may be removed at approximately 40° C. under negative pressure. The solvent may be removed within about 5 minutes to 2 hours, depending on the desired volume of the liposomes. The composition can be dried further in a desiccator under vacuum. Dried lipids can be hydrated at approximately 25-50 mM phospholipid in sterile, pyrogen-free water by shaking until all the lipid film is resuspended. The aqueous liposomes can be then separated into aliquots, each placed in a vial, lyophilized and sealed under vacuum.

Liposomes can also be prepared in accordance with other known laboratory procedures: the method of Bangham et al. (1965), the contents of which are incorporated herein by reference; the method of Gregoriadis, as described in DRUG CARRIERS IN BIOLOGY AND MEDICINE (1979), the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

Dried lipids or lyophilized liposomes may be dehydrated and reconstituted in a solution of inhibitory peptide and diluted to an appropriate concentration with a suitable solvent (e.g., DPBS). The mixture may then be vigorously shaken in a vortex mixer. Unencapsulated nucleic acid may be removed by centrifugation at 29,000 g and the liposomal pellets washed. The washed liposomes may be resuspended at an appropriate total phospholipid concentration (e.g., about 50-200 mM). The amount of nucleic acid encapsulated can be determined in accordance with standard methods. After determination of the amount of nucleic acid encapsulated in the liposome preparation, the liposomes may be diluted to appropriate concentrations and stored at 4° C. until use.

III. Inhibition of Gene Expression

Inhibitory nucleic acids or "siNA", as used herein, is defined as a short interfering nucleic acid. Examples of siNA include but are not limited to RNAi, double-stranded RNA, and siRNA. A siNA can inhibit the transcription or translation of a gene in a cell. A siNA may be from 16 to 1000 or more nucleotides long, and in certain embodiments from 18 to 100 nucleotides long. In certain embodiments, the siNA may be 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides long. The siNA may comprise a nucleic acid and/or a nucleic acid analog. Typically, a siNA will inhibit the translation of a single gene within a cell; however, in certain embodiments, a siNA will inhibit the translation of more than one gene within a cell.

Within a siNA, the components of a nucleic acid need not be of the same type or homogenous throughout (e.g., a siNA may comprise a nucleotide and a nucleic acid or nucleotide analog). Typically, siNA form a double-stranded structure; the double-stranded structure may result from two separate nucleic acids that are partially or completely complementary.

In certain embodiments of the present invention, the siNA may comprise only a single nucleic acid (polynucleotide) or nucleic acid analog and form a double-stranded structure by complementing with itself (e.g., forming a hairpin loop). The double-stranded structure of the siNA may comprise 16, 20, 25, 30, 35, 40, 45, 50, 60, 65, 70, 75, 80, 85, 90 to 100, 150, 200, 250, 300, 350, 400, 450, 500 or more contiguous nucleobases, including all ranges therebetween. The siNA may comprise 17 to 35 contiguous nucleobases, more preferably 18 to 30 contiguous nucleobases, more preferably 19 to 25 nucleobases, more preferably 20 to 23 contiguous nucleobases, or 20 to 22 contiguous nucleobases, or 21 contiguous nucleobases that hybridize with a complementary nucleic acid (which may be another part of the same nucleic acid or a separate complementary nucleic acid) to form a double-stranded structure.

siNA (e.g., siRNA) are well known in the art. For example, siRNA and double-stranded RNA have been described in U.S. Pat. Nos. 6,506,559 and 6,573,099, as well as in U.S. Patent Applications 2003/6051263, 2003/0055020, 2004/0265839, 2002/0168707, 2003/0159161, and 2004/0064842, all of which are herein incorporated by reference in their entirety.

A. RNA Interference

Agents of the present invention useful for practicing the methods of the present invention include, but are not limited to siRNAs of FAK, EphA2, or β2AR. Typically, such agents are capable of (i) binding to the respective mRNA, (ii) interfere with signaling and/or (iii) inhibit proliferation cancer or tumor cell. In a preferred embodiment, the agent inhibiting cell proliferation is a siRNA of FAK. The present invention provides compositions and methods using RNA interference to modulate FAK expression. These methods and compositions are useful for the treatment of disease (e.g., cancer), induction of apoptosis, and/or interfering with biological pathways.

Typically, introduction of double-stranded RNA (dsRNA), which may alternatively be referred to herein as small interfering RNA (siRNA), induces potent and specific gene silencing, a phenomena called RNA interference or RNAi. This phenomenon has been extensively documented in the nematode *C. elegans* (Fire et al., 1998), but is widespread in other organisms, ranging from trypanosomes to mouse. Depending on the organism being discussed, RNA interference has been referred to as "cosuppression," "post-transcriptional gene silencing," "sense suppression," and "quelling." RNAi is an attractive biotechnological tool because it provides a means for knocking out the activity of specific genes.

In certain embodiments of the present invention, the agent for use in the methods of the present invention is a siRNA of FAK, EphA2, β2AR and combinations thereof. siRNA can be used to reduce the expression level of FAK, EphA2, and/or β2AR. A siRNA of FAK, EphA2, and/or β2AR hybridizes to a FAK, EphA2, and/or β2AR mRNA and thereby decreases or inhibits production of FAK, EphA2, and/or β2AR protein.

In designing RNAi there are several factors that need to be considered such as the nature of the siRNA, the durability of the silencing effect, and the choice of delivery system. To produce an RNAi effect, the siRNA that is introduced into the organism will typically contain exonic sequences. Furthermore, the RNAi process is homology dependent, so the sequences must be carefully selected so as to maximize gene specificity, while minimizing the possibility of cross-interference between homologous, but not gene-specific sequences. Preferably the siRNA exhibits greater than 80, 85, 90, 95, 98,% or even 100% identity between the sequence of the siRNA and the gene to be inhibited. Sequences less than about 80% identical to the target gene are substantially less effective. Thus, the greater homology between the siRNA of FAK, EphA2, and/or β2AR and the FAK, EphA2, and/or β2AR gene whose expression is to be inhibited, the less likely expression of unrelated genes will be affected.

In addition, the size of the siRNA is an important consideration. Generally, the present invention relates to siRNA molecules of FAK, EphA2, and/or β2AR, which are double or single stranded and comprise at least about 19-25 nucleotides, and are able to modulate the gene expression of FAK, EphA2, and/or β2AR. In the context of the present invention, the siRNA is preferably less than 500, 200, 100, 50 or 25 nucleotides in length. More preferably, the siRNA is from about 19 nucleotides to about 25 nucleotides in length.

In one aspect, the invention generally features an isolated siRNA molecule of at least 19 nucleotides, having at least one strand that is substantially complementary to at least ten but no more than thirty consecutive nucleotides of FAK, EphA2, and/or β2AR, and that reduces the expression of FAK, EphA2, and/or β2AR gene or protein. In a preferred embodiment of the present invention, the siRNA molecule has at least one strand that is substantially complementary to at least ten but no more than thirty consecutive nucleotides of the mRNA for human FAK (GenBank accession NM_005607 and NM_153831, SEQ ID NO:5 and 6, respectively), EphA2 (GenBank accession BC037166 (GI:33879863), SEQ ID NO:18, and/or β2AR (GenBank accession AF022953 (GI: 2570526), SEQ ID NO:19. Each Genbank accession is incorporated herein by reference in its entirety, as of Apr. 15, 2005. In still a further aspect the isolated siRNA molecule has at least one strand that is substantially complementary to at least 19 to 25 contiguous nucleotides of FAK, SEQ ID NO:5 and 6, respectively), EphA2 (SEQ ID NO:18) and/or β2AR (SEQ ID NO:19). In certain embodiments of the present invention, the siRNA nucleic acid sequence is 5'-CCACCUGGGC-CAGUAUUAU-3' (SEQ ID NO:7), 5'-AAUGACAUGC-CGAUCUACAUG-3' (SEQ ID NO:4), or 5'-CAGAGUG-GAUAUCACGUGGAA-3' (SEQ ID NO:12).

In another preferred embodiment, the siRNA molecule of FAK, EphA2, and/or β2AR includes a sequence that is at least 75, 80, 85, or 90% homologous, preferably 95%, 99%, or 100% homologous, to at least 10 contiguous nucleotides of the nucleic acid sequences shown in SEQ ID NO:5, SEQ ID NO:6, SEQ ID NO:18 and SEQ ID NO:19. Without undue experimentation and using the disclosure of this invention, it is understood that additional siRNAs of FAK, EphA2, and/or β2AR that modulate FAK, EphA2, and/or β2AR expression can be designed and used to practice the methods of the invention.

The siRNA may also comprise an alteration of one or more nucleotides. Such alterations can include the addition of non-nucleotide material, such as to the end(s) of the 19 to 25 nucleotide RNA or internally (at one or more nucleotides of the RNA). In certain aspects, the RNA molecule contains a 3'-hydroxyl group. Nucleotides in the RNA molecules of the present invention can also comprise non-standard nucleotides, including non-naturally occurring nucleotides or deoxyribonucleotides. The double-stranded oligonucleotide may contain a modified backbone, for example, phosphorothioate, phosphorodithioate, or other modified backbones known in the art, or may contain non-natural internucleoside linkages. Additional modifications of siRNAs (e.g., 2'-O-methyl ribonucleotides, 2'-deoxy-2'-fluoro ribonucleotides, "universal base" nucleotides, 5-C-methyl nucleotides, one or more phosphorothioate internucleotide linkages, and inverted deoxyabasic residue incorporation) can be found in U.S. Application Publication 20040019001 and U.S. Pat. No. 6,673,611 (each of which is incorporated by reference in its entirety). Collectively, all such altered nucleic acids or RNAs described above are referred to as modified siRNAs.

Preferably, RNAi is capable of decreasing the expression of FAK, EphA2, and/or β2AR gene or protein in a cell by at least 10%, 20%, 30%, or 40%, more preferably by at least 50%, 60%, or 70%, and most preferably by at least 75%, 80%, 90%, 95% or more.

Introduction of siRNA into cells can be achieved by methods known in the art, including for example, microinjection, electroporation, or transfection of a vector comprising a nucleic acid from which the siRNA can be transcribed. Alternatively, a siRNA can be directly introduced into a cell in a form that is capable of binding to target mRNA transcripts. To increase durability and membrane-permeability the siRNA may be combined or modified with liposomes, poly-L-lysine, lipids, cholesterol, lipofectine or derivatives thereof. In certain aspects cholesterol-conjugated siRNA can be used (see, Song et al., 2003).

IV. Nucleic Acids

The present invention provides methods and compositions for the delivery of siNA via neutral liposomes. Because a siNA is composed of a nucleic acid, methods relating to nucleic acids (e.g., production of a nucleic acid, modification of a nucleic acid, etc.) may also be used with regard to a siNA.

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between 3 and about 100 nucleobases in length. The term "polynucleotide" refers to at least one molecule of greater than about 100 nucleobases in length.

These definitions refer to a single-stranded or double-stranded nucleic acid molecule. Double stranded nucleic acids are formed by fully complementary binding, although in some embodiments a double stranded nucleic acid may formed by partial or substantial complementary binding. Thus, a nucleic acid may encompass a double-stranded molecule that comprises one or more complementary strand(s) or "complement(s)" of a particular sequence, typically comprising a molecule. As used herein, a single stranded nucleic acid may be denoted by the prefix "ss" and a double stranded nucleic acid by the prefix "ds".

A. Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, caboxyalkyl, amino, hydroxyl, halogen (i.e., fluoro, chloro, bromo, or iodo), thiol or alkylthiol moeity. Preferred alkyl (e.g., alkyl, caboxyalkyl, etc.) moeities comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothyline, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like. Purine and pyrmidine derivatives or analogs include, but are not limited to (abbreviation/modified base description):ac4c/4-acetylcytidine, Mam5s2u/5-methoxyaminomethyl-2-thiouridine, Chm5u/5-(carboxyhydroxylmethyl) uridine, Man q/Beta, D-mannosylqueosine, Cm/2'-O-methylcytidine, Mcm5s2u/5-methoxycarbonylmethyl-2-thiouridine, Cmnm5s2u/5-carboxymethylamino-methyl-2-thioridine, Mcm5u/5-methoxycarbonylmethyluridine, Cmnm5u/5-carboxymethylaminomethyluridine, Mo5u/5-methoxyuridine, D/Dihydrouridine, Ms2i6a, 2-methylthio-N6-isopentenyladenosine, Fm/2'-O-methylpseudouridine, Ms2t6a/N-((9-beta-D-ribofuranosyl-2-methylthiopurine-6-yl)carbamoyl)threonine, Gal q/Beta,D-galactosylqueosine, Mt6a/N-((9-beta-D-ribofuranosylpurine-6-yl)N-methyl-carbamoyl)threonine, Gm/2'-O-methylguanosine, Mv/Uridine-5-oxyacetic acid methylester, I/Inosine, o5u/Uridine-5-oxy-acetic acid (v), I6a/N6-isopentenyladenosine, Osyw/Wybutoxosine, m1a/1-methyladenosine, P/Pseudouridine, m1f/1-methylpseudouridine, Q/Queosine, m1g/1-methylguanosine, s2c/2-thiocytidine, m1I/1-methylinosine, s2t/5-methyl-2-thiouridine, m22g/2,2-dimethylguanosine, s2u/2-thiouridine, m2a/2-methyladenosine, s4u/4-thiouridine, m2g/2-methylguanosine, T/5-methyluridine, m3c/3-methylcytidine, t6a/N-((9-beta-D-ribofuranosylpurine-6-yl)carbamoyl)threonine, m5c/5-methylcytidine, Tm/2'-O-methyl-5-methyluridine, m6a/N6-methyladenosine, Um/2'-O-methyluridine, m7g/7-methylguanosine, Yw/Wybutosine, Mam5u/5-methylaminomethyluridine, or X/3-(3-amino-3-carboxypropyl)uridine, (acp3)u.

A nucleobase may be comprised in a nucleoside or nucleotide, using any chemical or natural synthesis method described herein or known to one of ordinary skill in the art.

B. Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom, in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

C. Nucleotides

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

D. Nucleic Acid Analogs

A nucleic acid may comprise, or be composed entirely of, a derivative or analog of a nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides, or nucleic acids comprising 5-carbon sugar and/or backbone moiety derivatives or analogs, include those in U.S. Pat. No. 5,681,947 which describes oligonucleotides comprising purine derivatives that form triple helixes with and/or prevent expression of dsDNA; U.S. Pat. Nos. 5,652,099 and 5,763,167 which describe nucleic acids incorporating fluorescent analogs of nucleosides found in DNA or RNA, particularly for use as fluorescent nucleic acids probes; U.S. Pat. No. 5,614,617 which describes oligonucleotide analogs with substitutions on pyrimidine rings that possess enhanced nuclease stability; U.S. Pat. Nos. 5,670,663, 5,872,232 and 5,859,221 which describe oligonucleotide analogs with modified 5-carbon sugars (i.e., modified 2'-deoxyfuranosyl moieties) used in nucleic acid detection; U.S. Pat. No. 5,446,137 which describes oligonucleotides comprising at least one 5-carbon sugar moiety substituted at the 4' position with a substituent other than hydrogen that can be used in hybridization assays; U.S. Pat. No. 5,886,165 which describes oligonucleotides with both deoxyribonucleotides with 3'-5' internucleotide linkages and ribonucleotides with 2'-5' internucleotide linkages; U.S. Pat. No. 5,714,606 which describes a modified internucleotide linkage wherein a 3'-position oxygen of the internucleotide linkage is replaced by a carbon to enhance the nuclease resistance of nucleic acids; U.S. Pat. No. 5,672,697 which describes oligonucleotides containing one or more 5' methylene phosphonate internucleotide linkages that enhance nuclease resistance; U.S. Pat. Nos. 5,466,786 and 5,792,847 which describe the linkage of a substituent moeity which may comprise a drug or label to the 2' carbon of an oligonucleotide to provide enhanced nuclease stability and ability to deliver drugs or detection moieties; U.S. Pat. No. 5,223,618 which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA; U.S. Pat. No. 5,470,967 which describes oligonucleotides comprising at least one sulfamate or sulfamide internucleotide linkage that are useful as nucleic acid hybridization probe; U.S. Pat. Nos. 5,378,825, 5,777,092, 5,623,070, 5,610,289 and 5,602,240 which describe oligonucleotides with three or four atom linker moeity replacing phosphodiester backbone moeity used for improved nuclease resistance, cellular uptake and regulating RNA expression; U.S. Pat. No. 5,858,988 which describes hydrophobic carrier agent attached to the 2'-O position of oligonucleotides to enhanced their membrane permeability and stability; U.S. Pat. No. 5,214,136 which describes oligonucleotides conjugated to anthraquinone at the 5' terminus that possess enhanced hybridization to DNA or RNA; enhanced stability to nucleases; U.S. Pat. No. 5,700,922 which describes PNA-DNA-PNA chimeras wherein the DNA comprises 2'-deoxy-erythro-pentofaranosyl nucleotides for enhanced nuclease resistance, binding affinity, and ability to activate RNase H; and U.S. Pat. No. 5,708,154 which describes RNA linked to a DNA to form a DNA-RNA hybrid.

E. Polyether and Peptide Nucleic Acids

In certain embodiments, it is contemplated that a nucleic acid comprising a derivative or analog of a nucleoside or nucleotide may be used in the methods and compositions of the invention. A non-limiting example is a "polyether nucleic acid", described in U.S. Pat. No. 5,908,845, incorporated herein by reference. In a polyether nucleic acid, one or more nucleobases are linked to chiral carbon atoms in a polyether backbone.

Another non-limiting example is a "peptide nucleic acid", also known as a "PNA", "peptide-based nucleic acid analog" or "PENAM", described in U.S. Pat. Nos. 5,786,461, 5891,625, 5,773,571, 5,766,855, 5,736,336, 5,719,262, 5,714,331, 5,539,082, and WO 92/20702, each of which is incorporated herein by reference. Peptide nucleic acids generally have enhanced sequence specificity, binding properties, and resistance to enzymatic degradation in comparison to molecules such as DNA and RNA (Egholm et al., 1993; PCT/EP/01219). A peptide nucleic acid generally comprises one or more nucleotides or nucleosides that comprise a nucleobase moiety, a nucleobase linker moeity that is not a 5-carbon sugar, and/or a backbone moiety that is not a phosphate backbone moiety. Examples of nucleobase linker moieties described for PNAs include aza nitrogen atoms, amido and/or ureido tethers (see for example, U.S. Pat. No. 5,539,082). Examples of backbone moieties described for PNAs include an aminoethylglycine, polyamide, polyethyl, polythioamide, polysulfinamide or polysulfonamide backbone moiety.

In certain embodiments, a nucleic acid analogue such as a peptide nucleic acid may be used to inhibit nucleic acid amplification, such as in PCR™, to reduce false positives and discriminate between single base mutants, as described in U.S. Pat. No. 5,891,625. Other modifications and uses of nucleic acid analogs are known in the art, and it is anticipated that these techniques and types of nucleic acid analogs may be used with the present invention. In a non-limiting example, U.S. Pat. No. 5,786,461 describes PNAs with amino acid side chains attached to the PNA backbone to enhance solubility of the molecule. In another example, the cellular uptake property of PNAs is increased by attachment of a lipophilic group. U.S. application Ser. No. 117,363 describes several alkylamino moeities used to enhance cellular uptake of a PNA. Another example is described in U.S. Pat. Nos. 5,766,855, 5,719,262, 5,714,331 and 5,736,336, which describe PNAs comprising naturally and non-naturally occurring nucleobases and alkylamine side chains that provide improvements in sequence specificity, solubility and/or binding affinity relative to a naturally occurring nucleic acid.

F. Preparation of Nucleic Acids

A nucleic acid may be made by any technique known to one of ordinary skill in the art, such as chemical synthesis, enzymatic production or biological production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

G. Purification of Nucleic Acids

A nucleic acid may be purified on polyacrylamide gels, cesium chloride centrifugation gradients, or by any other means known to one of ordinary skill in the art (see for example, Sambrook et al., 2001, incorporated herein by reference).

In certain embodiments, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

H. Hybridization

As used herein, "hybridization", "hybridizes" or "capable of hybridizing" is understood to mean the forming of a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

V. Cancer

The present invention may be used to treat a disease, such as cancer. For example, a siRNA may be delivered via a non-charged liposome to treat a cancer. The cancer may be a solid tumor, metastatic cancer, or non-metastatic cancer. In certain embodiments, the cancer may originate in the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In certain embodiments, the cancer is human ovarian cancer. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Nonetheless, it is also recognized that the present invention may also be used to treat a non-cancerous disease (e.g., a fungal infection, a bacterial infection, a viral infection, and/or a neurodegenerative disease).

VI. Pharmaceutical Preparations

Where clinical application of non-charged lipid component (e.g., in the form of a liposome) containing a siNA is undertaken, it will generally be beneficial to prepare the lipid complex as a pharmaceutical composition appropriate for the intended application. This will typically entail preparing a pharmaceutical composition that is essentially free of pyrogens, as well as any other impurities that could be harmful to humans or animals. One may also employ appropriate buffers to render the complex stable and allow for uptake by target cells.

The phrases "pharmaceutical or pharmacologically acceptable" refers to molecular entities and compositions that do not produce an adverse, allergic or other untoward reaction when administered to an animal, such as a human, as appropriate. The preparation of a pharmaceutical composition that contains at least one non-charged lipid component comprising a siNA or additional active ingredient will be known to those of skill in the art in light of the present disclosure, as exemplified by Remington: The Science and Practice of Pharmacy, 21st, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. A pharmaceutically acceptable carrier is preferably formulated for administration to a human, although in certain embodiments it may be desirable to use a pharmaceutically acceptable carrier that is formulated for administration to a non-human animal but which would not be acceptable (e.g., due to governmental regulations) for administration to a human. Except insofar as any conventional carrier is incompatible with the active ingredient, its use in the therapeutic or pharmaceutical compositions is contemplated.

The actual dosage amount of a composition of the present invention administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 µg/kg/body weight to about 100 mg/kg/body weight, about 5 microgram/kg/body weight to about 500 milligram/kg/body weight, etc., can be administered.

A gene expression inhibitor may be administered in a dose of 1, 2, 3, 4, 5, 6, 7, 8, 9, 10, 15, 20, 25, 30, 40, 50, 60, 70, 80, 90, 100 or more µg of nucleic acid per dose. Each dose may be in a volume of 1, 10, 50, 100, 200, 500, 1000 or more µl or ml.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Topical administration may be particularly advantageous for the treatment of skin cancers, to prevent chemotherapy-induced alopecia or other dermal hyperproliferative disorder. Alternatively, administration may be by orthotopic, intradermal, subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, aerosol delivery can be used. Volume of the aerosol is between about 0.01 ml and 0.5 ml.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses discussed above in association with its administration, i.e., the appropriate route and treatment regimen. The quantity to be administered, both according to number of treatments and unit dose, depends on the protection or effect desired.

Precise amounts of the therapeutic composition also depend on the judgment of the practitioner and are peculiar to each individual. Factors affecting the dose include the physical and clinical state of the patient, the route of administration, the intended goal of treatment (e.g., alleviation of symptoms versus cure) and the potency, stability and toxicity of the particular therapeutic substance.

VII. Combination Treatments

In certain embodiments, the compositions and methods of the present invention involve an inhibitor of gene expression, or construct capable of expressing an inhibitor of gene expression, in combination with a second or additional therapy. The methods and compositions including combination therapies enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both an inhibitor of gene expression and a second therapy. A tissue, tumor, or cell can be contacted with one or more compositions or pharmacological formulation(s) including one or more of the agents (i.e., inhibitor of gene expression or an anti-cancer agent), or by contacting the tissue, tumor, and/or cell with two or more distinct compositions or formulations, wherein one composition provides 1) an inhibitor of gene expression; 2) an anti-cancer agent, or 3) both an inhibitor of gene expression and an anti-cancer agent. Also, it is contemplated that such a combination therapy can be used in conjunction with a chemotherapy, radiotherapy, surgical therapy, or immunotherapy.

An inhibitor of gene expression may be administered before, during, after or in various combinations relative to an anti-cancer treatment. The administrations may be in intervals ranging from concurrently to minutes to days to weeks. In embodiments where the inhibitor of gene expression is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the inhibitor of gene expression therapy and the anti-cancer therapy within about 12 to 24 or 72 h of each other and, more preferably, within about 6-12 h of each other. In some situations it may be desirable to extend the time period for treatment significantly where several days (2, 3, 4, 5, 6 or 7) to several weeks (1, 2, 3, 4, 5, 6, 7 or 8) lapse between respective administrations.

In certain embodiments, a course of treatment will last 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 days or more. It is contemplated that one agent may be given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, any combination thereof, and another agent is given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1, 2, 3, 4, 5, 6, 7 days, and/or 1, 2, 3, 4, 5 weeks, and/or 1, 2, 3, 4, 5, 6, 7, 8, 9, 10, 11, 12 months or more, depending on the condition of the patient, such as their prognosis, strength, health, etc.

Various combinations may be employed. For the example below an inhibitor of gene expression therapy is "A" and an anti-cancer therapy is "B":

A/B/A B/A/B B/B/A A/A/B A/B/B B/A/A A/B/B/B

B/A/B/B B/B/B/A B/B/A/B A/A/B/B A/B/A/B A/B/B/A

B/B/A/A B/A/B/A B/A/A/B A/A/A/B B/A/A/A A/B/A/A

A/A/B/A

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy. It is expected that the treatment cycles would be repeated as necessary. It also is contemplated that various standard therapies, as well as surgical intervention, may be applied in combination with the described therapy.

In specific aspects, it is contemplated that a standard therapy will include chemotherapy, radiotherapy, immunotherapy, surgical therapy or gene therapy and may be employed in combination with the inhibitor of gene expression therapy, anticancer therapy, or both the inhibitor of gene expression therapy and the anti-cancer therapy, as described herein.

A. Chemotherapy

Cancer therapies include a variety of combination therapies with both chemical and radiation based treatments. Chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristin, vinblastin and methotrexate, or any analog, derivative, or variant of the foregoing.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves, proton beam irradiation (U.S. Pat. Nos. 5,760,395 and 4,870,287) and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

C. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

Another immunotherapy could also be used as part of a combined therapy with gen silencing therapy discussed above. In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, gamma-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds can be used to target the anti-cancer agents discussed herein.

Examples of immunotherapies currently under investigation or in use are immune adjuvants e.g., *Mycobacterium bovis*, *Plasmodium falciparum*, dinitrochlorobenzene and aromatic compounds (U.S. Pat. Nos. 5,801,005 and 5,739, 169; Hui and Hashimoto, 1998; Christodoulides et al., 1998), cytokine therapy, e.g., interferons α, β and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

D. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is farther contemplated that other agents that increase the sensitivity of a hyperproliferative cell to apoptosis, such as the antibody c225, could be used in combination with the present invention to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

VIII. Kits and Diagnostics

In various aspects of the invention, a kit is envisioned containing therapeutic agents and/or other therapeutic and delivery agents. In some embodiments, the present invention contemplates a kit for preparing and/or administering a therapy of the invention. The kit may comprise reagents capable of use in administering an active or effective agent(s) of the invention. Reagents of the kit may include at least one inhibitor of gene expression, one or more lipid component, one or more anti-cancer component of a combination therapy, as well as reagents to prepare, formulate, and/or administer the components of the invention or perform one or more steps of the inventive methods.

In some embodiments, the kit may also comprise a suitable container means, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods, and will follow substantially the same procedures as described herein or are known to those of ordinary skill.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Therapeutic EphA2 Gene Targeting In Vivo Using Neutral Liposomal siRNA Delivery

I. Materials and Methods

Cell Lines and Culture.

The ovarian cancer cell lines HeyA8 and SKOV3ip1 (Apte, 2004) were maintained in RPMI-1640 supplemented with 15% FBS and 0.1% gentamycin sulfate (Gemini Bioproducts, Calabasas, Calif.). All in vitro experiments were conducted at 60-80% confluence. For in vivo injection, cells were trypsinized and centrifuged at 1000 rpm for 7 minutes at 4° C., washed twice, and reconstituted in serum-free Hank's Balanced Salt Solution (Gibco, Carlsbad, Calif.) at a concentration of $5\times10^6$ cells/ml (SKOV3ip1) or $1.25\times10^6$ cells/ml (HeyA8) for 200 µl intraperitoneal injections.

siRNA Constructs and In Vitro Delivery.

SiRNA was purchased from Qiagen (Valencia, Calif.) in three formulations. A non-silencing siRNA sequence, shown by BLAST search to not share sequence homology with any known human mRNA (target sequence 5'-AATTCTCGAACGTGTCACGT-3' (SEQ ID NO:1)) and tagged with Alexa-555 was used to determine uptake and distribution in various tissues when administered in vivo. SiRNA with the target sequence 5'-AATGACATGCCGATCTACATG-3' (SEQ ID NO:2), designed and shown (Duxbury, 2004) to target mRNA of the receptor tyrosine kinase EphA2, was used to downregulated EphA2 in vitro and in vivo. A non-silencing siRNA construct (sequence as above without an Alexa-555 tag) was used as control for EphA2-targeting experiments. For in vitro delivery, 5 µg siRNA were incubated with 30 µl lipofectamine 2000 (Qiagen) for 10 min at RT, and added to cells in culture at 80% confluence in 35 mm culture plates. The media was changed 6 hrs later, and cells collected after 48 hrs as lysate for Western blot analysis.

Liposomal Preparation.

SiRNA for in vivo delivery was either administered naked (without transfection agent), incorporated into DOTAP (N-[1-(2,3-Dioleoyloxy)propyl]-N,N,N-trimethylammonium methyl sulfate; Roche, Indianapolis, Ind.), or incorporated into DOPC. DOPC and siRNA were mixed in the presence of excess tertiary-butanol at a ratio of 1:10 siRNA:DOPC (weight:weight). Tween-20 was added to the mixture in a ratio of 1:19 Tween-20:siRNA/DOPC. The mixture was vortexed, frozen in an acetone/dry ice bath, and lyophilized. Prior to in vivo administration, this preparation was hydrated with normal 0.9% saline at a concentration of 15 µg/ml, to achieve the desired dose in 150-200 µl per injection. To estimate the quantity of siRNA not taken up by liposomes, free siRNA was separated from liposomes using 30,000 nominal molecular weight limit (NMWL) filter units (Millipore Corp, Billerica, Mass.). The liposomal suspension was added to the filters and centrifuged at 5,000 g for 40 min at room temperature. Fractions were collected, the material trapped in the filter was reconstituted with 0.9% saline, and siRNA of the collected fraction and the elute were measured by spectrophotometry.

Orthotopic In Vivo Model and Tissue Processing.

Female athymic nude mice (NCr-nu) were purchased from the National Cancer Institute-Frederick Cancer Research and Development Center (Frederick, Md.) and housed in specific-pathogen-free conditions. They were cared for in accordance with guidelines set forth by the American Association for Accreditation of Laboratory Animal Care and the U.S. Public Health Service *Policy on Human Care and Use of Laboratory Animals*, and all studies were approved and supervised by the MDACC Institutional Animal Care and Use Committee. Studies to determine uptake of single-dose fluorescent siRNA in tissue or silencing potential of single-dose siRNA against EphA2 were initiated once intraperitoneal tumors reached a size of 0.5-1.0 $cm^3$, as assessed by palpation. Liposomal siRNA (5 µg) was administered as a 200 µl intravenous bolus into the tail veil under normal pressure, and tumor and other tissues harvested at various time points after injection (1 hr, 6 hr, 48 hr, 4 days, 7 days, or 10 days). Tissue specimens were snap frozen for lysate preparation, fixed in formalin for paraffin embedding, or frozen in OCT media for frozen slide preparation. For long-term experiments to assess tumor growth, therapy began one week after cell injection. Paclitaxel 100 µg or vehicle was injected intraperitoneally once a week; siRNA (nonspecific or EphA2-targeting, 150 µg/kg) in liposomes, or empty liposomes, were injected twice per week intravenously in 150-200 µl volume (depending on mouse weight) with normal pressure. Mice (n=10/group) were monitored for adverse effects, and tumors were harvested after 4 weeks of therapy, or when any of the mice began to appear moribund. Mouse weight, tumor weight, and distribution of tumor were recorded. Vital organs were also harvested and necropsies performed by a pathologist for evidence of tissue toxicity.

Immunofluorescence and Confocal Microscopy.

Tissue for immunofluorescence (IF) was collected from sacrificed mice, immediately placed in OCT media, and rapidly frozen. Frozen sections were cut at 8 µm sections for conventional microscopy and 30 µm sections for confocal microscopy. Tissue was fixed with acetone and either examined immediately or co-stained for f4/80 (to detect scavenging macrophages) or CD31 (to detect endothelial cells). For IF detection, slides were blocked with 5% normal horse serum and 1% normal goat serum (Invitrogen, Carlsbad, Calif.) in phosphate-buffered saline (PBS), exposed to 10 µg/ml anti-f4/80 antibody (Serotec, Oxford, UK) or 0.625 µg/ml anti-CD31 antibody in blocking solution overnight at 4° C., washed with PBS, and exposed to 4 µg/ml anti-rat antibody-Alexa488 (Molecular Probes, Eugene, Oreg.) in blocking solution for one hour at room temperature. Slides were washed with PBS, exposed to either 1.0 µg/ml Hoescht (Molecular Probes, in PBS) or 10 nM Sytox green (Molecular Probes, in PBS) for 10 minutes to stain nuclei, washed, and covered with propylgallate and cover slips for microscopic evaluation. Conventional microscopy was performed with a Zeiss AxioPlan 2 microscope, Hamamatsu ORCA-ER Digital camera (Hamamatsu Corp, Japan), and ImagePro software (Media Cybernetics, Silver Spring, Md.). Fluorescence in three dimensions within 30 µm sections was examined with a Zeiss LSM 510 confocal microscope and LSM 510 Image Browser software (Carl Zeiss, Inc., Germany).

Western Blot.

Cultured cell lysates were prepared by washing cells with PBS followed by incubation in modified RIPA lysis buffer (50 mM Tris, 150 mM NaCl, 1% triton, 0.5% deoxycholate plus 25 µg/ml leupeptin, 10 µg/ml aprotinin, 2 mM EDTA, and 1 mM sodium orthovanadate (Sigma Chemical Co, St. Louis, Mo.)) for 10 min at 4° C. Cells were scraped from plates, centrifuged at 13,000 rpm for 20 min at 4° C. and the supernatant stored at −80° C. To prepare lysate from snap frozen tissue, approximately 30 mm³ cuts of tissue were incubated on ice in RIPA for 3 hrs, mortar and pestle disrupted and homogenized, centrifuged, and the supernatant stored at −80° C. Samples from 3 regions of the tumor were collected and tested individually. Protein concentrations were determined using a BCA Protein Assay Reagent kit (Pierce Biotechnology, Rockford, Ill.), and subjected to 10% SDS-PAGE separation. Samples transferred to a nitrocellulose membrane by semi-dry electrophoresis (Bio-Rad Laboratories, Hercules, Calif.) were incubated with 0.625 µg/ml anti-EphA2 antibody (Upstate, Lake Placid, N.Y.) overnight at 4° C., detected with 1 µg/ml HRP-conjugated anti-mouse IgG (Amersham, Piscataway, N.J.), and developed using enhanced chemiluminescence detection kit (ECL, Pierce). Membranes were tested for β-actin (0.1 µg/ml anti-β-actin primary antibody (Sigma) to confirm equal loading.

Immunohistochemistry.

Formalin-fixed, paraffin embedded sections were deparaffinized by sequential washing with xylene, 100% ethanol, 95% ethanol, 80% ethanol, and PBS. Antigen retrieval was performed by heating in steam cooker in 0.2 M tris HCl (pH 9.0) for 20 minutes. After cooling and PBS wash, endogenous peroxide was blocked with 3% $H_2O_2$ in methanol for 5 mins. Nonspecific proteins and exposed endogenous mouse IgG antibodies were blocked with 0.13 µg/ml mouse IgG Fc blocker (Jackson Laboratory, Bar Harbor, Me.) in 0.5% blocking agent (TSA biotin system kit, Perkin Elmer, Boston, Mass.) overnight at 4° C. Slides were incubated in primary antibody, 5 µg/ml of mouse anti-EphA2 clone EA5, a kind gift of Dr. Michael Kinch (MedImmune, Inc., Gaithersburg, Md.) for 4 hrs at 4° C., washed, followed by 1.5 µg/ml biotinylated horse anti-mouse (Vector Labs, Burlingame, Calif.) for 1 hr at room temperature. The secondary antibody signal was enhanced with 0.75 µg/ml streptavidin-HRP (DakoCytomation, Carpinteria, Calif.) for 30 minutes, detected with DAB (Phoenix Biotechnologies, Huntsville, Ala.) substrate for 7 minutes, and counterstained with Gil No. 3 hematoxylin (Sigma) for 20 secs.

Statistical Considerations.

For in vivo therapy experiments, 10 mice in each group were used, as directed by a power analysis to detect a 50% reduction in tumor size (beta error 0.8). Mean tumor size was analyzed for statistical significance (achieved if $p<0.05$) with student's t-test if values were normally distributed, otherwise with the Mann-Whitney rank sum test, using STATA 8 software (College Station, Tex.).

II. Results

Since its description in C. elegans (Fire, 1998) and mammalian cells (Elbashir, 2001), use of short interfering RNA (siRNA) as a method of gene silencing has rapidly become a powerful tool in protein function delineation, gene discovery, and drug development (Hannon, 2004). The promise of specific RNA degradation has also generated much excitement for possible use as a therapeutic modality, but in vivo siRNA delivery has proven difficult (Ryther, 2005). Delivery methods that are effective for other nucleic acids are not necessarily effective for siRNA's (Hassani, 2005). Therefore, most studies using siRNA in vivo involve manipulation of gene expression in a cell line prior to introduction into an animal model (Brummelkamp, 2002; Yang, 2003), or incorporation of siRNA into a viral vector (Xia, 2002; Devroe, 2004). Delivery of "naked" siRNA in vivo has been restricted to site-specific injections or through high-pressure means that are not clinically practical. The only study to show in vivo uptake and target downregulation of an endogenous protein after normal systemic dosing required chemical modulation of siRNA that will have unknown toxicities, and may affect siRNA activity or longevity (Soutschek, 2004).

The inventors have used an ovarian cancer xenograft mouse model to examine the efficacy of in vivo gene silencing by siRNA. Ovarian cancer is associated with the highest mortality among all gynecologic malignancies, with an estimated 22,220 cases and 16,210 deaths in the United States in 2005 (Jemal, 2005). The majority of ovarian cancer patients respond to initial therapy of tumor cytoreductive surgery and platinum-based chemotherapy, but of these about 70% will recur and succumb to disease. Therefore, novel therapeutic strategies are urgently needed to improve the outcome of women with ovarian cancer. Fortunately, ovarian cancer has a favorable mouse model. Intraperitoneally injected ovarian cancer cells form tumors resembling human cancer in growth pattern, and their response to therapy tends to be predictive of response in human patients (Voskoglou-Nomikos, 2003).

EphA2 is a tyrosine kinase receptor in the ephrin family that plays a key role in neuronal development (Daniel, 1996; Flenniken, 1996). In adults, it is expressed to a low degree, primarily in epithelial cells (Sulman, 1997). Several investigators have reported EphA2 overexpression in human cancers (Nemoto, 1997; Walker-Daniels, 1999; Ogawa, 2000; Kinch, 2003), and the inventors have shown that the high rate of overexpression in ovarian cancer is associated with poor clinical outcome Thaker, 2004). EphA2 can function as an oncoprotein (Zelinski, 2001), and downregulation reduces tumorigenicity in preclinical studies of breast and pancreatic cancer (Noblitt, 2004; Dobrzanski, 2004; Duxbury, 2004), making it an ideal therapeutic target.

The inventors have previously used liposomes composed of the neutral lipid DOPC (1,2-Dioleoyl-sn-Glycero-3-Phosphatidylcholine) to deliver antisense oligonucleotides in vivo (Gutierrez-Puente, 1999). Here, the inventors sought to determine the feasibility and effectiveness of delivering EphA2-targeting siRNA in DOPC. Therapeutic delivery of siRNA directed against EphA2 resulted in decreased protein expression in the tumor, and remarkably decreased tumor growth when combined with chemotherapy in an orthotopic mouse model of ovarian cancer.

Incorporation of siRNA into Liposomes.

An efficient delivery vehicle is necessary for in vivo delivery. Cationic liposomes, while efficiently taking up nucleic acids, have had limited success for in vivo gene downregulation, perhaps because of their stable intracellular nature and resultant failure to release siRNA contents. DOPC was selected because the inventors have successfully used this molecule to deliver antisense oligonucleotides in vivo (Gutierrez-Puente, 1999). When mixed together, greater than 90% of liposomes spontaneously incorporate fluorescent-tagged siRNA when microscopically examined for fluorescence. To estimate the quantity of siRNA not taken up by liposomes, free siRNA was separated from liposomes by column filtration, and siRNA measured by spectrophotometry. It is estimated that about 65% of the siRNA is incorporated into liposomes. The inventors have observed that the liposomal-nucleic acid complexes are stable for at least 4 weeks when stored at $-20°$ C.

Delivery of siRNA into Orthotopically Implanted Ovarian Tumor.

In order to examine whether siRNA could be effectively delivered into tumor cells, the inventors utilized a non-silencing siRNA tagged with the fluorochrome Alexa-555 in DOPC complexes. Mice with HeyA8 orthotopic tumors (15 days after intraperitoneal inoculation of tumor cells, FIG. 1A) were intravenously injected with 5 μg of DOPC-conjugated non-silencing siRNA/Alexa-555. Tumors were harvested at 1 hr, and 4, 7, or 10 days and examined for fluorescence. As early as one hour after injection, punctuated emissions of the siRNA were noted in the perinuclear region of individual cells (FIG. 1C) that were absent in the emission pattern of tumor injected with non-fluorescent siRNA (FIG. 1B). SiRNA was seen in 80% of 40× fields examined, and an estimated 30% of all tumor cells. Fluorescence was present in both regions immediately adjacent to the vasculature, and also deep into the tumor bed, as indicated by CD31 immunofluorescent co-localization. Furthermore, this method also demonstrated delivery of siRNA into vascular endothelial cells.

To confirm that the siRNA was present in tumor cells, and not simply scavenged by macrophages, separate slides were stained for f4/80 to identifying scavenging macrophages. These macrophages are seen to surround nests of tumor cells that contain perinuclear siRNA, and have about the same rate of siRNA uptake as tumor cells (FIG. 1D), suggesting that siRNA is delivered directly into the tumor cells. To confirm that the fluorescent signal was not a contaminating secondary antibody or an artifact of processing, 30 μm sections were examined with confocal microscopy. This technique permitted signal detection within the middle of tissue, rather than from surface emissions alone. After evaluating emissions at multiple depths, a 3-dimensional cross section was created. Lateral views clearly demonstrate the presence of fluorescently tagged siRNA within tissue parenchyma (FIG. 1E). In this view, fluorescent emission from macrophage staining (green) was noted only at the surface, since the detecting antibody is too large to penetrate tissue. Emission from nuclear staining (blue) is the result of a dye (Hoescht) small enough to penetrate tissue. Tumors collected at 4, 7, and 10 days after a single injection were also noted to have comparable distribution of siRNA within the tumor. Because this fluorescently-tagged siRNA is a non-specific construct, longevity after administration of an mRNA-targeting construct is likely to be of shorter duration.

Administration of siRNA complexed with DOTAP showed sporadic presence of fluorescence within tumor tissue (7% of all fields examined). However, the observed fluorescence was primarily adjacent to CD31 positive endothelial cells (shown green in FIG. 1F), bringing into question whether the liposomal contents were released, or trapped in the vasculature. After administration of naked fluorescent siRNA (without liposomal encapsulation), fluorescence was rarely observed (2% of 40× fields, <1% of cells, FIG. 1G), although notably present in the desired perinuclear location in positive cells. Therefore, the DOPC liposome preparation was associated with an estimated 10-fold improvement in delivery of siRNA compared to DOTAP, and 30-fold improvement over naked siRNA.

Tissue Distribution of siRNA Throughout Vital Organs.

In order to examine the distribution in other organs, sections of the liver, kidney, spleen, heart, lung, and brain were examined for fluorescence after a single-dose of Alexa-555-siRNA in DOPC. Specimens from mice treated with nonfluorescent siRNA were examined to determine background fluorescence. There was significant siRNA uptake and cytoplasmic distribution in the liver, kidney, and lung (FIG. 2A, FIG. 2B, and FIG. 2C, respectively). There was a small amount of uptake in the heart, but significantly greater than that of untreated heart tissue. The fluorescence emitted by endogenous protein products in the spleen, pancreas, and brain made evaluation more difficult, and precludes a definitive conclusion that liposomes are incorporated in these tissues.

Similar patterns of uptake after DOTAP-complexed and naked siRNA administration were seen in other organs as was seen in the tumor. DOTAP complexes formed multiple large fluorescent signals near the vasculature without perinuclear punctuations in the liver. There was a high level of uptake in the kidney, both near the vasculature in large signals and by individual cells. Naked siRNA administration did result in uptake by a large percentage of liver and kidney cells, but the fluorescent signal was greatly decreased compared to uptake by DOPC-complexed siRNA.

Downregulation of EphA2 with Liposomal siRNA.

The inventors have previously shown that EphA2 is overexpressed by a large percentage of patients with ovarian cancer, and that overexpression is predictive of poor outcome (Thaker, 2004). Furthermore, this protein has low relative expression in the adult, and so is an attractive tumor selective target. Therefore, the inventors used EphA2 as a model to test the efficacy of siRNA therapy. In vitro, both HeyA8 and SKOV3ip1 ovarian cancer cell lines transfected with EphA2 siRNA demonstrated a 95% decrease in EphA2 expression compared to transfection with control siRNA, as determined by Western blot analysis (data not shown). Subsequently, the inventors tested the ability of DOPC liposomal siRNA to silence EphA2 in an orthotopic in vivo model. EphA2-targeting siRNA-DOPC was given to tumor-bearing mice, and tumor collected at various timepoints. Measurement of EphA2 by Western blot of tumor lysate (FIG. 3A) and by immunohistochemistry (FIG. 3D) showed that tumor collected 48 hrs following administration of single dose anti-EphA2 siRNA had significantly decreased EphA2 expression compared to treatment with a nonspecific siRNA (FIG. 3B) or naked siRNA (FIG. 3C). Expression of EphA2 remained suppressed at 4 days, was higher after 7 days, and had returned to normal levels by 10 days. Therefore, the inventors used twice-weekly dosing of anti-EphA2 siRNA for subsequent therapy experiments.

In Vivo Therapy Experiments with Liposomal Anti-EphA2 siRNA.

Female nude mice (n=50 per cell line, 10 per group) were injected with HeyA8 or SKOV3ip1 cells into the peritoneal cavity. One week after tumor cell injection, animals were randomly allocated to five treatment groups: 1) empty liposomes, 2) nonspecific siRNA-DOPC, 3) EphA2-targeted siRNA-DOPC, 4) paclitaxel and non-specific siRNA-DOPC, and 5) paclitaxel and EphA2-targeting siRNA-DOPC. After 4 weeks of therapy, the animals were sacrificed and necropsies performed. Tumors were excised and weighed. Treatment with anti-EphA2 siRNA, paclitaxel plus control siRNA, and paclitaxel plus anti-EphA2 siRNA were all effective in reducing tumor size, with combination therapy leading to 86-91% reduction compared to treatment with control siRNA alone (FIG. 4A, FIG. 4B). Targeting EphA2 with siRNA alone diminished tumor growth in both lines when compared to control siRNA alone (HeyA8: 0.98 g v. 1.51 g, respectively, p=0.155; SKOV3ip1: 0.35 g v. 0.70 g, respectively, p=0.020). EphA2-targeting siRNA in combination with paclitaxel significantly reduced tumor growth as compared to nonspecific siRNA and paclitaxel (HeyA8: 0.21 g v. 0.84 g, respectively, p<0.003; SKOV3ip1: 0.04 g v. 0.22 g, respectively, p<0.001). This pattern of tumor growth inhibition (moderate inhibition with EphA2 targeting alone, marked inhibition in combination with paclitaxel) is similar to that seen with antibody-based EphA2-downregulation in this mouse model (data not shown). Interestingly, administration of nonspecific siRNA-DOPC resulted in some reduction in tumor growth, though statistically significant only in the HeyA8 model, when compared to empty liposomes. These data may support prior reports that siRNA without a specific mRNA target may have nonspecific effects that affect tumor growth (Hannon, 2004), and further supports the inventors' hypothesis that siRNA-DOPC is delivered to the tumor parenchyma.

No toxicities were observed by behavioral changes such as eating habits and mobility in animals treated with liposomal siRNA preparations, both those that are non-silencing, and those targeting EphA2. Mouse weights were not significantly different among the five groups of animals, suggesting eating and drinking habits were not affected. Organ sections were reviewed by a board-certified pathologist, and after five weeks of therapy no histologic toxicities were detected in the liver, kidney, heart, lung, or brain. A slight increase in the size of the white pulp of the spleen was noted in all four siRNA groups, which may be indicative of a general inflammatory response.

In this study, the inventors describe the therapeutic delivery of gene specific siRNA using DOPC liposomes. These studies collectively demonstrate the direct delivery, gene targeting, and growth attenuation after systemic delivery of siRNA in an orthotopic model of ovarian cancer. The significance of this work is that packaging of siRNA into liposomes is rapidly transferable to a clinical setting. Prior to the work presented herein, the most successful and reproducible systemic delivery of siRNA in vivo had been rapid injection of high volume of material (i.e. 2 mL into a mouse with estimated 4 mL total blood volume), hydrodynamically forcing siRNA into the liver (McCaffrey, 2002). Such techniques would not be feasible in a clinical setting, whereas liposomes have been used extensively clinically for chemotherapy and other delivery systems.

Because delivery in this study was efficient to other vital organs, most notably in the liver and kidney, this method may be used in non-cancerous conditions shown to be amenable to siRNA therapy in preclinical models such as viral hepatitis (McCaffrey, 2002; Devroe, 2004) and HIV (Lori, 2002). However, this mode of delivery is not tissue specific, so it will be important that the gene chosen to downregulate with siRNA is not crucial to function by normal cells. Alternatively, further modifications of the liposome may allow tumor-selective delivery (Park, 1997; Dubey, 2004).

The first demonstration that siRNA had activity in vivo was in the hydrodynamic injection of naked siRNA that effectively decreased luciferase expression in the livers of mice (McCaffrey, 2002). Along with confirmatory reports of high-pressure intravenous injection (Lewis, 2002; Klein, 2003), others have shown that siRNA has activity in vivo using delivery in viral vectors (Xia, 2002; Devroe, 2004), retinal electroporation Matsuda, 2004), and direct intracellular (Wianny, 2000), intratumoral (Uchida, 2004), intravitreal (Reich, 2003), intanasal (Zhang, 2004), and intrathecal (Dorn, 2004) administration. While these methods are useful in a preclinical setting, their delivery methods and the climate of viral gene therapy make clinical applicability limited.

Sorensen and colleagues effectively reduced TNF-α expression in the liver and spleen by delivering siRNA packaged in cationic liposomes (DOTAP), protecting mice from a lethal dose of LPS (Sorensen, 2003). The inventors have found that DOTAP accumulates near the vasculature, and is preferentially taken up by the liver and spleen, limiting its effectiveness in systemic or anti-tumor therapy. Soutscheck and colleagues have reported that siRNA conjugated with cholesterol improved delivery to multiple organs, and that downregulation of ApoB was achieved in liver and jejunum (Soutschek, 2004). However, the effects of cholesterol conjugation on siRNA activity and duration of effect, efficiency of uptake in tumors, and toxicities are not known. Duxbury and associates have shown that systemic delivery of naked siRNA targeting FAK (Duxbury, 2003), EphA2 (Duxbury, 2004), or CEACAM6 (Duxbury, 2004) downregulated protein expression and decreased growth of a single subcutaneously-injected malignant pancreatic cell line. It is possible that naked siRNA may be effectively delivered to subcutaneous sites, but not to orthotopic sites, as supported by these results.

Recent studies suggest that the specificity of siRNA may not be as absolute as initially hoped. An analysis of gene expression profiling suggested that RNA downregulation might occur with as few as 11 complementary base pairs within the 21-base pair siRNA sequence (Jackson, 2003). Therefore, in siRNA design a BLAST search for cross-reactive 21-base pair sequences is insufficient to have confidence that the mRNA of interest is the only target. Furthermore, siRNA's may bind mRNA of only near-perfect complementarity, and prevent translation without degradation (Lewis, 2003). This is the mechanism used by endogenously-produced microRNA's (miRNA), believed to be another method of natural regulation of gene expression (Ambros, 2004). Crossover of siRNA into the miRNA pathway or downregulation by partial homology seem to be minimal and require participation of several siRNA sequences, but this potential should caution conclusions made regarding the specificity of gene downregulation. Another level of questionable specificity of siRNA introduction lies in activation of the innate immune system. SiRNA therapy has, in some circumstances, been shown to activate interferon (Kim, 2004; Sledz, 2003). Of course, in the treatment of cancer, interferon induction may be of additional benefit, as long as toxicities are limited. This is supported by the finding presented herein that therapy with a non-specific siRNA construct results in some reduction in tumor growth compared to empty liposomes.

Toxicities of liposomes are believed to be limited. Liposomal chemotherapy is routinely used in treatment of ovarian and other cancers (Gabizon, 2001). In a phase I trial with cationic liposomes carrying adenoviral vectors (encoding the E1A gene), fever and pain three hours after treatment were the dose-limiting toxicities (Hortobagyi, 2001). Although this is the best estimation of side effects the inventors can currently predict, delivery of siRNA is less likely to be recognized as foreign, and host response will almost certainly differ.

The charge of the liposome affects the tissue specificity of liposomal uptake. Macrophages seem to preferentially take up negatively-charged liposomes (Miller, 1998). Different malignant cell lines have varying uptake patterns regarding positive, neutral, or negative charges, and in vivo uptake patterns may differ further (Miller, 1998). Liposomal makeup also influences cellular toxicity, with siRNA delivery using a liposome with a higher proportion of neutral lipids leading to less cellular toxicity without compromising ability to downregulate gene expression in vitro (Spagnou, 2004). Clearly, a complete understanding of the best liposomal makeup for delivery of therapeutic substances is still evolving. It is possible that with siRNA delivery, the use of a neutral lipid such as DOPC allows a balance between efficient uptake of the siRNA into a liposome at preparation, uptake of the liposome into a cell, and breakdown of the intracellular liposome with release of siRNA contents into the cytoplasm.

In vivo delivery of siRNA in experimental models has been demonstrated provides feasibility for use in humans. Liposomal delivery of drugs is established and safe, and their use for siRNA delivery may make this therapeutic modality clinically attractive. The inventors have shown that using DOPC-complexed siRNA allows delivery to tumor and other tissues, with corresponding gene targeting and reduced tumor growth. With further study and a cautious approach, this is a model that can be taken into a clinical setting for cancer therapy, as well as for other conditions amenable to specific gene downregulation.

Example 2

FAK Targeting and Combination Therapy

1. Materials and Methods
   Cell Lines and Cultures.
   The derivation and source of established human ovarian cancer cell lines SKOV3, SKOV3ip1 and HeyA8 have been described previously. The taxane resistant cell lines, SKOV3-TR (a gift of Dr. Michael Seiden, Massachusetts General Hospital, Boston, Mass.) and HeyA8-MDR (a gift from Dr. Isaiah Fidler, Department of Cancer Biology, University of Texas M. D. Anderson Cancer Center) was also used. All cell lines were maintained and propagated in vitro by serial passage in RPMI 1640 or modified Eagle's medium, supplemented with 15% fetal bovine serum and 0.1% gentamicin sulfate (Gemini Bioproducts; Calabasas, Calif.). All in vitro experiments were conducted with 70-80% confluent cultures.

siRNA Synthesis.
siRNAs were synthesized and then purified using high-performance liquid chromatgraphy (Qiagen-Xeragon, Germantown, Md.). FAK siRNA sense: r(CCACCUGGGC-CAGUAUUAU)d(TT) (SEQ ID NO:7); antisense: r(AUAAUACUGGCCCAGGUGG)d(TT) (SEQ ID NO:8) and control siRNA sense: r(UUUUCCGAACGUGU-CACGU)dTT; (SEQ ID NO:9) antisense: r(ACGUGA-CACGUUCGGAGAA)dTT (SEQ ID NO:10) bearing no sequence homology with any known human mRNA sequences were dissolved in buffer (100 mmol/L potassium acetate, 30 mmol/L HEPES potassium hydroxide, 2 mmol/L magnesium acetate, pH 7.4) to a final concentration of 20 pmol/L, heated to 90° C. for 60 seconds, incubated at 37° C. for 60 minutes, and stored at −20° C. until future use.

Liposomal siRNA Preparation.
siRNA for in vivo delivery was incorporated into the phospholipid 1,2-dioleoyl-sn-glycero-3-phosphatidylcholine (DOPC). DOPC and siRNA were mixed in the presence of excess tertiary-butanol at a ratio of 1:10 (wt:wt), as previously described (Landen et al., 2005). Tween-20 was added to the mixture at a ratio of 1:19. The mixture was vortexed, frozen in an acetone/dry ice bath, and lyophilized. Before in vivo administration, this preparation was hydrated with normal (0.9%) saline at a concentration of 15 μg/ml to achieve the desired dose of 150-200 μl per injection. To estimate the quantity of siRNA not taken up by liposomes free siRNA was separated from liposomes by using filter units with a 30,000 nominal molecular weight limit (Millipore Corp, Billerica, Mass.). The liposomal suspension was added to the filters and centrifuged at 5,000 g for 40 min at room temperature. Fractions were collected, the material trapped in the filter was reconstituted with 0.9% saline, and the amount of siRNA in the collected fraction and eluent were measured by spectrophotometry.

Reagents.
Leupeptin, aprotinin, and sodium orthovanadate were obtained from Sigma Aldrich (St. Louis, Mo.), EDTA from Gibco-Invitrogen (Carlsbad, Calif.) docetaxel from Sanofi-Aventis (Bridgewater, N.J.), and cisplatin from LKT Laboratories. Primary antibodies used were mouse anti-FAK (Biosource International Camarillo, Calif.), mouse anti-proliferating cell nuclear antigen (PCNA) clone PC 10 (Dako A/S, Copenhagen, Denmark) and mouse anti-CD31 (Pharmingen, San Diego, Calif.). The following secondary antibodies were used for colorimetric immunohistochemical (IHC) analysis: horseradish peroxidase (HRP)-conjugated goat anti-rabbit immunoglobulin G (IgG); F(ab)$_2$ Jackson ImmunoResearch Laboratories, Inc., (West Grove, Pa.); biotinylated mouse antigoat (Biocare Medical, Walnut Creek, Calif.); HRP-conjugated streptavidin (Dako A/S); HRP-conjugated rat antimouse IgG2a (Serotec, Harlan Bioproducts for Science, Inc., Indianapolis, Ind.); HRP-conjugated goat anti-rat IgG (Jackson ImmunoResearch Laboratories, Inc., West Grove, Pa.) and fluorescent Alexa 488-conjugated goat antirabbit IgG (Molecular Probes, Inc., Eugene, Oreg.).

Western Blot Analysis.
Cells were lysed in modified RIPA buffer (50 mM Tris, 150 mM NaCl, 1% triton, 0.5% deoxycholate plus 25 pg/ml leupeptin, 10 pg/ml aprotinin, 2 mM EDTA, and 1 mM sodium orthovanadate (Sigma Chemical Co, St. Louis, Mo.) as previously described (Sood et al., 2004; Sood et al., 2002). A sample was removed from culture dishes by cell scraping and centrifuged at 12,500 rpm for 30 min. The FAK protein concentration of the supernatant was determined using a bicinchoninic acid protein assay reagent kit (Pierce, Rockford, Ill.), and whole cell lysates were analyzed by 7.5% SDS-PAGE. Samples were then transferred to nitrocellulose membrane by semi-dry transfer (BioRad Laboratories, Hercules, Calif.). Membranes were blocked with 5% nonfat milk, and incubated with 0.25 µg/mL anti-FAK antibody (Biosource, International Camarillo, Calif.) for 1 h at room temperature. Antibody was detected with 0.167 µg/mL HRP-conjugated anti-mouse secondary antibody (The Jackson Laboratory, Bar Harbor, Me.) and developed with an enhanced chemiluminescence detection kit (Pierce). Equal loading was confirmed by detection of β-actin (0.1 µg/ml, anti-β-actin antibody, Sigma Chemical). Densitometric analysis was performed using the Scion Imaging software (Scion Corporation, Frederick, Md.).

Cytotoxicity Assay.

To determine the $IC_{50}$ concentration of cytotoxic drugs under different conditions, $2\times10^3$ cells were seeded onto 96-well plates and incubated overnight at 37° C., after which either control or FAK-targeting siRNA was added. The medium was exchanged after 48 hours with increasing concentrations of docetaxel (obtained from Aventis Pharma, Bridgewater, N.J.) dissolved in ethanol (final concentration range, 0.1-10,000 nmol/L prepared in medium) or cisplatin (purchased from LKT Laboratories, Inc., St. Paul, Minn.) dissolved in water. After a 96-hour incubation, 50 µL of 0.15% 3-(4,5-dimethylthiazol-2-yl)-2,5-diphenyltetrazolium bromide was added to each well and incubated for 2 hours. The supernatant was removed, and cells were dissolved in 100 µL DMSO. The absorbance at 570 nm was recorded using a FALCON microplate reader (Becton Dickinson Labware, Bedford, Mass.), and cell survival expressed as a percent increase or decrease above control conditions, after subtracting blank A570 readings. The $IC_{50}$ concentration was determined by finding the A570 reading midpoint between maximal and minimal readings and finding the chemotherapy concentration that intersects the growth curve at that A570 reading.

Terminal Deoxynucleotidyl Transferase-Mediated Nick End Labeling Assay.

Terminal deoxynucleotidyl transferase-mediated nick end labeling-positive cells were detected using Dead End Fluorometric terminal deoxynucleotidyl transferase-mediated nick end labeling system (APO-DIRECT, BD Biosciences/PharMingen, San Diego, Calif.) according to the manufacturer's instructions. Briefly, ovarian cancer cells in culture were treated with varying concentrations of docetaxel and harvested after 12, 24, 48, or 96 hours. Cells were fixed with 4% paraformaldehyde solution for 25 minutes on ice. Intracellular DNA fragments were then labeled by exposing cells to fluorescein-12-dUTP, treated with propidium iodide and RNaseA solution, and analyzed by flow cytometry (EPICS XL, Beckman Coulter, Miami, Fla.). The percentages of apoptotic cells were averaged over three consecutive experiments.

Caspase Activity.

Ovarian cancer cells ($1\times10^6$) in culture (six-well plates) were treated with or without docetaxel at the cell line specific $IC_{50}$ or $IC_{90}$ concentration for 24 hours. After washing with PBS, cells were lysed in 50 µL of cell lysis buffer provided. Caspase-3, caspase-8, and caspase-9 activities were measured with the appropriate apoptosis detection kit (BD Biosciences/Clontech, Palo Alto, Calif.), using substrate DEVD-AFC for caspase-3, IETD-AFC for caspase-8, and LEHD-AMC for caspase-9.

Animal Care and Orthotopic Implantation of Tumor Cells.

Female athymic nude mice (NCr-nu) were purchased from the National Cancer Institute-Frederick Cancer Research and Development Center (Frederick, Md.). The mice were housed and maintained under specific-pathogen-free conditions in facilities approved by the American Association for Accreditation of Laboratory Animal Care and in accordance with current regulations and standards of the U.S. Department of Agriculture, the U.S. Department of Health and Human Services, and the National Institutes of Health. All studies were approved and supervised by The University of Texas M.D. Anderson Cancer Center, Institutional Animal Care and Use Committee. The mice were used in these experiments when they were 8-12 weeks old.

To produce tumors, SKOV3ip1, Hey A8-MDR cells ($1\times10^6$ cells/0.2 ml of HBSS) and Hey A8 cells ($2.5\times10^5$ cells/0.2 ml of HBSS) were injected interperitoneally (i.p.) into the mice. For in vivo injections, cells were trypsinized and centrifuged at 1000 rpm for 7 minutes at 4° C., washed twice with PBS and reconstituted in serum-free Hank's balanced salt solution (HBSS, Life Technologies, Carlsbad, Calif.). Only single-cell suspensions with >95% viability, as determined by trypan blue exclusion, were used for the in vivo injections. Mice (n=10 per group) were monitored for adverse effects of therapy and were sacrificed on day 35 (SKOV3ip1) or day 28 (HeyA8 or HeyA8-MDR) or when any of the mice began to appear moribund. Mouse weight, tumor weight, and tumor distribution were recorded. Tissue specimens were snap frozen for lysate preparation, fixed in formalin for paraffin embedding or frozen on OCT compound (Miles, Inc., Elkhart, Ind.) for frozen slide preparation.

Therapy for Established Human Ovarian Carcinoma in the Peritoneal Cavity of Nude Mice.

To evaluate the therapeutic effect of the combination of FAK siRNA and docetaxel in a mouse model, preliminary dose-response studies were performed experiments for FAK siRNA. HeyA8 cells were implanted i.p. and treatment was initiated 21 days following tumor injection when i.p. tumors could be assessed by palpation. Mice were randomly distributed into three groups (n=10 per group) and were treated with a single dose of PBS, control siRNA or FAK siRNA at 150 µg/kg in 200 µl volume. Following treatment, 3 mice were sacrificed at definite time-points (24 h, 48 h, 96 h and 6 days). Fluorescent IHC analysis was performed on any excised peritoneal cavity tumors as described below.

Based on the results of preliminary dose-response studies, a series of three separate therapy studies were initiated using the optimal FAK siRNA dosage. Tumor cells were injected i.p. and 7 days later, the mice were randomly assigned to five treatment groups: empty liposome twice weekly, non-specific control FAK siRNA (3 µg) twice weekly, control FAK siRNA (3 µg) twice weekly in combination with 50 µg docetaxel weekly, FAK siRNA twice weekly and FAK siRNA (3 µg) twice weekly in addition to 50 µg docetaxel weekly.

Immunohistochemical Determination of PCNA and CD31.

Expression of PCNA was determined by IHC analysis using paraffin-embedded tumors. Sections (8-µm thick) were deparaffinized in xylene, treated with a graded series of alcohol [100%, 95%, 80% ethanol/double distilled $H_2O$ (v/v)], and rehydrated in PBS (pH 7.5). Antigen retrieval was performed by microwave heating for 5 minutes in 0.1 M citrate buffer pH 6.0, followed by blocking of endogenous peroxide with 3% $H_2O_2$ in methanol for 5 min. After PBS wash ×2, slides were blocked with 5% normal horse serum and 1% normal goat serum in PBS for 15 min at room temperature, followed by incubation with primary antibody (anti-PCNA, PC-10, mouse IgG, Dako), in blocking solution overnight at 4° C. After two PBS washes, the appropriate secondary antibody conjugated to horseradish peroxidase, in blocking solution, was added for 1 hour at room temperature. HRP was detected with DAB (Phoenix Biotechnologies, Huntsville, Ala.) substrate for 5 minutes, washed, and counterstained with Gil No. 3 hematoxylin (Sigma) for 20 sec. IHC for CD31 was performed on freshly cut frozen tissue. These slides were fixed in cold acetone for 10 minutes, and did not require antigen retrieval. The primary antibody used was anti-CD31 (PECAM-1, rat IgG, Pharmingen). Staining for PCNA and CD31 was conducted on tumors collected at the conclusion of 4 week therapy trials. Control samples exposed to secondary antibody alone showed no specific staining.

Quantification of Microvessel Density (MVD), PCNA, and TUNEL Positive Cells.

To quantify MVD, 10 random 0.159-mm$^2$ fields at ×100 final magnification were examined for each tumor (1 slide per mouse, 5 slides per group), and the number of microvessels per field were counted. A single microvessel was defined as a discrete cluster or single cell stained positive for CD31 (CD31), and the presence of a lumen was required for scoring as a microvessel. To quantify PCNA expression, the number of positive cells (DAB staining) was counted in 10 random 0.159-mm$^2$ fields at ×100 magnification. To quantify TUNEL positive cells, the number of green fluorescence positive cells was counted in 10 random 0.01-mm$^2$ fields at ×400 magnification.

Microscopic Analysis.

3,3-Diaminobenzidine-stained sections were examined with a 10× objective on a Microphot-FX microscope (Nikon, Garden City, N.Y.) equipped with a three-chip charge-coupled device color video camera (model DXC990; Sony, Tokyo, Japan). Immunofluorescence microscopy was performed using a 20× objective on a Microphot-FXA microscope (Nikon) equipped with on HBO 100 mercury lamp and narrow band pass filters to individually select for green, red, and blue fluorescence (Chroma Technology, Brattleboro, Vt.). Images were captured using a cooled charge-coupled device camera (model 5810; Hamamatsu, Bridgewater, N.J.) and Optimas Image Analysis software (Media Cybernetics, Silver Spring, Md.). Photomontages were prepared using Micrografx Picture Publisher (Corel, Dallas, Tex.) and Adobe Photoshop software (Adobe Systems, Inc., San Jose, Calif.). Photomontages were printed on a digital color printer (Model UP-D7000; Sony).

Statistical Analyses.

For the in vivo experiments, differences in continuous variables (mean body weight, tumor weight, MVD, PCNA) were analyzed using Student's t-test for comparing two groups and by ANOVA for multiple group comparisons with a p-value less than 0.05 considered statistically significant. For values that were not normally distributed, the Mann-Whitney rank sum test was used. The Statistical package for the Social Sciences (SPSS: SPSS Inc., Chicago, Ill.) was used for all the statistical analyses.

IHC Determination of PCNA and CD31.

Expression of PCNA was determined by IHC analysis using paraffin-embedded tumors. Sections (8-μm thick) were mounted on positively charged Superfrost slides (Fisher Scientific Co., Houston, Tex.) and dried overnight. Sections were deparaffinized in xylene, treated with a graded series of alcohol [100%, 95%, 80% ethanol/double distilled H$_2$O (v/v)], and rehydrated in PBS (pH 7.5). Antigen was retrieved by placing the slides in water and then boiling them in a microwave on high power for 5 min. Expression of CD31 was determined using fresh frozen tissues that were cut into 4-μm thick sections and mounted on positively charged slides. The slides were stored at −80° C.; sections were fixed in cold acetone for 10 min. and then washed twice with PBS for 3 min each time. A positive reaction was visualized by incubating the slides with stable 3,3 diaminobenzidine for 10-20 min. The sections were rinsed with distilled water, counterstained with Gill's hematoxylin for 1 min and mounted with Universal mount (Research Genetics). Control samples exposed to secondary antibody alone showed no specific staining.

II. Results

In Vitro Sensitivity of Ovarian Cancer Cell Lines to Docetaxel.

The inventors first analyzed the effect of docetaxel on the growth of ovarian cancer cell lines by using the 3-(4,5-dimethylthiazol-2-yl)-2,5-diphenyltetrazolium bromide assay at doses ranging from 0.1 to 10,000 nmol/L. Growth of ovarian cancer cells was inhibited in a dose-dependent manner (FIG. 5). The IC$_{50}$ levels for the SKOV3 and HeyA8 cells were 6.2 and 1 mmol/L, respectively. The IC$_{50}$ levels for SKOV3-TR and HeyA8-MDR were 225 and 450 nmol/L, respectively (FIG. 5). Therefore, the SKOV3-TR and HeyA8-MDR cell lines were 36- and 300-fold more resistant to docetaxel, respectively.

Caspase Activity Increases with Docetaxel Therapy.

Caspase activity is known to play an important role in cisplatin mediated apoptosis, with caspase-8 and caspase-9 as initiators and caspase-3 and caspase-7 as executors (Thornberry and Lazebnik, 1998). Thus, the inventors assayed caspase-3, caspase-8, and caspase-9 by testing the conversion of the substrates DEVD-AFC (caspase-3), IETD-AFC (caspase-8), and LEHD-AMC (caspase-9) into free AFC (for caspase-3 and caspase-8) and AMC (for caspase-9) after treatment with docetaxel using both IC$_{50}$ and IC$_{90}$ levels (FIG. 6). Cisplatin was used as a positive control. Caspase-3 activity increased in a dose-dependent manner in the SKOV3 (2.8-fold with IC$_{50}$ and 5.4-fold with IC$_{90}$ levels of docetaxel) and HeyA8 (1.8-fold with IC$_{50}$ and 2.5-fold with IC$_{90}$ levels of docetaxel) cell lines. Caspase-8 activity increased by 2.8- to 3-fold in SKOV3 cells and by 2.8- to 2.9-fold in HeyA8 cells. Caspase-9 activity increased by 1.35- to 1.64-fold in SKOV3 and 1.5- to 1.6-fold in HeyA8 cells. In contrast, docetaxel treatment (using IC$_{50}$ and IC$_{90}$ levels for sensitive cell lines) was not able to induce caspase activity in the resistant cell lines SKOV3-TR and HeyA8-MDR.

Focal Adhesion Kinase is Cleaved in Response to Docetaxel.

Figures 7A, 7B:
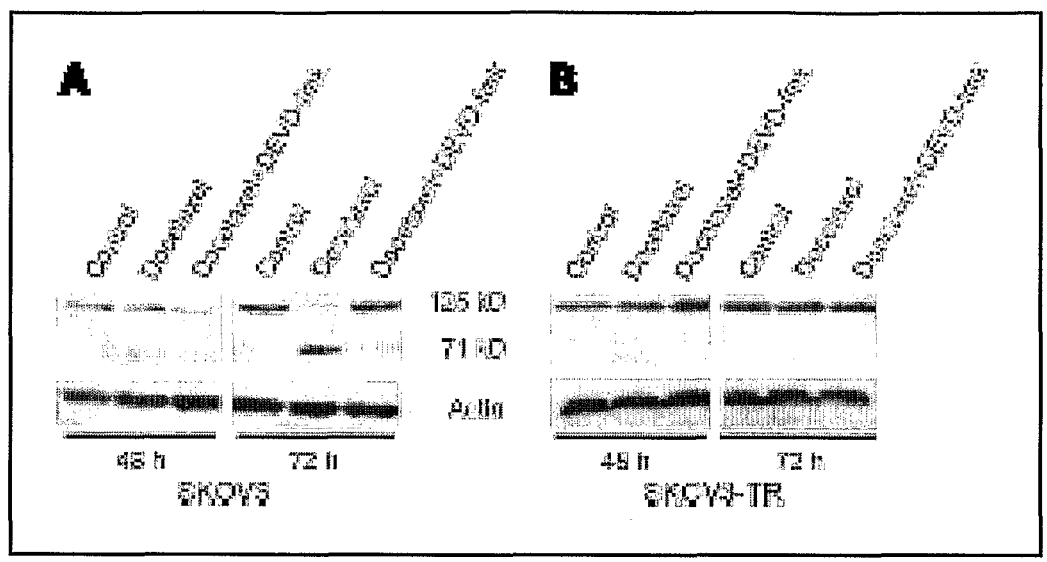
FIGS. 7A-7B. Docetaxel treatment results in FAK cleavage. The taxane-sensitive (A) and taxane-resistant (B) SKOV3 cells were cultured in the presence of docetaxel for 48 or 72 hours. Western blot analysis for FAK in SKOV3 and SKOV3-TR cells in the presence or absence of the caspase-3 inhibitor DEVD-fmk.

It has been reported that FAK may be cleaved by caspase-3 (Gervais et al., 1998; Sasaki et al., 2002; Carragher et al., 2001). Based on observations regarding modulation of caspase levels by docetaxel in ovarian cancer cells, FAK cleavage after treatment with docetaxel was examined and whether there are differences in extent of FAK cleavage between the taxane-sensitive and taxane-resistant cell lines. In SKOV3 cells, FAK was cleaved after 48 and 72 hours of exposure to docetaxel (FIG. 7A). The 71-kDa fragments increased after treatment with docetaxel, whereas the 125-kDa fragments decreased. Similar findings were observed with the HeyA8 cells (data not shown). However, taxane-resistant SKOV3-TR and HeyA8-MDR cells did not show any increase in FAK cleavage products after treatment with docetaxel (FIG. 7B). To study the dependence of FAK cleavage on caspase-3, the effect of DEVDfmk (caspase-3 inhibitor) was examined. In the presence of DEVD-fmk, docetaxel-induced FAK cleavage was blocked. These results suggest that docetaxel-mediated FAK cleavage occurs via caspase-3.

Focal Adhesion Kinase is Down-Regulated with Focal Adhesion Kinase-Specific Small Interfering RNA.

Figures 8A, 8B, 8C, 8D, 8E:
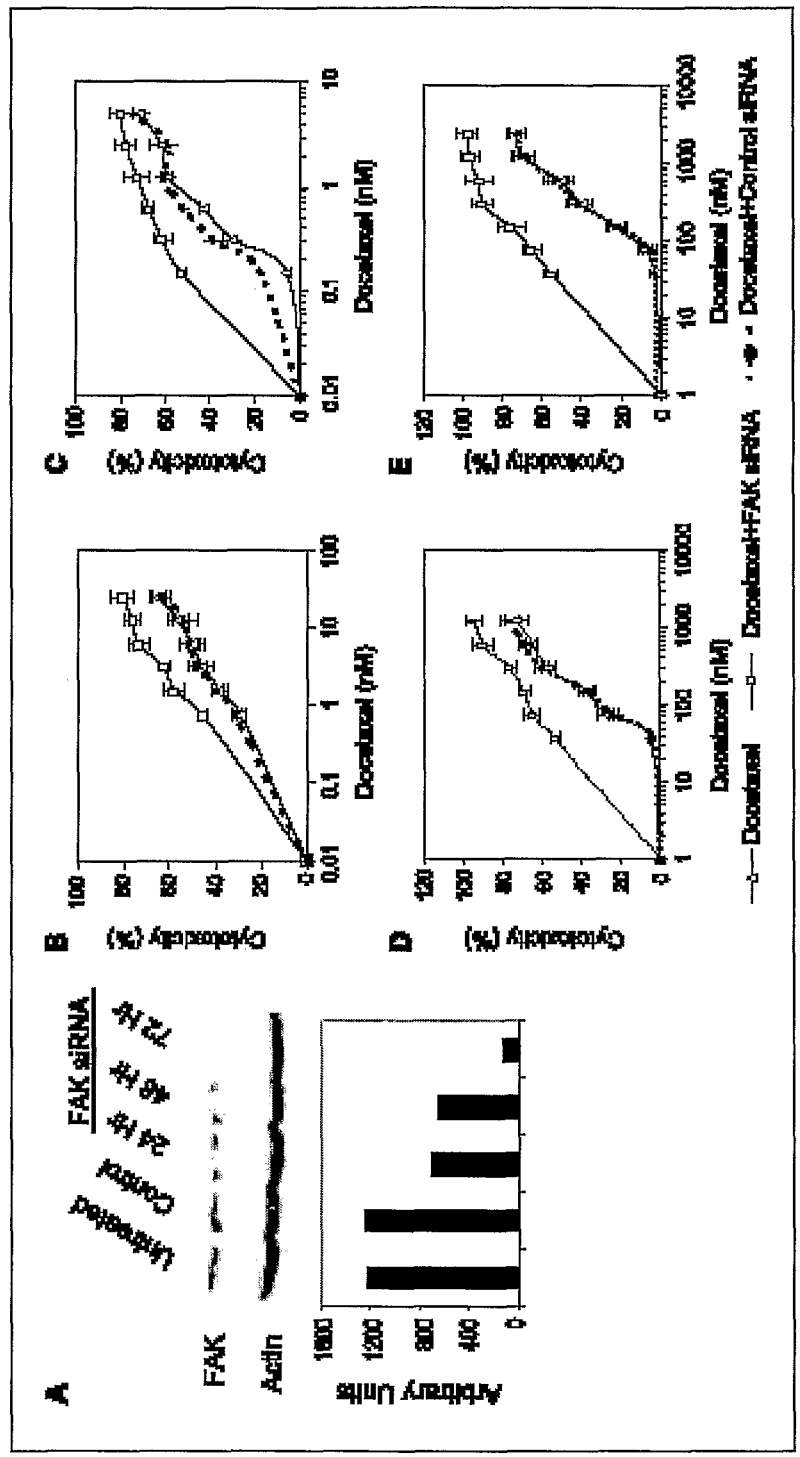
FIGS. 8A-8E. Effect of FAK silencing on docetaxel-sensitivity in ovarian cancer cell lines. (A) Western blot analysis of SKOV3 whole-cell lysates probed with anti-FAK and anti-actin monoclonal antibodies. Bottom, densitometry results. Control siRNA did not significantly affect FAK expression compared with untreated cells whereas FAK-specific siRNA resulted in >90% suppression of FAK expression by 72 hours. Effects of docetaxel on (B) SKOV3, (C) HeyA8, (D) SKOV3-TR, and (E) HeyA8-MDR growth were tested alone or in combination with FAK siRNA or control siRNA. Points, means of three independent experiments; bars, SE.

Next, the inventors sought to examine whether FAK silencing using siRNA will sensitize ovarian cancer cells to docetaxel. First transfection conditions were optimized for these cells lines by testing various ratios of rhodamine-conjugated nonsilencing siRNA to RNAifect Reagent (μg/μL) and determined that a ratio of 1:6 was optimal and resulted in about 90% transfection efficiency. Treatment with FAK siRNA, but not control (nonsilencing) siRNA, resulted in a detectable decrease in FAK expression after 24 hours of treatment and maximal suppression of 90% after 72 hours of transfection (FIG. 8A). Actin expression was unaffected by either control or FAK siRNA treatment, indicating that nonspecific down-regulation of protein expression did not occur.

Focal Adhesion Kinase Down-Regulation Sensitizes Ovarian Cancer Cells to Docetaxel.

The effect of FAK silencing using siRNA on in vitro sensitivity of human ovarian cancer cells to docetaxel was determined. Ovarian cancer cells were exposed to FAK siRNA or a nonsilencing siRNA for 48 hours before treatment with increasing concentrations of docetaxel. The fold differences were calculated at the point where 50% cytotoxicity was observed. Docetaxel cytotoxicity was almost 5-fold greater after FAK down-regulation in SKOV3 and 8-fold greater in HeyA8 cells (FIGS. 8B and 8C). Next, the effects of FAK silencing in the taxane-resistant SKOV3-TR and HeyA8-MDR cells was examined. Similar findings were observed with the resistant cell lines (4.8-fold increase in sensitivity in SKOV3-TR and 5.5-fold increase in HeyA8-MDR cells; FIGS. 8D and 8E). Control siRNA treatment did not affect sensitivity of ovarian cancer cells to docetaxel.

Figures 9A, 9B:
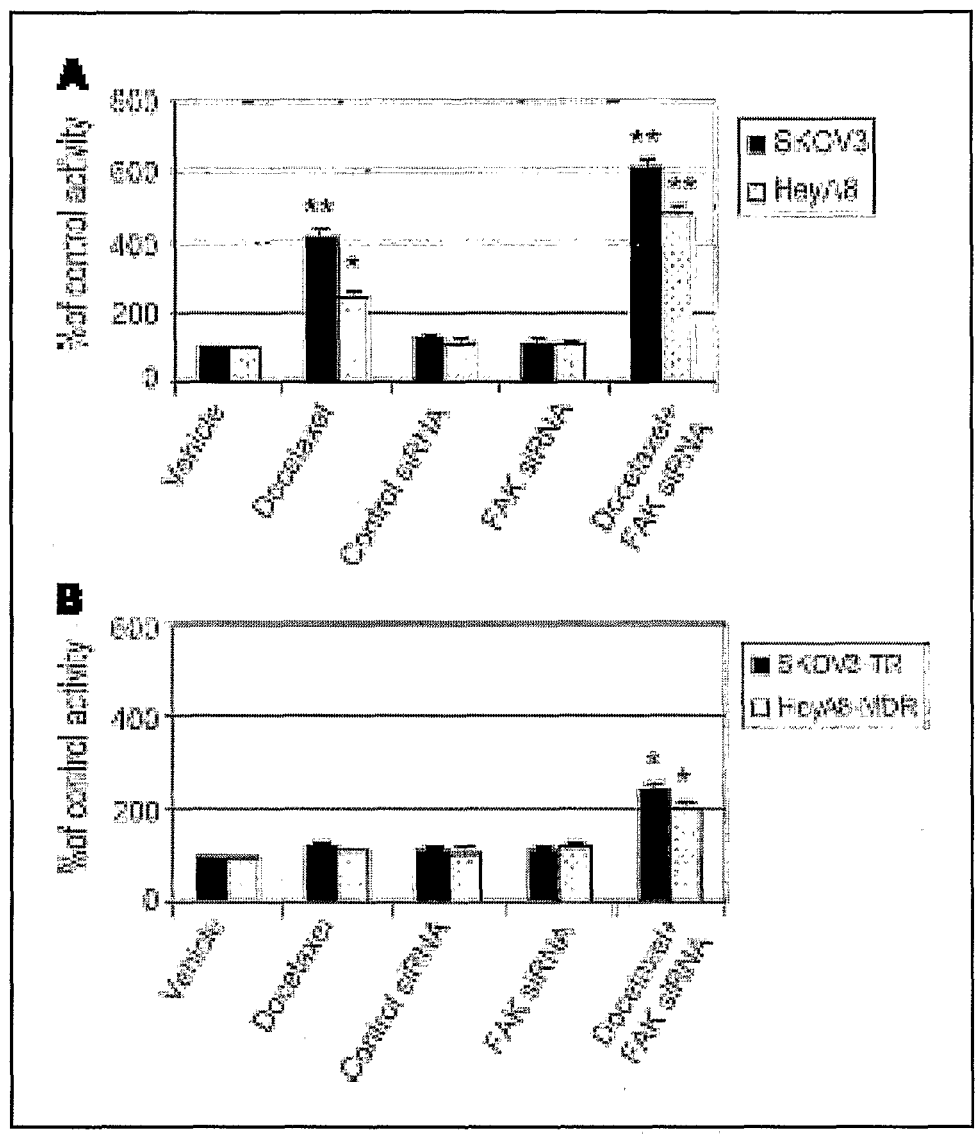
FIGS. 9A-9B. FAK gene silencing potentiates docetaxel-induced caspase-3 activity in (A) SKOV3 and HeyA8 and (B) SKOV3-TR and HeyA8-MDR cells. Columns, means of three experiments; bars, SE. *, P<0.01; **, P<0.001.

Caspase-3 activity in response to FAK silencing and docetaxel treatment was examined. Caspase-3 activity was enhanced by docetaxel after FAK down-regulation in the taxane-sensitive cell lines (FIG. 9A) but not in the resistant cell lines (FIG. 9B). Treatment with FAK siRNA or control siRNA alone did not potentiate the activity of caspase-3 in either taxane-sensitive or taxane-resistant cell lines (FIGS. 9A and 9B). Caspase-3 activity was 6.1-fold higher in the SKOV3 cells and 4.8-fold higher in the HeyA8 cells after treatment with FAK siRNA in combination with docetaxel (both Ps<0.001 compared with treatment with vehicle alone). Caspase-3 activity was also enhanced by docetaxel after FAK downregulation in the resistant cell lines (FIG. 9B). Thus, downregulation of FAK alone does not increase caspase-3 activity, but FAK inhibition enhances the docetaxel-mediated induction of caspase-3 activity.

Focal Adhesion Kinase Silencing Enhances Docetaxel-Induced Apoptosis.

Figures 10A, 10B, 10C, 10D:
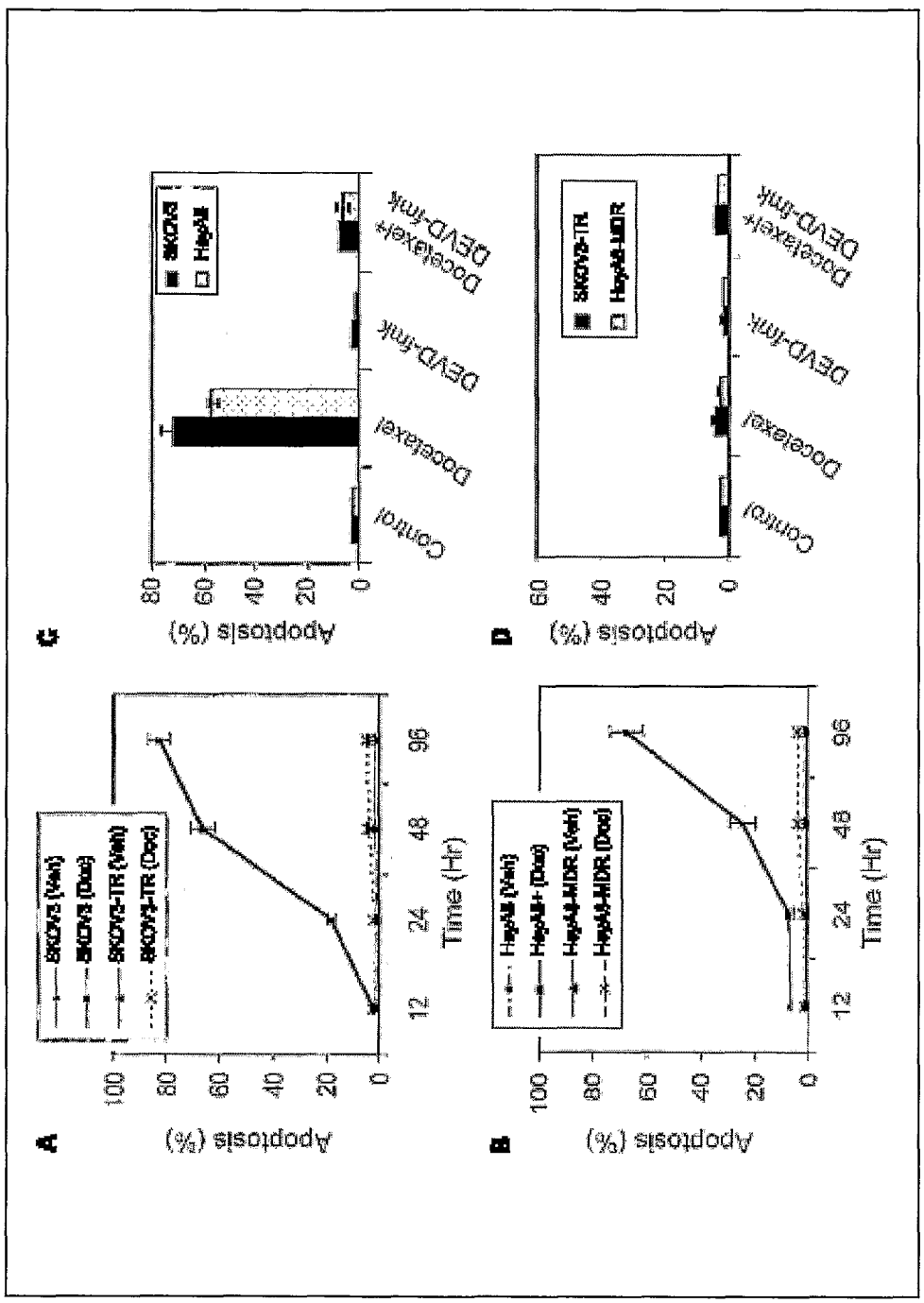
FIGS. 10A-10D. Effects of docetaxel on (A) SKOV3 and SKOV3-TR or (B) HeyA8 and HeyA8-MDRovarian cancer cells. The percentage of apoptosis was determined by terminal deoxynucleotidyl transferase-mediated nick end labeling. Cells were treated with or without $IC_{90}$ concentration of docetaxel for the taxane-sensitive cell lines. Points, means of three different experiments; bars, SE. Effect of docetaxel with or without the caspase-3 inhibitor (DEVD-fmk) on (C) SKOV3 and SKOV3-TR and (D) HeyA8 and HeyA8-MDRovarian cancer cell apoptosis. Columns, means of three independents experiments; bars, SE.

The effect of FAK suppression on docetaxel-mediated apoptosis was examined. The inventors first characterized induction of apoptosis by docetaxel alone in the ovarian cancer cells using the terminal deoxynucleotidyl transferase-mediated nick end labeling assay. Cells were treated with either IC50 or IC90 levels of docetaxel for the taxane-sensitive cell lines and harvested at time intervals ranging from 12 to 96 hours. The percentage of apoptosis in the control cells remained low over time in all cell lines (FIG. 10). After docetaxel treatment for 96 hours, the proportion of apoptotic cells increased to 84% in the SKOV3 cells (FIG. 10A) and 66% in the HeyA8 cells (FIG. 10B). To determine whether docetaxel-induced apoptosis is indeed caspase mediated, the inventors used the caspase-3 inhibitor DEVD-fmk, which significantly reduced the proportion of apoptotic cells (FIG. 10C) in response to docetaxel after 72 hours (72-7% in SKOV3 and 56-6% in HeyA8 cells). The level of apoptosis remained low in the taxane-resistant cell lines despite treatment with docetaxel and was not affected by DEVD-fmk (FIG. 10D).

Figures 11A, 11B:
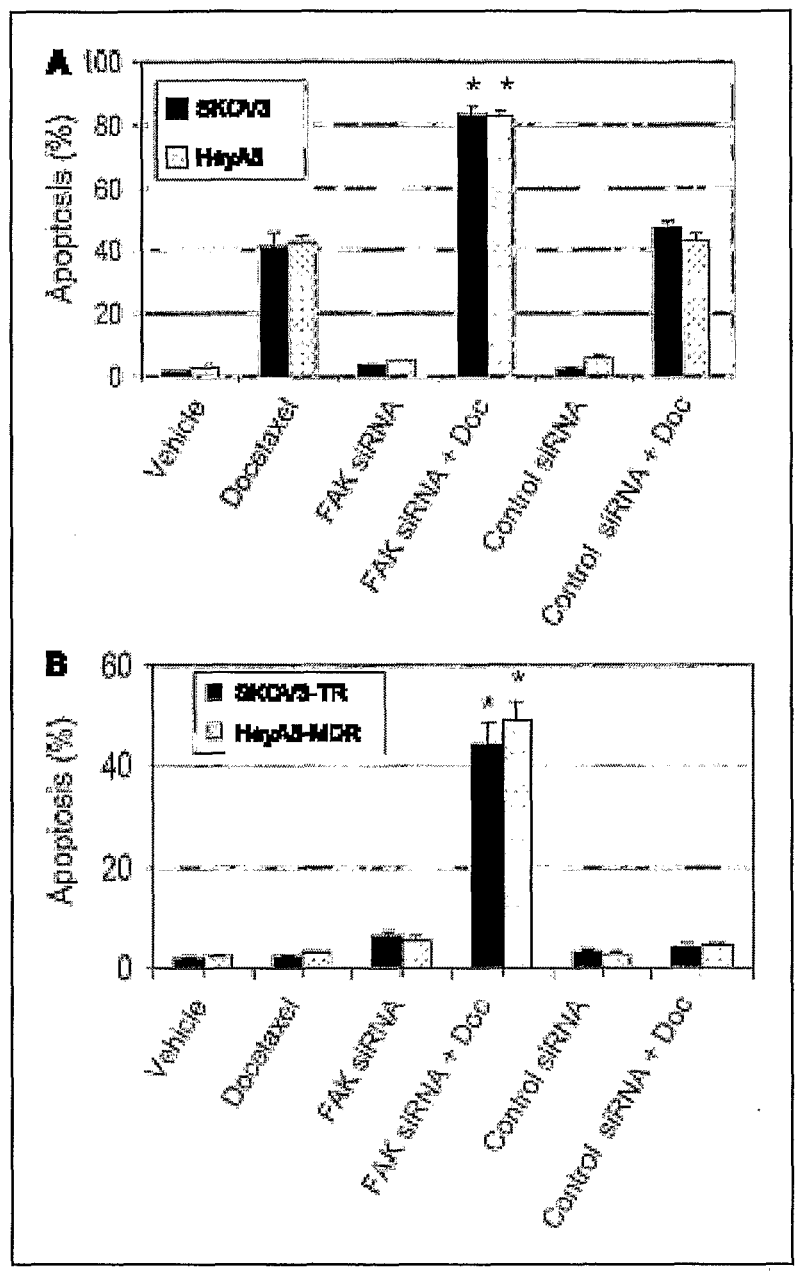
FIGS. 11A-11B. Docetaxel-mediated apoptosis with or without FAK siRNA in (A) SKOV3 and HeyA8 and (B) SKOV3-TR and HeyA8-MDR ovarian cancer cells. Columns, means of three independent experiments; bars, SE. Doc, docetaxel.

To test whether apoptosis might be affected by FAK silencing, the $IC_{20}$ levels of docetaxel was used. Ovarian cancer cells were treated with FAK siRNA for 48 hours, and then docetaxel was added. At the $IC_{20}$ levels of docetaxel, about 41% apoptosis was observed in the SKOV3 cells and 42% in the HeyA8 cells (FIG. 11). However, in combination with FAK siRNA, apoptosis increased to 83% in the SKOV3 cells and 84% in the HeyA8 cells (both Ps<0.01 when compared with docetaxel alone). Next, the effects of FAK silencing with or without docetaxel on apoptosis in the taxane-resistant cells was examined. Although neither agent alone induced much apoptosis, the combination resulted in a marked increase in apoptosis in the SKOV3-TR and HeyA8-MDR cells (FIG. 11B). Control siRNA did not enhance apoptosis in combination with docetaxel (FIGS. 11A-11B). These findings suggest that FAK silencing in combination with docetaxel has at least an additive effect on induction of apoptosis.

In Vivo Down Regulation of FAK by siRNA.

Figures 12A, 12B:
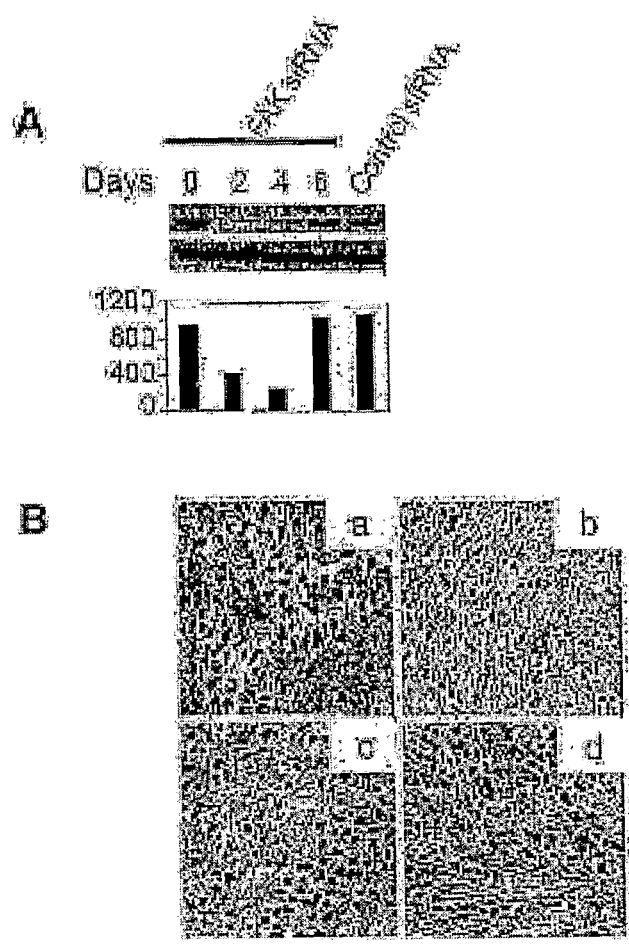
FIGS. 12A-12B. In vivo downregulation of FAK by FAK siRNA. (A) Western blot of lysates from tumor samples collected 1, 2, 4, and 6 d after a single administration of FAK siRNA or control siRNA incorporated in DOPC. Quantification of band intensity relative to p-actin is graphed below. (B) Immunohistochemical staining for FAK expression after treatment with control siRNA(a) or FAK siRNA 2(b), 4(c), and 6(d) days after a single dose. (B) original magnification ×200.

The inventors investigated the inhibition of FAK expression in combination with docetaxel and the in vivo therapeutic potential. Prior to initiating therapy studies, the ability of FAK-targeted siRNA incorporated in DOPC to down-regulate FAK in vivo was assessed. Nude mice bearing intraperitoneal HeyA8 tumors were injected with a single dose of FAK siRNA i.p., and tumors were harvested 1, 2, 4, and 6 days after injection for Western blot analysis and immunohistochemistry for assessing level of FAK expression. Western blot analysis revealed >80% reduction in FAK levels within 48 hours, which persisted for at least 4 days (FIG. 12A). FAK expression began to return to basal levels by 6 days after a single treatment. Similar results were noted with immunohistochemistry (FIG. 12B). FAK expression was not affected by control siRNA. Twice weekly administration of siRNA (150 μg/kg) was selected as an exemplary dosing schedule for subsequent therapy experiments.

In Vivo Therapy Experiments with DOPC-FAK siRNA.

Figures 6A, 6B, 6C:
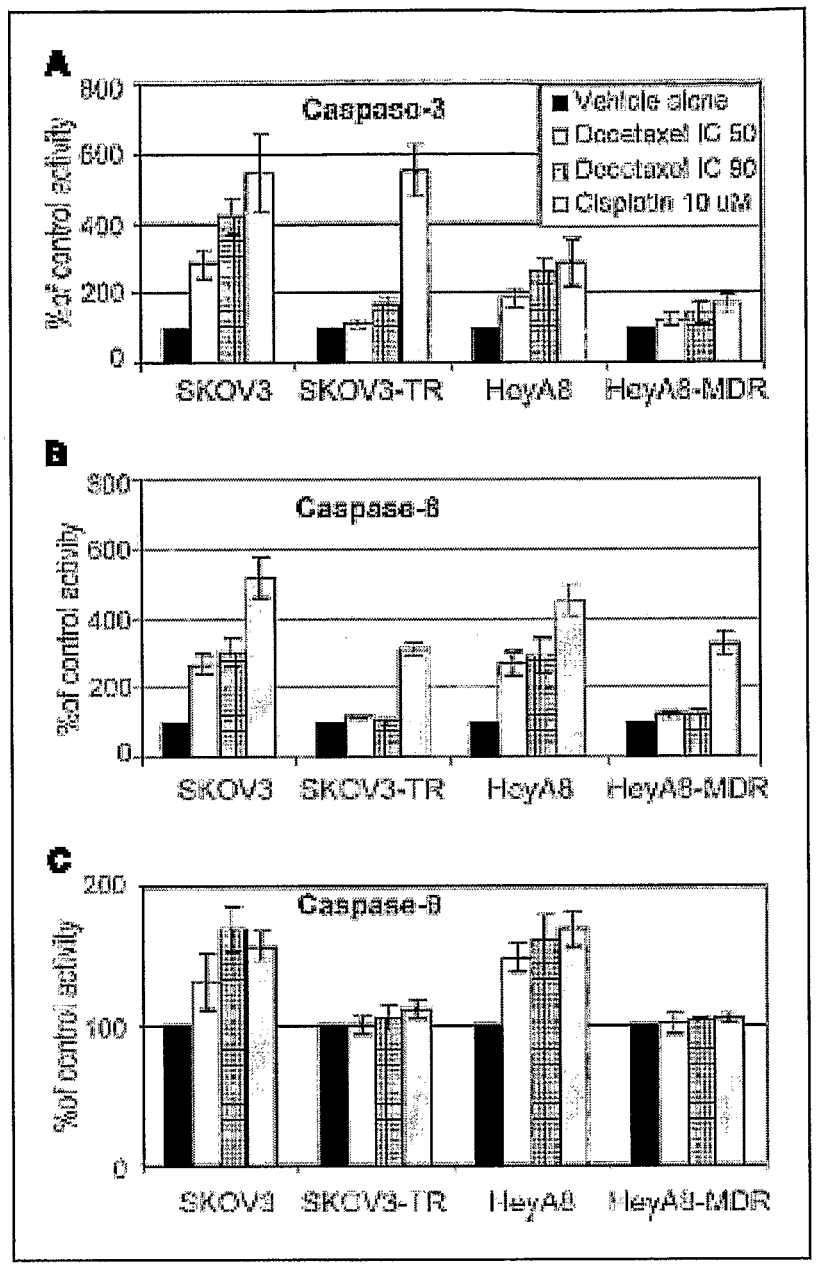
FIGS. 6A-6C. Effect of docetaxel on caspase-3 (A), caspase-8 (B), and caspase-9 (C) activity. Ovarian cancer cells were treated with docetaxel for 24 hours followed by fluorometric profiling of caspase activity using a commercially available kit. Columns, means of three independent experiments; bars, SE.
Figures 13A, 13B, 13C:
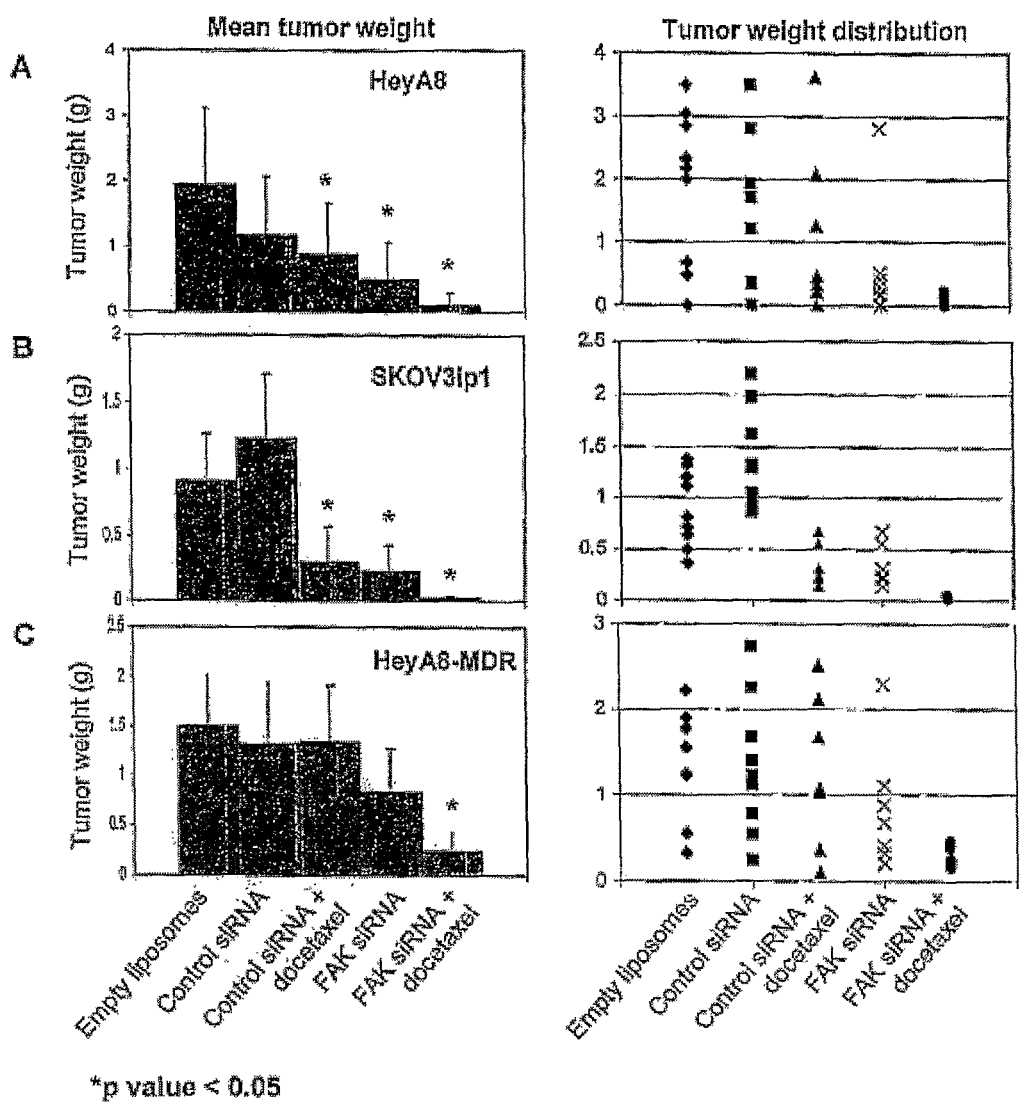
FIGS. 13A-13C. Therapeutic efficacy of FAK siRNA mediated FAK downregulation. Nude mice were injected i.p. with $2.5 \times 10^5$ HeyA8 (A) $1.0 \times 10^6$ SKOV3ip1 (B) or $2.5 \times 10^5$ HeyA8-MDR cells (C) and randomly allocated to one of the following groups, with therapy beginning one week after cell injection: 1) empty DOPC liposomes, 2) control siRNA in DOPC, 3) control siRNA in DOPC+docetaxel, 4) FAK siRNA in DOPC, and 5) FAK siRNA in DOPC+docetaxel. The animals were sacrificed when control mice became moribund (4-6 weeks after tumor cell injection) and necropsy was performed. Mean tumor weights with standard deviation (left), and individual weights (right) are shown.

The SKOV3ip1 or HeyA8 ovarian cancer cells were implanted into the peritoneal cavity of athymic nude mice for experiments designed to test the therapeutic potential of FAK-targeted inhibition of gene expression. Seven days later, therapy was started according to the following five treatment groups: 1) empty liposomes; 2) non-specific siRNA-DOPC; 3) docetaxel plus non-specific siRNA-DOPC; 4) FAK targeted siRNA-DOPC; and 5) docetaxel plus FAK-targeted siRNA-DOPC. The animals were sacrificed after 4 weeks of therapy and a necropsy was performed. The data for these therapies' effects on SKOV3ip1 and HeyA8 are summarized in FIGS. 6A and 6B, respectively. Control siRNA therapy alone was not effective against SKOV3ip1 tumors compared with empty liposomes, however, about 39% reduction was noted in the HeyA8 tumors (FIGS. 6A and 6B). Treatment with FAK siRNA alone or docetaxel plus control siRNA were effective in inhibiting tumor growth (54 to 74%) in both cell lines compared with control (FIG. 13). However, treatment with FAK siRNA in combination with docetaxel resulted in even greater reduction in tumor weight (94 to 98) % (overall ANOVA p value <0.001 for both cell lines). Furthermore, the combination therapy was statistically superior to docetaxel plus control siRNA in each of the two trials (p=0.04 for HeyA8 and 0.02 for SKOV3ip1).

Chemotherapy-resistance is a common clinical problem in the management of ovarian carcinoma. Despite high response rates with initial therapy, most patients develop recurrent tumors that are resistant to taxane and platinum chemotherapy (McGuire et al., 1996). The inventors demonstrate that FAK downregulation can sensitize even chemotherapy resistant cell lines to docetaxel. Consequently FAK downregulation and its effects on sensitization of resistant tumors to chemotherapy, using the HeyA8-MDR cell line (FIG. 13C) was assessed. Therapy was started 7 days after injection of tumor cells into nude mice according to the 5 groups outlined above. With this model, FAK siRNA alone resulted in about 44% reduction in tumor growth (FIG. 13C) compared to control, but this difference was not statistically significant (p=0.17). However, the combination of FAK siRNA and docetaxel was superior than docetaxel/control siRNA (p<0.006) and FAK siRNA alone (p<0.05).

Data from other measured variables of these studies are shown in Table 1. The incidence of tumor formation was not significantly reduced in either control siRNA or control siRNA plus docetaxel. FAK siRNA treatment was associated with 70% tumor incidence in both of the cell lines individually, which was reduced to 50 and 60% by the combination in the SKOV3ip1 and HeyA8 cell lines, respectively. Therapy was not continued long enough to allow development of ascites, which typically develops with the SKOV3ip1 cell line about 5 to 6 weeks after injection. No obvious toxicities were observed in the animals during the course of treatment, as determined by behavioral changes such as eating habits and mobility. Furthermore, mouse weights were not significantly different among the five groups of animals, suggesting that eating and drinking habits were not affected.

Figures 14A, 14B, 14C, 14D, 14E, 14F, 14G:
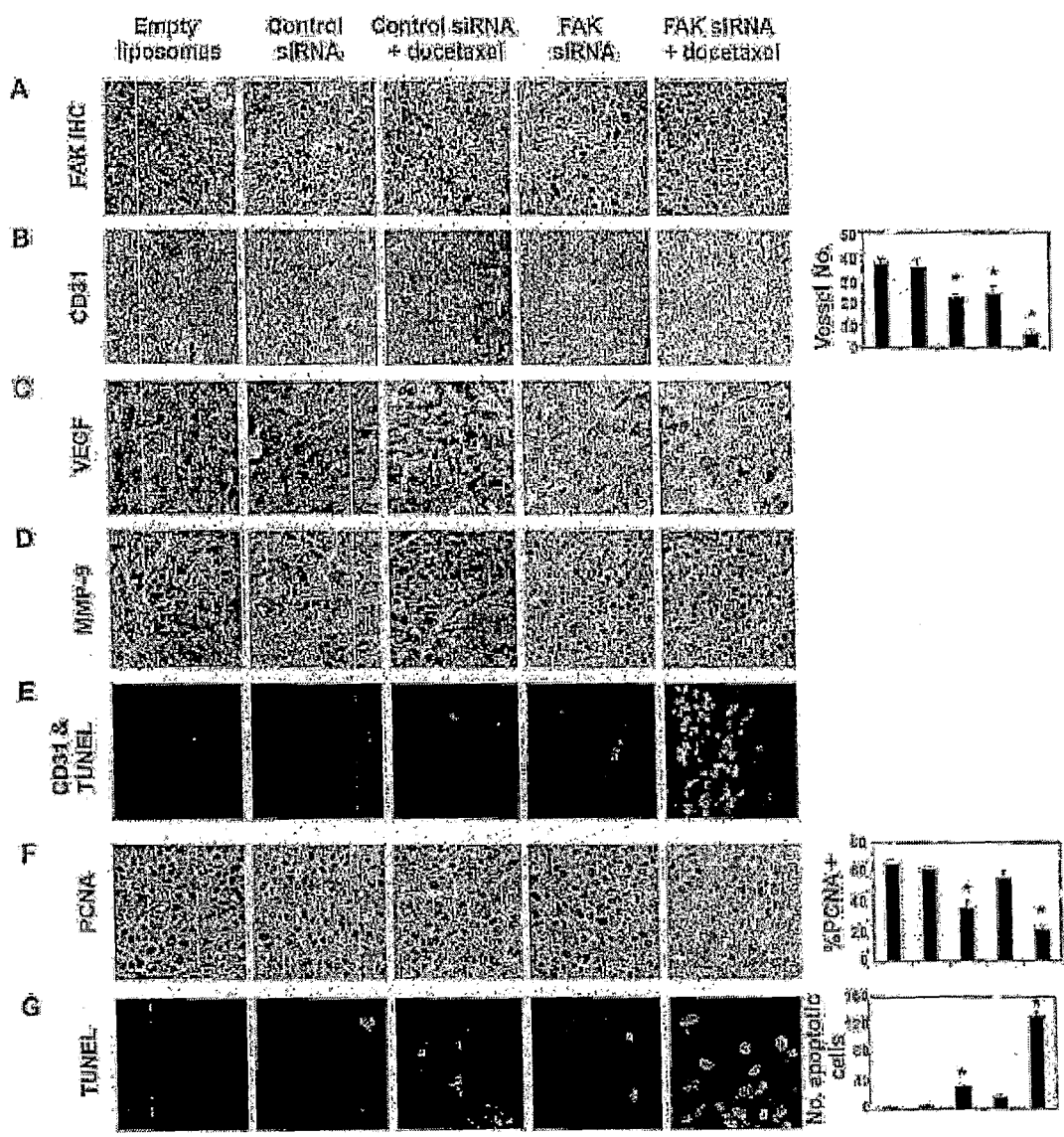
FIGS. 14A-14G. (A), Immunohistochemistry (IHC) of FAK expression after long-term therapy in the HeyA8 orthotopic model. (B) Microvessel density (MVD) was determined after immunohistochemical peroxidase staining for CD31. The number of vessels per 100× field were counted. Representative slides from each group are shown, and the average number of vessels per field are shown in the graph. Five fields per slide, and at least 3 slides per group were examined. VEGF (C) and MMP-9 (D) immunohistochemical peroxidase staining was performed on tumor sections obtained from each of the five therapy groups. (E) Representative images of immunofluorescence staining with CD31 positive cells and cells undergoing apoptosis are shown. Endothelial cells undergoing apoptosis can be identified by yellow fluoresence. (F) Tumor sections from each group were stained for PCNA. The number of cancer cell nuclei that were strongly PCNA positive were counted and divided by the total number of cells. Representative sections from each group are shown (final magnification ×100), with mean±SD percentage of PCNA-positive cells graphed. Four fields per slide, and at least 3 slides per group (all from different animals) were counted. (G) Immunofluorescence staining with TUNEL using green fluorphore for apoptosis and Hoescht using a blue fluorophore for nuclei was performed and representative slides are shown from each group. The number of apoptotic cells were counted and the mean number±SD of TUNEL-positive cells graphed. Four fields per slide, and at least 3 slides per group (all from different animals) were counted. The bars in the graph correspond to the labeled columns shown in the picture.

At the conclusion of the therapy studies, FAK expression in HeyA8 cells was assessed and remained suppressed. FAK levels were not suppressed in either the control siRNA, empty liposome, or control siRNA plus docetaxel groups (FIG. 14A). However, in the FAK siRNA and combined FAK siRNA with docetaxel groups, there was sustained suppression of FAK expression (FIG. 14A).

Effect of FAK Targeting on Angiogenesis, Cell Proliferation, and Apoptosis.

While FAK suppression has been shown to have direct anti-tumor effects emerging evidence indicates that there may also be effects on the tumor microenvironment. To determine potential mechanisms underlying the efficacy of anti-FAK based therapy, its effects on several biological endpoints were examined, including angiogenesis (MVD), proliferation (PCNA), and apoptosis (TUNEL). Due to growing evidence related to FAK and tumor angiogenesis (Kornberg et al., 2004; Mitra et al., 2005). The inventors evaluated vessel density (FIG. 14B) in the tumors harvested from the studies described above. Compared with empty liposomes, the mean MVD was reduced in tumors treated with FAK siRNA alone or control siRNA with docetaxel (p values 0.008 and 0.009 respectively). The most significant reduction in MVD occurred in the combination therapy group (6±2, p<0.001. Based on recent studies suggesting suppression of VEGF and MMPs (Mitra et al., 2005a; Mitra et al., 2005b, Shibata et al., 1998; Sein et al., 2000), the inventors examined tumors harvested from all groups for these proteins. Indeed, both VEGF and MMP-9 expression (FIGS. 7C-7D) was substantially reduced in tumors from animals treated with FAK siRNA-DOPC alone or in combination with docetaxel, suggesting an anti-vascular mechanism. To further characterize the anti-vascular mechanism, the inventors performed dual localization (CD31 and TUNEL) immunofluorescence studies after treatment in all groups. Tumors treated with control siRNA had prominent vasculature with no apotosis seen in endothelial cells (FIG. 14E). However, endothelial cell apoptosis was significantly increased in both FAK siRNA and FAK siRNA plus docetaxel treated groups. To determine if FAK siRNA mediated in vivo effects on endothelial cells were direct, the inventors treated murine endothelial cells isolated from the ovary of ImmortoMice (H-2k(b)-ts A58) (Langley et al., 2003) with FAK siRNA. Murine FAK levels were not altered by the FAK siRNA used for the in vivo studies (data not shown).

Next, the effects of FAK-targeted therapy on tumor cell proliferation were examined by using PCNA staining. Minimal reduction of PCNA expression was observed by either control siRNA plus docetaxel or FAK siRNA compared to either empty liposome or control siRNA treatment groups. PCNA expression was significantly reduced (21±1.6%) in tumors from mice receiving FAK siRNA with docetaxel (FIG. 14F). Finally, tumor cell apoptosis was evaluated by using the TUNEL method. Cells undergoing apoptosis exhibited green fluorescence. Minimal tumor cell apoptosis was apparent in either the empty liposome, single agent or control siRNA with docetaxel treatment groups. FAK siRNA with docetaxel resulted in a significant increase in apoptosis (FIG. 14G).

TABLE 1

| Cell Line | Group | Incidence (%) | No. Nodules | P values for number of nodules |
|---|---|---|---|---|
| SKOV3ip1 | Liposomes | 100 | 15 | NS |
|  | Control siRNA | 100 | 15 | NS |
|  | Control siRNA + Docetaxel | 80 | 4 |  |
|  | FAK siRNA | 70 | 3.7 | <0.001 |
|  | FAK siRNA + Docetaxel | 50 | 1.3 | <0.0001 |
| HeyA8 | Liposomes | 100 | 4.4 | NS |
|  | Control siRNA | 100 | 4.0 | NS |
|  | Control siRNA + Docetaxel | 90 | 2.5 | 0.009 |
|  | FAK siRNA | 70 | 1.7 | 0.004 |
|  | FAK siRNA + Docetaxel | 60 | 0.9 | <0.001 |
| HeyA8-MDR | Liposomes | 90 | 4.3 |  |
|  | Control siRNA | 90 | 4.4 | NS |
|  | Control siRNA + Docetaxel | 80 | 3.8 | NS |
|  | FAK siRNA | 70 | 2.1 | 0.002 |
|  | FAK siRNA + Docetaxel | 70 | 1.3 | <0.001 |

Example 3

Beta Adrenergic Receptors and Stress Related Exacerbation of Cancer Cell Growth

The inventors have recently demonstrated that chronic stress accelerates tumor growth by promoting angiogenesis using an ovarian tumor model. The inventor screened nineteen ovarian cancer cell lines by RT-PCR for the presence or absence of the β1 and β2 adrenergic receptors (βAR). Female nude mice were obtained and allowed to habituate for 1 week prior to use and then divided into the following groups (n=10): control (food and water deprived) and stress (physical restraint, food, and water deprived) for 2 hours daily. The βAR null (A2780 and RMG2) and positive (HeyA8 and SKOV3ip1) ovarian cancer cells were injected i.p. 10 days after stress initiation. Additionally, blocking experiments using liposomal (DOPC) siRNA to β1, β2, or both receptors were performed. All mice were necropsied 21 days after injection.

In the β-positive HeyA8 injected mice, the tumor weight increased by 2-fold (p=0.02), and the tumor nodules increased by 3.5-fold in stressed mice. Fifty percent of stressed βAR positive mice had more invasive disease involving the parenchyma of organs. Control A2780 mice had average tumor weight of 0.38 g+0.15 and 3.5±0.9 tumor nodules versus 0.38 g±0.09 and 5±1.6 in the stressed mice. Similar results were seen in the RMG2 injected mice, and none of the mice injected with βAR null cells exhibited an invasive pattern of metastasis. The HeyA8 injected mice treated with control or β1 siRNA demonstrated 2-3 fold increases in tumor weight and 2.5 to 3-fold increases in the number of nodules with chronic stress. Remarkably, the β2 siRNA completely blocked the stress induced increase in tumor weight, number of nodules, and the invasive pattern of metastasis. Mice treated with combined β1 and β2 siRNA had results similar to the β2 siRNA only group. These studies indicate that the effects of chronic stress are primarily mediated through the β2AR on ovarian cancer cells. Therefore, targeting the βAR may have therapeutic implications for the management of ovarian cancer.

I. Methods

Ovarian Cancer Cell Line and Culture Conditions.

HeyA8, SKOV3ip1, A2780, and RMG-II human ovarian cancer cell lines (Thaker et al., 2005) were grown as monolayer cultures in complete minimal essential medium (CMEM) (Gibco, Grand Island, N.Y.) supplemented with 10% fetal bovine serum (FBS), vitamins, sodium pyruvate, L-glutamine, nonessential amino acids (Life Technologies, Inc., Grand Island, N.Y.), and penicillin-streptomycin (Flow Laboratories, Rockville, Md.). The RMG-II cell line was obtained as a kind gift from Drs. Naoto Ueno and Hiroaki Itamochi (M.D. Anderson Cancer Center, Houston, Tex.). The tumor cells were free of *Mycoplasma* and known pathogenic murine viruses (assayed by Science Applications International Corporation, Frederick, Md.).

Animals.

Ten-12 week old female athymic nude mice (NCr-nu,) came from the Animal Production Area of the National Cancer Institute-Frederick Cancer Research and Development Center (Frederick, Md.). All experiments were approved by the University of Texas Institutional Animal Care and Use Committee.

Orthotopic Implantation of Tumor Cells, Stress Procedures, and Necropsy Procedures.

Mice habituated to vivarium conditions for 1 week before the initiation of stress procedures. A restraint-stress procedure was used based on previous studies (Sheridan et al., 1991), substituting a novel Mouse Restraint System (FIG. 15A) for conical centrifuge tubes. In this system, up to 10 mice are placed in individual slots, and each slot can be adjusted to restrain the animal for a desired length of time. In the present study, restraint stress began between 8 a.m. and 10 a.m., and lasted for 2-6 hours for up to 21 days. The ovarian cancer cell lines were harvested from subconfluent cultures by a brief exposure to 0.25% trypsin and 0.02% EDTA, resuspended in Hank's balanced salt solution (HBSS), and tested for >95% viability by trypan blue dye exclusion. The HeyA8 cells were injected i.p. into mice at a concentration of $2.5 \times 10^5$ cells while the other cell lines were injected at $1.0 \times 10^6$ cells per 0.2 ml HBSS, ten days after starting stress in all groups. Animals were necropsied 21 days after tumor injection, and tumors in the peritoneal cavity were excised, weighed, and documented for location. Immunohistochemistry and H&E staining procedures were carried out on formalin-fixed paraffin-embedded tumors.

Chronic Beta-Blockade and Stress.

Mice were allowed to attain a weight of at least 21 grams prior to insertion of the Alzet osmotic minipump (DURECT Co., Cupertino Calif.). Pumps were inserted on the nape of the neck 7 days prior to initiation of restraint stress for 2 hours daily. Mice were anesthetized with inhaled methoxyflurane (Medical Developments Australia Pty. Ltd, Melbourne, Australia), and implanted with Alzet pumps containing PBS or S-propranolol hydrochloride (Sigma Co., St. Louis, Mo.) diluted in PBS at a dose of 2 mg/kg/day, which allows for chronic continuous receptor blockade, for 28 days (Aarons and Molinoff, 1982; Exton et al., 2002).

Reagents.

All reagents were purchased from Sigma or Tocris Bioscience (Ellisville, Mo.).

Small Interfering RNA Constructs and Liposomal Preparation.

siRNAs targeted against β1AR (target sequence 5'-CCGATAGCAGGTGAACTCGAA-3' (SEQ ID NO:11)) or β2AR (target sequence: 5'-CAGAGTGGATATCACGTG-GAA-3' (SEQ ID NO:12)) were purchased from Qiagen (Valencia, Calif.), and incorporated into a neutral liposome 1,2-dioleoyl-sn-glycero-3-phosphatidlycholine (DOPC), as previously described (Laden et al., 2005).

Inhibition of VEGF-R Signaling.

VEGF-R signaling was blocked using 50 mg/kg of the oral tyrosine kinase inhibitor of VEGF-R249, PTK787/ZK232394 (1-[4-Chloroanilino]-4-[pyridylmethyl]phthalazine dihydrochloride) daily.

Real-Time RT-PCR Analysis.

Total RNA was extracted (Trizol reagent; Invitrogen Co, Carlsbad, Calif.) and reverse transcribed using an oligo(dT) primer and M-MLV reverse transcriptase (Life Technologies, Inc., Rockville, Md.) in a final reaction volume of 20 μl (60 min at 42° C.). PCR amplifications are performed using the ABI Prism 7700 Sequence Detection System with TaqMan One-Step RT-PCR Master Mix Reagent kit (PE Applied Biosystems, Foster City, Calif.). Quantitative values are obtained from the Ct value, at which the increase in fluorescent signal associated with exponential growth of PCR products starts to be detected by the laser detector of the Sequence Detection System, using the analysis software according to the manufacturer's instructions (each sample is normalized on the basis of its I8S content). The VEGF primers were obtained from Applied Biosystems (Item number HS00173626-ml). βAR expression was examined with semi-quantitative RT-PCR using the following primers: βAR (forward, 5'-TCG-GAATCCAAGGTGTAGGG-3' (SEQ ID NO:13), reverse, 5'-TGGCTTTTCTCTTTGCCTCG-3') (SEQ ID NO:14); β2AR (forward, 5'-CATGTCTCTCATCGTCCTGGCCA-3' (SEQ ID NO:15), reverse, 5'-CACGATGGAAGAG-GCAATGGCA-3') (SEQ ID NO:16).

Promoter Analysis.

The VEGF promoter was a kind gift from Dr. Lee Ellis (M.D. Anderson Cancer Center, Houston, Tex.). Ovarian cancer cells were transiently transfected (Invitrogen Lipofectamine 2000) with the VEGF promoter-reporter constructs and the luciferase activity was determined in triplicate as previously described (Reinmuth et al., 2001).

Assessment of Norepinephrine and Corticosterone In Vivo.

Organ norepinephrine, epinephrine, and corticosterone levels were quantified using HPLC (Agilent 1100 binary HPLC, Wilmington, Del.) tandem mass spectrometry (Waters QuattroUltima, Waters, Milford, Mass.). Frozen pulverized ovary, spleen, and omentum tissues were weighed, suspended in HPLC grade methanol (Fisher Scientific, Pittsburgh, Pa.), and homogenized by ultrasonic disruption using a Misonix 3000 tissue homogenizer (Misonix, Farmingdale, N.Y.). Samples were centrifuged at 15000×g for 5 min at 5° C. to pellet cellular debris, and 0.1 ml supernatant was then mixed 1:1 with 20 mM ammonium acetate (pH 3.5) for analysis.

Chromatographic resolution of epinephrine, norepinephrine, and corticosterone was achieved using a Phenomenex Synergy 4 μm Hydro-RP (150×2 min) analytical column (Phenomenex, Torrance, Calif.) with a linear mobile phase gradient separation method. Mass spectrometry analysis was performed using electrospray positive ionization in multiple reaction-monitoring mode. Specific mass transitions detecting epinephrine, norepinephrine, and corticosterone were 184>166, 152>134.9, and 347>328.9 respectively.

Immunohistochemistry.

Paraffin sections were stained for CD31 (1:800 dilution, Pharmingen, San Jose, Calif.), MMP-2 (1:500 dilution, Chemicon, Temecula, Calif.), MMP-9 (1:200 dilution, Calbiochem, San Diego, Calif.), VEGF (1:500 dilution, Santa Cruz Biotechnology, Santa Cruz, Calif.) and bFGF (1:1,000 dilution, Sigma, St. Louis, Mo.) at 4° C. Samples were stained with a biotinylated goat anti-rabbit antibody for 30 min (prediluted), followed by strepavidin horseradish peroxidase for 30 min (1:300 dilution), and visualized in 3,3'-diaminobenzidine (DAB) for 5-10 min. Control samples were exposed to secondary antibody alone and showed no nonspecific staining.

In Situ Hybridization (ISH).

A specific antisense oligonucleotide DNA probe was designed complementary to the mRNA transcript of the angiogenic gene VEGF, 5'-TGGTGATGTTGGACTCCT-CAGTGGGC-3' (SEQ ID NO:17) (1:200). The specificity of the oligonucleotide sequence was initially determined by a GenEMBL database search using the FastA algorithm (Radinsky, 1993), which showed 100% homology with the target gene and minimal homology with nonspecific mammalian gene sequences. A d(T)20 oligonucleotide was used to verify the integrity of mRNA in each sample. In situ hybridization was performed as described previously with minor modifications (Radinsky, 1993). The Microprobe manual staining system (Fisher Scientific, Pittsburgh, Pa.) was used to stain tissue sections. A positive reaction in this assay stained red. The samples were not counterstained; therefore, the absorbance was attributable solely to the product of the ISH reaction.

Microscopy and Image Analysis.

Sections were examined with a Nikon Microphot-FX microscope (Nikon Inc., Garden City, N.Y.) equipped with a three-chip charge-coupled device color video camera, (Model DXC990, Sony Corp., Tokyo, Japan). Photomontages were prepared using Micrografx Picture Publisher (Corel Inc., Dallas, Tex.) and Adobe Photoshop software (Adobe Systems Inc., San Jose, Calif.). The images were analyzed using the Optimas image analysis software (Bothell, Wash.).

Quantification of Microvessel Density (MVD).

To quantify MVD, 10 random 0.159 mm$^2$ fields at 100× magnification were examined for each tumor, and the microvessels within those fields were counted. A single microvessel was defined as a discrete cluster of cells stained CD31(+), and the presence of a lumen was required for scoring as a microvessel.

Statistical Analysis.

Comparisons of mean tumor weight and number of tumor nodules were analyzed by analysis of variance (ANOVA) and t-test using SPSS (SPSS Inc., Chicago, Ill.). For comparisons of mean MVD and VEGF quantification, Student t-test was utilized. $p<0.05$ was considered statistically significant.

II. Results

Characterization of In Vivo Chronic Stress Model.

No previous studies have analyzed the role of chronic stress in an ovarian carcinoma model, therefore, the inventors developed a novel physical restraint model in which animals were immobilized in individual lucite chambers for 2-6 hours daily (FIG. 15A). Due to paucity of data regarding catecholamine and corticosterone levels in nude mice, changes in these hormones were characterized in the stress model. After one week of habituation to the vivarium setting, animals were stressed for 1, 3, 7, and 14 days of daily restraint stress, after which tissue catecholamine and corticosterone levels were assayed by HPLC in various tissues in the peritoneal cavity (the site of ovarian cancer metastasis) including ovaries, spleen, and omentum (plasma catecholamine levels were highly unstable, but tissue levels are known, to be more reliable) (Cao et al., 2002; Paredes et al., 1998). Following stress, norepinephrine levels increased by 255-358% in these organs (FIG. 15B), and corticosterone levels increased by 488-789% (FIG. 15C). Similar increases were seen in animals stressed for six hours (data not shown), but not in the control mice. Thus, restraint induced HPA and SNS activity characteristic of chronic stress.

Effect of Stress on Ovarian Tumor Growth In Vivo.

Figures 16A, 16B, 16C, 16D, 16E:
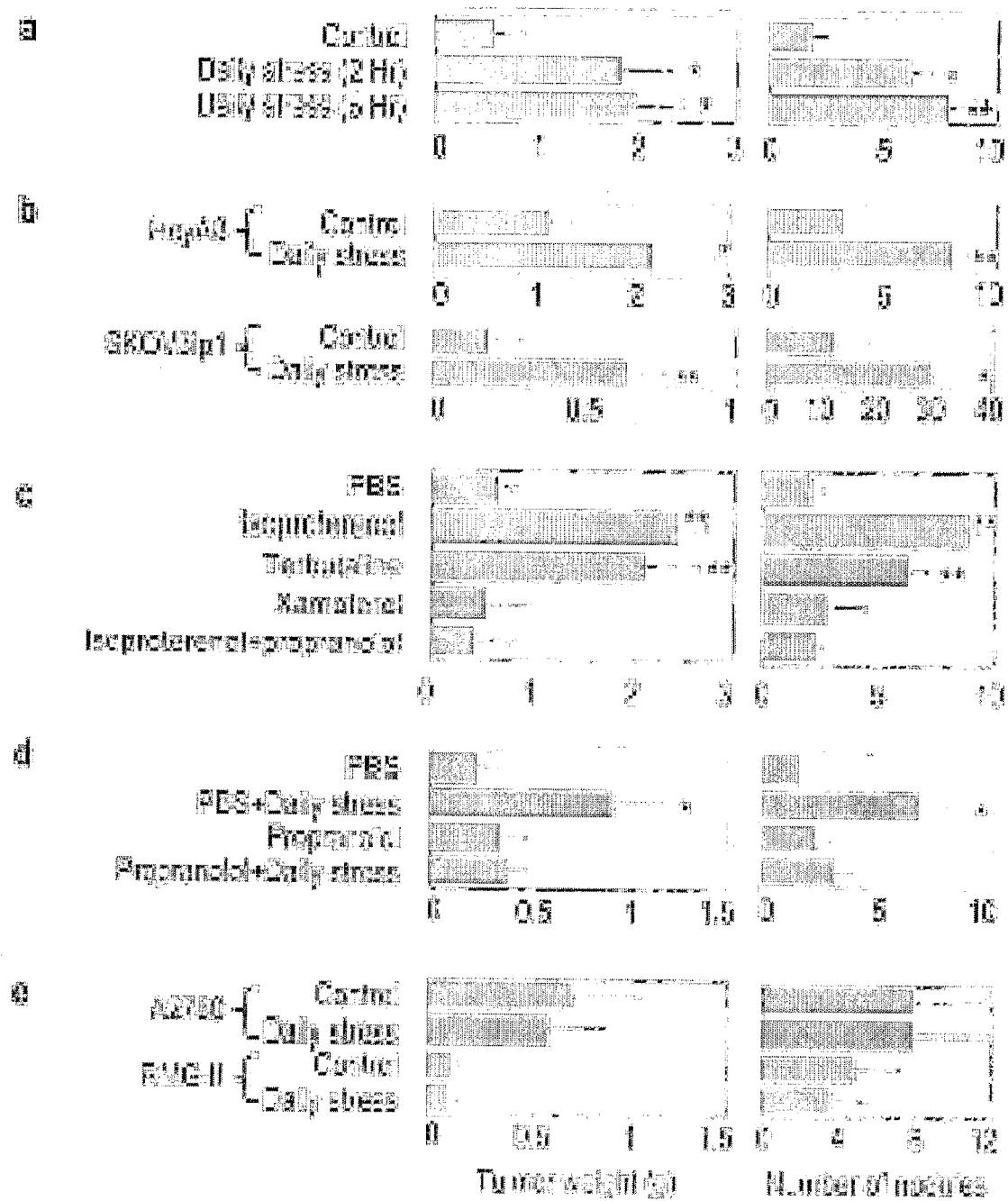
FIGS. 16A-16E. Tumor weights (left) and nodules (right) are increased in chronically stressed mice compared to controls. (A) Quantification of tumor weights and tumor nodules in control, 2-hour daily stressed, and 6-hour daily stressed mice injected with HeyA8 ovarian cancer cells. The mean tumor weights and nodules were significantly elevated between the control and stressed groups. There was no statistical difference between the 2-hour and 6-hour stress groups. (B) Confirmation of the results in mice injected with two different β-adrenergic receptor (βAR) positive ovarian cancer cell lines (HeyA8 and SKOV3ip1). (C) The effects of immobilization are mimicked by a chemical stressor isoproterenol (non-specific beta-agonist), and terbutaline (β2-agonist), but not by xamoterol (β1-agonist). Mice treated with both isoproterenol plus propranolol (β-blocker) have tumor burden similar to non-stressed mice. (D) Propranolol counteracts the effects of chronic stress, confirming the importance of the βAR. (E) Mice injected with PAR null ovarian cancer cell lines (A2780 and RMG-II) did not have accelerated tumor growth despite being chronically stressed. Results represent the mean±s.e.m.; n=10 mice per group. *p≤0.01; **p≤0.001

Subsequent experiments examined the effects of stress on tumor weight, number of tumor nodules, and pattern of metastasis in mice inoculated with HeyA8 ovarian cancer cells seven days after the initiation of restraint stress. All mice were food- and water-deprived for the duration of time in which stressed animals were restrained; therefore, the only experimental variable was the presence versus absence of restraint. In the first experiment, mice were randomized to receive 0, 2, or 6 hours of restraint stress daily for 21 days total (FIG. 16A). The number of tumor nodules increased by 2.5-fold in the 2 hour stress group (p=0.005) and 3.6-fold in the 6 hour stress group (p<0.001). The mean tumor weight was also significantly higher in both stressed groups (2.5-fold in the 2 hour group p=0.01; 2.8-fold in the 6 hour group, p=0.005). Disease was confined to the peritoneal cavity in all control mice, but spread to the parenchyma of the liver or spleen in 50% of stressed mice (p=0.01). The number and weight of tumor nodules did not differ for animals stressed 2 versus 6 hours per day. Two hours of restraint was, therefore, routinely employed in subsequent experiments.

To evaluate the generality of these results, a second experiment was performed with both the HeyA8 and SKOV3ip1 ovarian cancer cell lines using the 2-hour daily stress model (FIG. 16B). Stressed animals injected with HeyA8 cells had an average 7.9±0.5 (range 6-11) tumor nodules after 21 days, compared to 3.1±0.3 (range 1-4) in the control group (p<0.001 by t-test). The mean tumor weight was also significantly increased by stress (1.12±0.15 g for the control group versus 2.17±0.24 g for the 2 hour stress group, p=0.002). Parallel results emerged for stressed animals injected with SKOV3ip1 ovarian cancer cells (tumor nodules: control average 11.6±4.1 (range 4-39) versus stress average 28.7±2.0 (range 20-38), p=0.002; tumor weight: control average 0.19±0.04 g versus stress average 0.63±0.09 g, p=0.001). Thirty percent of the stressed animals had parenchymal liver metastases compared to none in the control group (p=0.06). To assess changes in sympatho-adrenal-medullary activity, the size of both adrenal glands were measured (Paredes et al., 1998). Among animals inoculated with HeyA8 cells, the mean left adrenal gland diameter was 1.85±0.25 mm for the control group versus 2.88±0.56 mm for the stressed group (p=0.003). Similar changes were noted in the right adrenal gland (data not shown).

Based on previous in vitro data showing that βARs are present on ovarian cancer cells (Lutgendorf et al., 2003), a series of experiments were performed to determine whether stress-induced acceleration of tumor growth was mediated via βAR signaling. Starting 4 days after tumor cell injection, mice bearing HeyA8 ovarian cancer cells (n=10 per group) were treated daily with either 1) PBS; 2) isoproterenol (non-specific β-agonist) 10 mg/kg; 3) terbutaline (β2-agonist) 5 mg/kg; 4) xamoterol (β1-agonist) 1 mg/kg; or 5) isoproterenol plus 2 mg/kg of the non-specific β-antagonist propranolol. Compared to the control group, treatment with isoproterenol increased the mean number of tumor nodules by 341% (p<0.001) and the average tumor weight by 266% (p=0.001) (FIG. 16C), which is similar to the changes seen in the immobilization model. Furthermore, a similar increase in tumor burden was noted with the β2-agonist terbutaline, but not the β1-agonist xamoterol. Propranolol blocked the isoproterenol-induced increase in tumor growth (FIG. 16C).

To verify that β-adrenergic signaling also mediated the effects of non-pharmacologic behavioral stress on tumor growth, Alzet miniosmotic pumps were surgically implanted to provide continuous β-blockade with propranolol at 2 mg/kg/day. Mice were injected with HeyA8 cells and randomized to the following groups (n=10 per group): placebo Alzet pump with no stress, placebo Alzet pump with daily 2 hour stress, propranolol Alzet pump with no stress, and propranolol Alzet pump with daily 2 hour stress (FIG. 16D). Among mice treated with placebo, stress significantly increased both mean tumor weight and the number of tumor nodules (both p<0.01). However, stress did not significantly increase tumor weight or the number of tumor nodules in mice treated with propranolol (FIG. 16D). Among stressed animals, invasive disease such as parenchymal metastasis to the liver, spleen, pancreas, and diaphragm was noted in 50% of the placebo-treated group, compared to 0% in the propranolol-treated group.

To verify the relevance of βARs for stress-induced tumor growth, 17 additional epithelial ovarian cancer cell lines were screened for presence of βAR1 and βAR2. Two cell lines (A2780 and RMG-II) were negative for both receptors by RT-PCR and Western blot (data not shown). Absence of functional βARs was confirmed by the fact that neither of the βAR negative cell lines showed an increase in intracellular cAMP levels after stimulation with norepinephrine or isoproterenol (data not shown). To determine whether stress-mediated enhancement of tumor growth was dependent on βARs, mice were injected i.p. with A2780 or RMG-II cells and subjected to the 2 hour restraint stress paradigm. In contrast to ovarian cancer cells that bore βARs, stress did not significantly affect tumor weight, number of nodules, or the pattern of spread in PAR-negative A2780 or RMG-II injected mice (FIG. 16E).

Figure 17A:
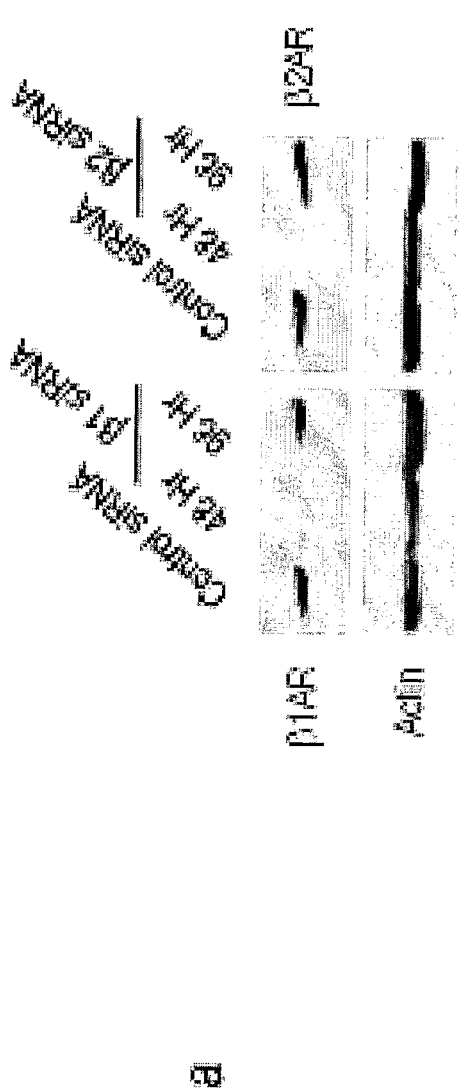
FIGS. 17A-17B. Beta2-adrenergic receptor (β2AR) plays a critical role in the acceleration of tumor growth and metastasis in chronic stress. (A) Western blot lysate from orthotopic HeyA8 tumors collected 48 hours and 96 hours after a single administration of control siRNA, β1 siRNA, or β2 siRNA complexed with DOPC shows downregulation of the respectively targeted PAR. (B) HeyA8 injected mice with chronic stress treated with control or β1 siRNA demonstrated 2-3 fold increases in tumor weight and 2.5 to 3 fold increases in tumor nodules. More importantly, β2 siRNA completely blocked the effects of stress on tumor growth and metastasis. Results represent the mean±s.e.m.; n=10 mice per group. *p≤0.01; **p≤0.001
Figure 17B:
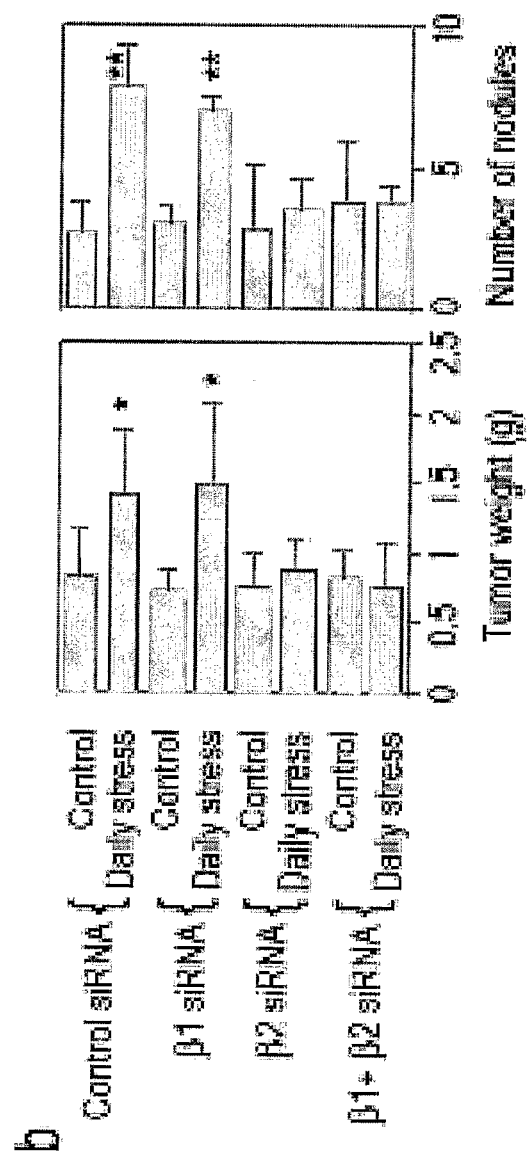

To further define the specific βARs responsible for stress effects, siRNA specific for human β1AR or β2AR were used. The siRNA downregulated βARs in the HeyA8 cells by β90% (FIG. 17A). To facilitate in vivo distribution in mice, the siRNA was incorporated into a neutral lipid liposome, DOPC (1,2-Dioleoyl-sn-glycero-3-phosphatidylcholine) (Landen et al., 2005). HeyA8-injected mice (n=10 per group) undergoing daily restraint stress were treated with either control, β1, β2, or β1+β2 siRNA three times per week. Both control and β1 siRNA failed to block stress-induced enhancement of tumor weight and nodules (stress effects continued to be significant at p<0.001), but siRNA to the β2AR efficiently blocked stress-mediated enhancement of tumor cell growth (FIG. 16B). Mice treated with combined β1 and β2 siRNA had results similar to the group treated with β2 siRNA alone (FIG. 16B).

Effect of Chronic Stress on Angiogenesis.

Figures 18A, 18B:
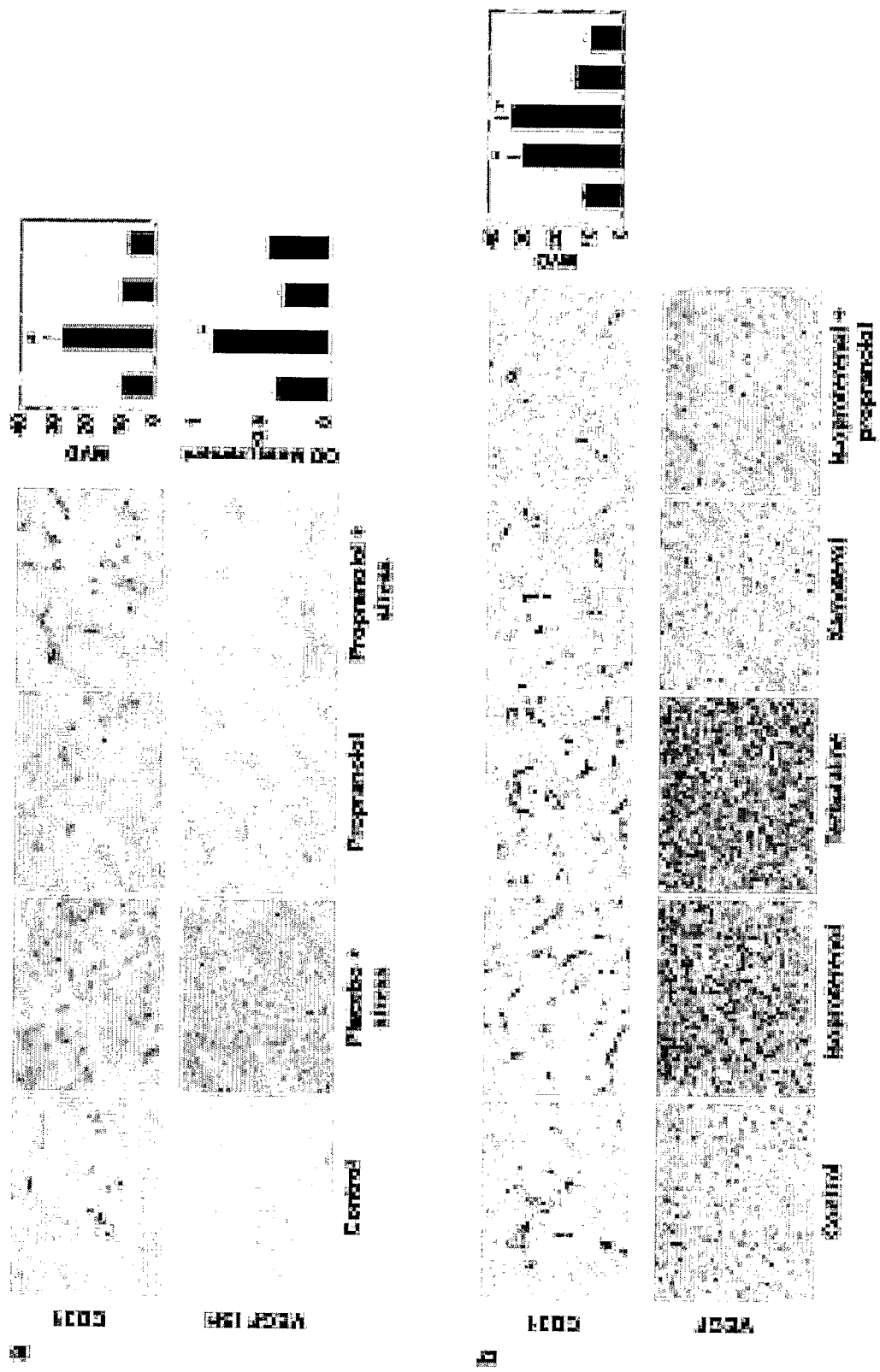
FIGS. 18A-18B. Angiogenesis is increased in chronically stressed animals. (A) HeyA8 tumor samples from control and stressed animals with placebo or propranolol pumps were stained for CD31, and mean vessel density (MVD) counts were quantified. Tumor samples were stained for VEGF by in situ hybridization and optical density measurements were calculated (p<0.001). (B) HeyA8 tumor samples from placebo, isoproterenol, terbutaline, xamoterol, or isoproterenol plus propranolol treated mice were stained for CD31 and VEGF. MVD was higher in the isoproterenol and terbutaline groups compared to controls or the combination therapy group. All pictures were taken at original magnification ×200. The bars in the graphs correspond to the labeled columns shown in the picture. *p<0.001
Figure 19:
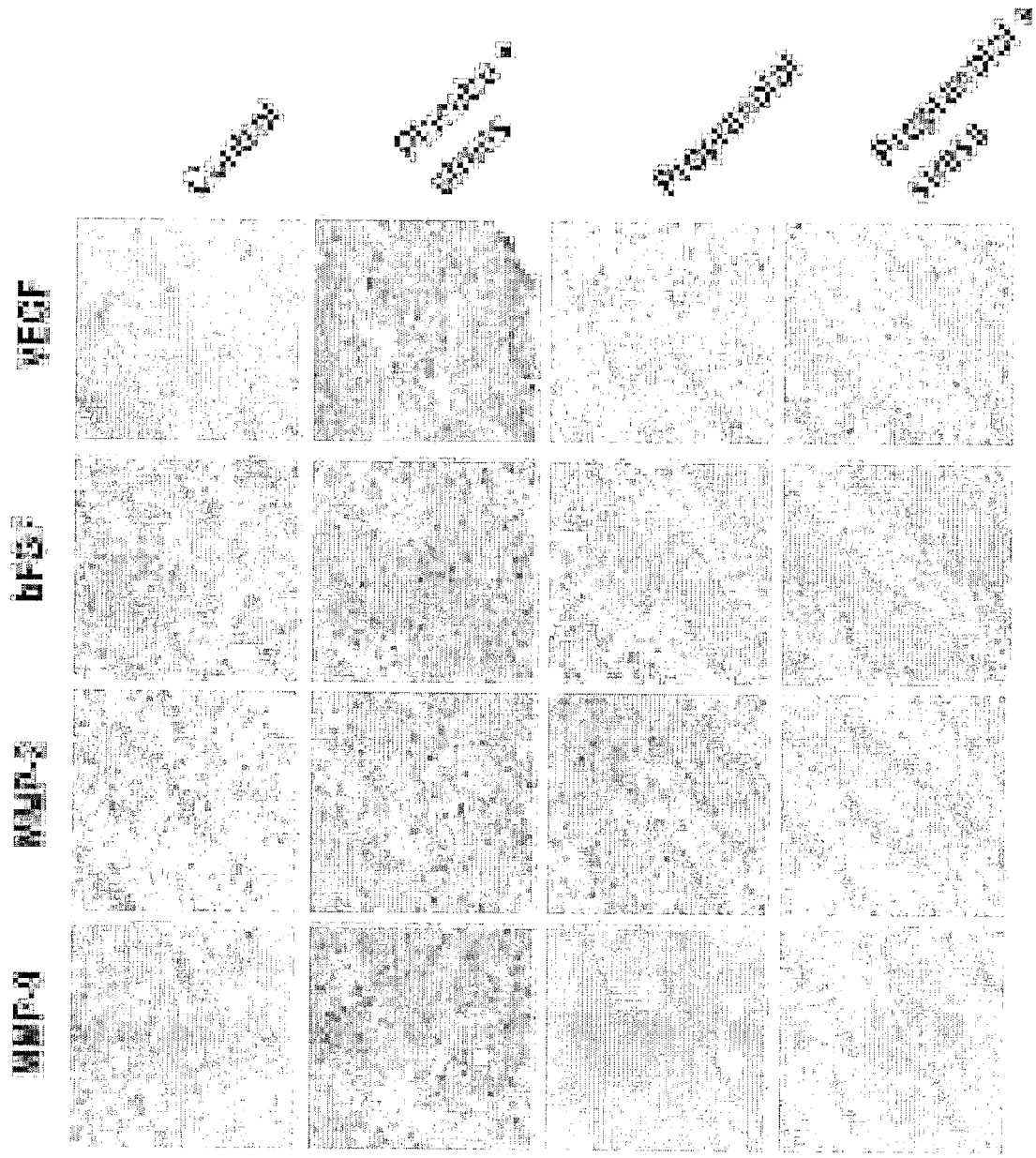
FIG. 19. Immunohistochemistry for VEGF, bPGF, MMP-2, and MMP-9 was performed in HeyA8 tumor samples from control and stressed animals treated with placebo or propranolol. All pictures were taken at original magnification ×200.

Based on previous in vitro data showing that norepinephrine and epinephrine can promote secretion of VEGF by ovarian cancer cells (Lutgendorf et al., 2003), the inventors sought to determine whether stress might induce similar effects in vivo. The vascular endothelial cell marker CD31 was assayed by immunohistochemistry, and mean vessel density (MVD) was counted in HeyA8 tumor samples from control and stressed animals treated with placebo or propranolol (FIG. 18A). Among animals treated with placebo, the average MVD count was 9.1±3.0 (range 5-13) in unstressed animals versus 27.1±10.7 (range 9-37) in stressed animals (p<0.001) (FIG. 18A). However, propranolol efficiently blocked stress-induced increases in MVD counts (FIG. 18A). Similarly, tumors harvested from animals treated with daily isoproterenol or terbutaline had significantly higher MVD counts compared to controls (p<0.001), and propranolol blocked that increase as well (FIG. 18B). Increased angiogenesis in stressed versus control tumor samples was accompanied by significant elevation of VEGF as measured by in situ hybridization (p<0.001, FIG. 18A). Immunohistochemistry of tumor samples from stressed animals also demonstrated increased protein levels of VEGF, MMP-2, and MMP-9 (FIG. 19).

Figures 20A, 20B, 20C:
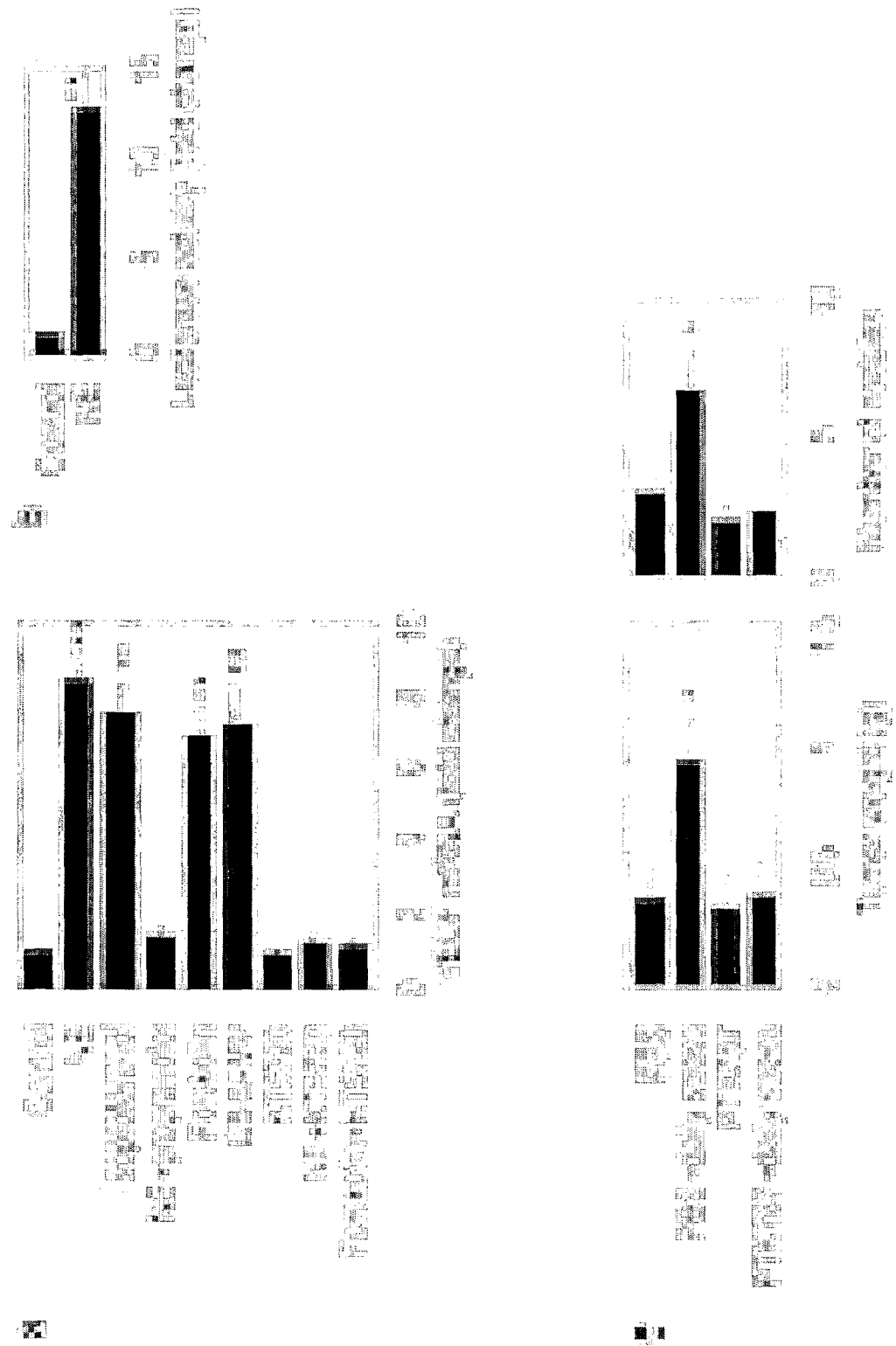
FIGS. 20A-20C. VEGF is stimulated by norepinephrine (NE) and mediates the effects of chronic stress on angiogenesis. (A) VEGF mRNA increased significantly when SKOV3ip1 cells were stimulated with norepinephrine 1 M, isoproterenol 1 µM, forskolin (activator of cAMP) 1 µM, or dibutyryl cAMP (db-cAMP) 1 mM. KT5720 (1 µM) is a selective inhibitor of the cAMP-dependent protein kinase A. (B) In SKOV3ip1 (βAR positive cell line), the VEGF promoter activity was increased by 12.8 fold after norepinephrine treatment compared to vehicle control. (C) Treatment with PTK787 blocked the stress induced increase in tumor weight and number of nodules compared to PBS and stress in mice injected with HeyA8 ovarian cancer cells. *$p \le 0.01$; **$p \le 0.001$.

To determine the mechanism by which catecholamines regulated VEGF production in stressed mice, transcriptional changes in activity of the VEGF gene were examined. The inventors previously found that catecholamines could increase VEGF protein production by ovarian cancer cell lines (Lutgendorf et al., 2003). RT-PCR analyses showed that this effect was mediated by increased VEGF gene transcription; VEGF mRNA expression increasing by a peak 8.4-fold 1.5 hours following treatment of SKOV3ip1 cells with norepinephrine (FIG. 20A). This effect was blocked by propranolol and mimicked by isoproterenol, implicating βARs as a key mediator (FIG. 20A). Consistent with that observation, βAR-negative A2780 ovarian cancer cells showed no increase in VEGF expression after norepinephrine treatment (data not shown). The adenylyl cyclase activator forskolin (1 µM) and the protein kinase A (PKA) activator dibutyryl cAMP (db-cAMP; 1 mM) also increased VEGF mRNA levels (FIG. 20A), suggesting that cAMP/PKA signaling pathway mediates these βAR-dependent effects. Consistent with that hypothesis, the PKA inhibitor KT5720 also efficiently blocked the effects of norepinephrine and forskolin on VEGF mRNA expression (FIG. 20A). To determine whether these effects stemmed from modulation of VEGF promoter activity (versus changes in mRNA stability), effects of norepinephrine on a reporter construct driving expression of luciferase from 2.5 kb of genomic DNA lying upstream of the human VEGF transcription start site were analyzed. As shown in FIG. 20B, 1 µM norepinephrine enhanced VEGF promoter activity by up to 12.8-fold in transiently transfected SKOV3ip1 cells.

To define the role of VEGF signaling in stress-enhanced tumor growth in vivo, animals were treated with the VEGF-R2 inhibitor PTK787. HeyA8-injected mice were randomized (n=10 per group) to control, oral placebo with stress, 50 mg/kg oral PTK787 daily with no stress, or PTK787 with stress (FIG. 20C). In placebo-treated animals, mean tumor weights and nodule numbers were significantly elevated by stress (p=0.007 and p=0.01, respectively). However, PTK787 efficiently blocked the effects of stress on both tumor weight and number of nodules. PTK787 did not affect tumor growth in non-stressed animals compared to controls.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,659,774
U.S. Pat. No. 4,682,195
U.S. Pat. No. 4,683,202
U.S. Pat. No. 4,816,571
U.S. Pat. No. 4,959,463
U.S. Pat. No. 5,030,453
U.S. Pat. No. 5,141,813
U.S. Pat. No. 5,214,136
U.S. Pat. No. 5,223,618
U.S. Pat. No. 5,223,618
U.S. Pat. No. 5,264,566
U.S. Pat. No. 5,378,825
U.S. Pat. No. 5,428,148
U.S. Pat. No. 5,446,137
U.S. Pat. No. 5,466,786
U.S. Pat. No. 5,470,967
U.S. Pat. No. 5,539,082
U.S. Pat. No. 5,539,082
U.S. Pat. No. 5,554,744
U.S. Pat. No. 5,574,146
U.S. Pat. No. 5,602,240
U.S. Pat. No. 5,602,244
U.S. Pat. No. 5,610,289
U.S. Pat. No. 5,614,617
U.S. Pat. No. 5,623,070
U.S. Pat. No. 5,645,897
U.S. Pat. No. 5,652,099
U.S. Pat. No. 5,670,663
U.S. Pat. No. 5,672,697
U.S. Pat. No. 5,681,947
U.S. Pat. No. 5,700,922
U.S. Pat. No. 5,705,629
U.S. Pat. No. 5,708,154
U.S. Pat. No. 5,714,331
U.S. Pat. No. 5,714,606
U.S. Pat. No. 5,719,262
U.S. Pat. No. 5,736,336
U.S. Pat. No. 5,763,167
U.S. Pat. No. 5,766,855
U.S. Pat. No. 5,773,571
U.S. Pat. No. 5,777,092
U.S. Pat. No. 5,786,461
U.S. Pat. No. 5,792,847
U.S. Pat. No. 5,858,988
U.S. Pat. No. 5,859,221
U.S. Pat. No. 5,872,232
U.S. Pat. No. 5,886,165
U.S. Pat. No. 5,891,625
U.S. Pat. No. 5,908,845
U.S. Pat. No. 5,962,016
U.S. Pat. No. 6,506,559
U.S. Pat. No. 6,573,099
U.S. Pat. No. 6,680,068
U.S. Appln. 2002/0168707
U.S. Appln. 2003/0012812
U.S. Appln. 2003/0051263
U.S. Appln. 2003/0055020
U.S. Appln. 2003/0159161
U.S. Appln. 2004/0064842
U.S. Appln. 2004/0204377
U.S. Appln. 2004/0208921
U.S. Appln. 2004/0265839
U.S. application Ser. 117,363
Aguirre Ghiso, *Oncogene*, 21:2513-24, 2002.
Ambros et al., *Nature*, 431:350-355, 2004.
Apte et al., *Gynecol. Oncol.*, 93:78-86, 2004.
Bailey and Sullivan, *Biochimica. Biophys. Acts.*, 239-252, 2000.
Bangham et al., *J. Mol. Biol*, 13(1):253-259, 1965.
Bonome et al., *Cancer Res. In press* 2006.
Brummelkamp et al., *Cancer Cell*, 2:243-247, 2002.
Cance et al., Clinical Cancer Research, 6:2417-2423, 2000.
Casamassima and Rozengurt, J Biol Chem, 273: 26149-56, 1998.
Daniel et al., *Kidney Int. Suppl.*, 57:S73-81, 1996.
Deamer and Uster, In: Liposome Preparation: Methods and Mechanisms, Ostro (Ed.), Liposomes, 1983.
Devroe and Silver, *Expert Opin. Biol. Ther.*, 4:319-327, 2004.
Dobrzanski et al, *Cancer Res.*, 64:910-919, 2004.
Dokka et al., Pharm Res, 17: 521-25, 2000.
Donze and Picard, *Nucleic Acids Res*, 30(10):e46, 2002.
Dorn et al., *Nucleic Acids Res.*, 32:e49, 2004.
duBois et al., *J Clin Oncol*, 17: 46-51, 1999.
Dubey et al, *J. Drug Target*, 12:257-264, 2004.
Duxbury et al., *Biochem. Biophys. Res. Commun.*, 311:786-792, 2003.
Duxbury et al., *Oncogene*, 23:1448-1456, 2004.
Egholm et al., *Nature*, 365(6446):566-568, 1993.
Elbashir et al., Nature, 411 (6836):494-498, 2001.
European Appln. 01219
European Appln. 266,032
Farhood et al., *Biochim. Biophys. Act*, 289-295, 1995.
Fire et al., *Nature*, 391(6669):806-811, 1998.
Flenniken et al., *Dev. Biol.*, 179:382-401, 1996.
Froehler et al., *Nucleic Acids Res.*, 14(13):5399-5407, 1986.
Gabizon, *Cancer Invest.*, 19:424-436, 2001.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Gregoriadis, In: *Drug Carriers in Biology and Medicine*, Gregoriadis (Ed.), 287-341, 1979.
Gutierrez-Puente et al., *J. Pharmacol. Exp. Ther.*, 291:865-869, 1999.
Halder et al., *Clinical Cancer Research*, 11: 8829-36, 2005.
Han et al., Ann Surg Oncol, 4:264-268, 1997.
Hannon and Rossi, *Nature*, 431:371-378, 2004.
Hassani et al., *J. Gene Med.*, 7(2):198-207, 2005.
Hecker et al., *Cancer Research*, 62:2699-2707, 2002.
Hortobagyi et al., *J. Clin. Oncol.*, 19:3422-3433, 2001.
Hsia et al., *J Cell Biol*, 160:753-67, 2003.
Jackson et al., *Nat. Biotechnol.*, 21:635-637, 2003.
Jemal et al, *CA Cancer J. Clin.*, 55(1):10-30, 2005.
Judson et al., *Cancer*, 86: 1551-56, 1999.

Kaneda et al., *Science,* 243:375-378, 1989.
Kato et al., *J. Biol. Chem.,* 266:3361-3364, 1991.
Kim et al., *Nat. Biotechnol.,* 22:321-325, 2004.
Kinch et al., *Clin. Exp. Metastasis,* 20:59-68, 2003.
Klein et al., *Gastroenterology,* 125:9-18, 2003.
Kohno et al., *Int J Cancer,* 97:336-43, 2002.
Kornberg and Baker, *DNA Replication,* 2nd Ed., Freeman, San Francisco, 1992.
Kornberg et al., Invest Opthalmol Vis Sci, 45:4463-69, 2004.
Kornberg, Head Neck, 20: 634-639, 1998.
Kostarelos et al., Int J Cancer, 112: 713-21, 2004.
Landen, Cancer Res, 65: 6910-18, 2005.
Langley et al., Cancer Research, 63: 2971-76, 2003.
Lewis et al., *Cell,* 115:787-798, 2003.
Lewis et al., *Nat. Genet.,* 32:107-108, 2002.
Lori et al., *Am. J. Pharmacogenomics,* 2:245-252, 2002.
Matsuda et al., *Proc. Natl. Acad. Sci. USA,* 101:16-22, 2004.
McCaffrey et al., *Nature,* 418:38-39, 2002.
McGuire et al., *New England Journal of Medicine,* 334:1-6, 1996.
McLean et al., Expert Opin Pharmacother, 4: 227-34, 2003.
Miller et al., *Biochemistry,* 37(37):12875-83, 1998.
Mitra et al., *Nature Reviews Molecular Cell Biology,* 6: 56-68, 2005.
Mitra et al., Proc Am Assoc Cancer Res, 2005.
Nemoto et al., *Pathobiology,* 65:195-203, 1997.
Nicolau et al., *Methods Enzymol.,* 149:157-176, 1987.
Noblitt et al., *Cancer Gene Ther.,* 11:757-766, 2004.
Ogawa et al, *Oncogene,* 19:6043-6052, 2000.
Owens et al., Cancer Res, 55:2752-2755, 1995.
Park et al., *Cancer Lett.,* 118:153-160, 1997.
PCT Appln. WO 92/20702
PCT Appln. WO02/100435A1
PCT Appln. WO03/015757A1
PCT Appln. WO04/002453A1
PCT Appln. WO04029213A2
Reich et al., *Mol. Vis.,* 9:210-216, 2003.
Remington's Pharmaceutical Sciences, 18th Ed. Mack Printing Company, 1289-1329, 1990.
Ryther et al., *Gene Ther.,* 12(1):5-11, 2004.
Sambrook et al., *In: Molecular cloning,* Cold Spring Harbor Laboratory Press, Cold Spring Harbor, N.Y., 2001.
Schaller and Parsons, *Trends in Cell Biology,* 3:258-62, 1993.
Schaller et al., *Mol Biol Cell,* 10:3489-3505, 1999.
Schaller, Biochim Biophys Acta, 1540:1-21, 2001.
Schaller, *J Endocrinol,* 150:1-7, 1996.
Schaller, *Trends Cell Biol,* 3:258-262, 1993.
Scheit, *In: Synthesis and Biological Function,* Wiley-Interscience, NY, 171-172, 1980.
Schlaepfer and Hunter, Trends in Cell Biology, 8: 151-57, 1998.
Schlaepfer et al., Prog Biophys Mol Biol, 71: 435-78, 1999.
Sein et al., Oncogene, 19: 5539-42, 2000.
Sheta et al., J Natl Cancer inst, 92: 1065-73, 2000.
Shibata et al., Cancer Res, 58: 900-903, 1998.
Sieg et al., *Nat Cell Biol,* 2:249-56, 2000.
Sioud and Sorensen, *Biochem. Biophys. Res. Comm.,* 312: 1220-1225, 2003.
Siwak et al., Clin Cancer Res, 8: 955-56, 2002.
Sledz et al., *Nat. Cell Biol.,* 5:834-839, 2003.
Song et al., *Nature Med.* 9:347-351, 2003.
Sonoda et al., *Journal of Biological Chemistry,* 275:16309-15, 2000.
Sood et al., Am J Pathol, 165:1087-1095, 2004.
Sood et al., *Cancer Biology & Therapy,* 1: 511-17, 2002.
Sorensen et al., *J. Mol. Biol.,* 327:761-66, 2003.
Soutschek et al., *Nature,* 432:173-178, 2004.
Spagnou et al., *Biochemistry,* 43:13348-13356, 2004.
Sulman et al., *Genomics,* 40:371-374, 1997.
Szoka and Papahadjopoulos, *Proc. Natl. Acad. Sci. USA,* 75:4194-4198, 1978.
Thaker et al., 36th Annual Meeting of the Society of Gynecologic Oncologists, Miami, Fla., 2005.
Thaker et al., *Clin. Cancer Res.,* 10:5145-5150, 2004.
Uchida et al., *Mol. Ther.,* 10:162-171, 2004.
Voskoglou-Nomikos et al., *Clin. Cancer Res.,* 9:4227-4239, 2003.
Walker-Daniels et al., *Prostate,* 41:275-80, 1999.
Wianny et al., *Nat. Cell Biol.,* 2:70-75, 2000.
Wong et al., *Gene,* 10:87-94, 1980.
Xia et al., *Nat. Biotechnol,* 20:1006-10, 2002.
Yang et al., *Oncogene,* 22:5694-701, 2003.
Zelinski et al., *Cancer Res.,* 61:2301, 2001.
Zhang et al., *J. Biol. Chem.,* 279:10677-684, 2004.

The invention claimed is:

1. A pharmaceutical composition comprising:
(a) a short inhibitory ribonucleic acid (siRNA) component comprising one or more siRNA, wherein the siRNA has a backbone moiety that is negatively charged; and
(b) a lipid component comprising a phospholipid component consisting of one or more neutral phospholipids selected from the group consisting of a phosphatidylcholine or a phosphatidylethanolamine phospholipid, wherein the phospholipid is not a lysophosphatidylcholine or lysophosphatidylethanolamine and further wherein the lipid component has a neutral charge;
wherein the lipid component forms a liposome that encapsulate the siRNA such that greater than 90% of the liposomes encapsulate siRNA, the siRNA is a double stranded nucleic acid of 18 to 100 nucleobases, and the liposome encapsulated siRNA is comprised in a pharmaceutically acceptable carrier, wherein the phospholipid component consists of DOPC.

2. A pharmaceutical composition comprising:
(a) a short inhibitory ribonucleic acid (siRNA) component comprising one or more siRNA, wherein the siRNA has a backbone moiety that is negatively charged; and
(b) a lipid component comprising a phospholipid component consisting of one or more neutral phospholipids selected from the group consisting of a phosphatidylcholine or a phosphatidylethanolamine phospholipid, wherein the phospholipid is not a lysophosphatidylcholine or lysophosphatidylethanolamine and further wherein the lipid component has a neutral charge;
wherein the lipid component forms a liposome that encapsulate the siRNA such that greater than 90% of the liposomes encapsulate siRNA, the siRNA is a double stranded nucleic acid of 18 to 100 nucleobases, and the liposome encapsulated siRNA is comprised in a pharmaceutically acceptable carrier, wherein the phospholipid component consists of two or more types of neutral phospholipids.

3. The composition of claim 1 or 2, wherein the siRNA inhibits the translation of a gene that promotes growth of a hyperplastic or cancerous mammalian cell.

4. A pharmaceutical composition comprising:
(a) a short inhibitory ribonucleic acid (siRNA) component comprising one or more siRNA, wherein the siRNA has a backbone moiety that is negatively charged; and
(b) a lipid component comprising a phospholipid component consisting of one or more neutral phospholipids selected from the group consisting of a phosphatidylcholine or a phosphatidylethanolamine phospholipid, wherein the phospholipid is not a lysophosphatidylcholine or lysophosphatidylethanolamine and further wherein the lipid component has a neutral charge;
wherein the lipid component forms a liposome that encapsulate the siRNA such that greater than 90% of the liposomes encapsulate siRNA, the siRNA is a double stranded nucleic acid of 18 to 100 nucleobases, and the liposome encapsulated siRNA is comprised in a pharmaceutically acceptable carrier, wherein the siRNA inhibits the translation of a gene that promotes growth of a hyperplastic or cancerous mammalian cell and wherein the gene is EphA2.

5. A pharmaceutical composition comprising:
(a) a short inhibitory ribonucleic acid (siRNA) component comprising one or more siRNA, wherein the siRNA has a backbone moiety that is negatively charged; and
(b) a lipid component comprising a phospholipid component consisting of one or more neutral phospholipids selected from the group consisting of a phosphatidylcholine or a phosphatidylethanolamine phospholipid, wherein the phospholipid is not a lysophosphatidylcholine or lysophosphatidylethanolamine and further wherein the lipid component has a neutral charge;
wherein the lipid component forms a liposome that encapsulate the siRNA such that greater than 90% of the liposomes encapsulate siRNA, the siRNA is a double stranded nucleic acid of 18 to 100 nucleobases, and the liposome encapsulated siRNA is comprised in a pharmaceutically acceptable carrier wherein the siRNA inhibits the translation of a gene that promotes growth of a hyperplastic or cancerous mammalian cell and wherein the gene is β2 adrenergic receptor (β2AR).

6. A pharmaceutical composition comprising:
(a) a short inhibitory ribonucleic acid (siRNA) component comprising one or more siRNA, wherein the siRNA has a backbone moiety that is negatively charged; and
(b) a lipid component comprising a phospholipid component consisting of one or more neutral phospholipids selected from the group consisting of a phosphatidylcholine or a phosphatidylethanolamine phospholipid, wherein the phospholipid is not a lysophosphatidylcholine or lysophosphatidylethanolamine and further wherein the lipid component has a neutral charge;
wherein the lipid component forms a liposome that encapsulate the siRNA such that greater than 90% of the liposomes encapsulate siRNA, the siRNA is a double stranded nucleic acid of 18 to 100 nucleobases, and the liposome encapsulated siRNA is comprised in a pharmaceutically acceptable carrier, wherein the siRNA inhibits the translation of a gene that promotes growth of a hyperplastic or cancerous mammalian cell and wherein the gene is focal adhesion kinase (FAK).

7. The composition of claim 6, wherein the lipid component comprises DOPC.

8. The composition of claim 6, wherein the siRNA component comprises SEQ ID NO:7, SEQ ID NO:8, SEQ ID NO:9, or SEQ ID NO:10.

9. The composition of claim 4, 6 or 5, wherein the phospholipid component consists of one or more of egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), palmitoyloeoyl phosphatidylcholine ("POPC"), dilinoleoylphosphatidylcholine distearoylphophatidylethanolamine ("DSPE"), dimyristoyl phosphatidylethanolamine ("DMPE"), dipalmitoyl phosphatidylethanolamine ("DPPE"), palmitoyloeoyl phosphatidylethanolamine ("POPE"), dioleoylphosphatidylethanolamine ("DOPE") or dioleoylphosphatidylcholine ("DOPC").

10. The composition of claim 1, 2, 4, 6 or 5, wherein the composition further comprises cholesterol or polyethyleneglycol (PEG).

11. The composition of claim 1, 2, 4, 6 or 5, wherein the siRNA is 18 to 30 nucleobases.

12. The composition of claim 1, 2, 4, 6 or 5, further comprising a chemotherapeutic agent.

* * * * *

UNITED STATES PATENT AND TRADEMARK OFFICE
CERTIFICATE OF CORRECTION

Page 1 of 1

PATENT NO. : 8,895,717 B2
APPLICATION NO. : 11/911639
DATED : November 25, 2014
INVENTOR(S) : Anil K. Sood et al.

It is certified that error appears in the above-identified patent and that said Letters Patent is hereby corrected as shown below:

In the Specification

In column 1, lines 10-13, delete paragraph and insert --This invention was made with Government support under grant number W81XWH-04-1-0227 awarded by the Department of Defense and grant number CA10929801 awarded by the National Institutes of Health. The Government has certain rights in the invention.--.

Signed and Sealed this
Twelfth Day of May, 2015

Michelle K. Lee
*Director of the United States Patent and Trademark Office*